(12) United States Patent
Katragadda et al.

(10) Patent No.: US 11,364,303 B2
(45) Date of Patent: Jun. 21, 2022

(54) CYSTEINE ENGINEERED ANTIBODY DRUG CONJUGATES

(71) Applicant: PFIZER INC., New York, NY (US)

(72) Inventors: Madan Katragadda, Acton, MA (US);
Russell Dushin, Old Lyme, CT (US);
Lawrence Nathan Tumey, Vestal, NY (US)

(73) Assignee: Pfizer Inc., New York, NY (US)

( * ) Notice: Subject to any disclaimer, the term of this patent is extended or adjusted under 35 U.S.C. 154(b) by 523 days.

(21) Appl. No.: 16/140,115

(22) Filed: Sep. 24, 2018

(65) Prior Publication Data
US 2019/0099499 A1  Apr. 4, 2019

Related U.S. Application Data

(60) Provisional application No. 62/565,260, filed on Sep. 29, 2017.

(51) Int. Cl.
| | |
|---|---|
| *A61K 47/68* | (2017.01) |
| *A61K 47/54* | (2017.01) |
| *A61P 31/00* | (2006.01) |
| *C07K 16/32* | (2006.01) |
| *A61P 35/00* | (2006.01) |
| *A61P 37/06* | (2006.01) |
| *C07K 16/28* | (2006.01) |
| *A61K 39/00* | (2006.01) |

(52) U.S. Cl.
CPC ........ *A61K 47/6889* (2017.08); *A61K 47/545* (2017.08); *A61K 47/6803* (2017.08); *A61K 47/6817* (2017.08); *A61K 47/6851* (2017.08); *A61P 31/00* (2018.01); *A61P 35/00* (2018.01); *A61P 37/06* (2018.01); *C07K 16/2803* (2013.01); *C07K 16/32* (2013.01); *A61K 2039/505* (2013.01); *C07K 2317/524* (2013.01); *C07K 2317/526* (2013.01); *C07K 2317/72* (2013.01); *C07K 2317/94* (2013.01)

(58) Field of Classification Search
None
See application file for complete search history.

(56) References Cited

U.S. PATENT DOCUMENTS

| | | | |
|---|---|---|---|
| 3,773,919 | A | 11/1973 | Boswell et al. |
| 4,485,045 | A | 11/1984 | Regen |
| 4,544,545 | A | 10/1985 | Ryan et al. |
| 5,013,556 | A | 5/1991 | Woodle et al. |

(Continued)

FOREIGN PATENT DOCUMENTS

| | | |
|---|---|---|
| EP | 2083017 | 7/2009 |
| JP | 2009095249 | 5/2009 |

(Continued)

OTHER PUBLICATIONS

Strop et al, "Location Matters: Site of Conjugation Modulates Stability and Pharmacokinetics of Antibody Drug Conjugates", Chemistry & Biology 20:161-167 (2013).

(Continued)

*Primary Examiner* — Karl J Puttlitz
(74) *Attorney, Agent, or Firm* — Austin W. Zhang

(57) ABSTRACT

The invention relates to polypeptides, antibodies, and antigen-binding fragments thereof, that comprise an engineered cysteine for site-specific conjugation.

6 Claims, 5 Drawing Sheets
Specification includes a Sequence Listing.

(56) References Cited

U.S. PATENT DOCUMENTS

| | | | |
|---|---|---|---|
| 5,208,020 | A | 5/1993 | Chari et al. |
| 5,648,095 | A | 7/1997 | Illum et al. |
| 5,821,337 | A | 10/1998 | Carter et al. |
| 5,981,568 | A | 11/1999 | Kunz et al. |
| 6,309,633 | B1 | 10/2001 | Ekwuribe et al. |
| 6,461,603 | B2 | 10/2002 | Bentley et al. |
| 7,521,541 | B2 | 4/2009 | Eigenbrot et al. |
| 7,855,275 | B2 | 12/2010 | Eigenbrot et al. |
| 7,989,594 | B2 | 8/2011 | Humphreys et al. |
| 8,337,856 | B2 | 12/2012 | Blättler et al. |
| 10,086,085 | B2 | 10/2018 | Maderna et al. |
| 2005/0249723 | A1 | 11/2005 | Lazar |
| 2006/0205670 | A1 | 9/2006 | Bradshaw et al. |
| 2008/0306246 | A1 | 12/2008 | Heywood |
| 2009/0041770 | A1 | 2/2009 | Chamberlain et al. |
| 2009/0252729 | A1 | 10/2009 | Farrington et al. |
| 2009/0258420 | A1 | 10/2009 | van Vlijmen et al. |
| 2011/0301334 | A1 | 12/2011 | Bhakta et al. |
| 2015/0209445 | A1* | 7/2015 | Maderna ............ C07D 417/14 424/181.1 |
| 2015/0352225 | A1 | 12/2015 | Rabuka et al. |
| 2016/0067351 | A1* | 3/2016 | Geierstanger ........... A61P 35/00 435/69.6 |
| 2016/0271270 | A1 | 9/2016 | Maderna et al. |
| 2017/0021033 | A1* | 1/2017 | Geierstanger ...... A61K 47/6871 |
| 2017/0151341 | A1 | 6/2017 | Ma et al. |
| 2017/0216452 | A1 | 8/2017 | Ma et al. |
| 2018/0339060 | A1 | 11/2018 | Maderna et al. |

FOREIGN PATENT DOCUMENTS

| | | |
|---|---|---|
| WO | 2000053211 | 9/2000 |
| WO | 2011005481 | 1/2001 |
| WO | 2006034488 | 3/2006 |
| WO | 2007038658 | 4/2007 |
| WO | 2008032833 | 3/2008 |
| WO | 2008038024 | 4/2008 |
| WO | 2008141044 | 11/2008 |
| WO | 2009009103 | 1/2009 |
| WO | 2009092011 | 7/2009 |
| WO | 2010141902 | 12/2010 |
| WO | 2011044368 | 4/2011 |
| WO | 2011118739 | 9/2011 |
| WO | 2012/059882 | 5/2012 |
| WO | 2012162482 | 11/2012 |
| WO | 2013/072813 | 5/2013 |
| WO | 2013072813 | 5/2013 |
| WO | 2013093809 | 6/2013 |
| WO | 2013/173337 | 11/2013 |
| WO | 2014/022592 | 2/2014 |
| WO | 2014/072888 | 5/2014 |
| WO | 2014/124316 | 8/2014 |
| WO | 2015023355 | 2/2015 |
| WO | 2015110935 | 7/2015 |
| WO | 2016151432 | 9/2016 |
| WO | 2017093844 | 6/2017 |
| WO | 2017093845 | 8/2017 |
| WO | 2018025168 | 8/2018 |

OTHER PUBLICATIONS

Sung et al, "Caveolae-mediated endocytosis as a novel mechanism of resistance to T-DM1 ADC", Presentation Abstract#2113, AACR Annual Meeting, New Orleans, LA, Apr. 16-20, 2016.

Thomas et al., "Overcoming Multidrug Resistance in Cancer: An Update on the Clinical Strategy of Inhibiting P-Glycoprotein", Cancer Control 10(2):159-165 (2003).

Tian et al., "A general approach to site-specific antibody drug conjugates", PNAS 111(5):1766-1771 (2014).

Toda et al, "Rapid, Stable, Chemoselective Labeling of Thiols with Julia-Kocienski-like Reagents: A Serum-Stable Alternative to Maleimide-Based Protein Conjugation", Angew Chem. Int. Ed. 52:12592-12596 (2013).

Tumey, "In Vivo ADC Stability", Hanson-Wade webinar, Jun. 3, 2014 (36 pages).

Tumey, "Metabolism of ADC Linkers & Payloads—How In Vivo & In Vitro Stability Data is Used to Advance Decision Making", ADC World Summit, San Diego, CA, Oct. 26-19, 2014 (29 pages).

Tumey et al., "Mild Method for Succinimide Hydrolysis on ADCs: Impact on ADC Potency, Stability, Exposure, and Efficacy", Bioconjugate Chemistry 25:1871-1880 (2014).

Tumey, "ADC Biotransformation: Metabolism of ADC Linkers & Payloads in vitro and in vivo", WRIB, Miami, FL, Mar. 2015 (25 pages).

Tumey, "Dreaming Big and Thinking Small: Applying Medicinal Chemistry Strategy to Antibody-Drug-Conjugates", ACS Webinar, Jun. 2016 (33 pages).

Tumey, "Site-specific Conjugation for the Advancement of New Linker-Payloads", ADC World Summit, Berlin, Germany, Feb. 2016 (30 pages).

Tumey et al; "Optimization of Tubulysin Antibody-Drug Conjugates: A Study in Addressing ADC Metabolism", ACS Medicinal Chemistry Letters, vol. 7, No. 11, pp. 977-982, 2016.

Vogel et al, "Efficacy and Safety of Trastuzumab as a Single Agent in First-Line Treatment of HER2-Overexpressing Metastatic Breast Cancer", Journal of Clinical Oncology 20(3):719-726 (2002).

Von Pawel-Rammingen et al., "IdeS, a novel streptococcal cysteine proteinase with unique specificity for immunoglobulin G", The EMBO Journal 21(7):1607-1615 (2002).

Wolff et al, "American Society of Clinical Oncology/College of American Pathologists Guideline Recommendations for Human Epidermal Growth Factor Receptor 2 Testing in Breast Cancer", Journal of Clinical Oncology 25(1):118-145 (2007).

Wolff et al, "Recommendations for Human Epidermal Growth Factor Receptor 2 Testing in Breast Cancer: American Society of Clinical Oncology/College of American Pathologists Clinical Practice Guideline Update", Journal of Clinical Oncology 31(31):3997-4013 (2013).

Xie et al, "Pharmacokinetics and Biodistribution of the Antitimor Immunoconjugate, Cantuzumab Mertansine (huC242-DM1), and Its Two Components in Mice", The Journal of Pharmacology and Experimental Therapeutics 308(3):1073-1082 (2004).

Yamamoto et al, "Similarity of protein encoded by the human c-erb-B-2 gene to epidermal growth factor receptor", Nature 319:230-234 (1986).

Yu et al, "Engineering Hydrophobic Protein-Carbohydrate Interactions to Fine-Tune Monoclonal Antibodies", Journal of the American Chemical Society 135:9723-9732 (2013).

Partial International Serarch, PCT/IB2016/057018, dated Feb. 27, 2017, 9 pages.

Laguzza et al. "New antitumor monoclonal antibody-vinca conjugates ly203725 and related compounds: Design, preparation, and representative in vivo activity." J. Med. Chem. 32:548-555 (1989).

Lilo, A. et al. "A human single-chain antibody specific for integrin alpha 3 beta 1 capable of cell internalization and delivery of antitumor agents", Chemistry & Biology 11:897-906 (2004).

Langer, "New methods of drug delivery", Science 249:1527-1533 (1990).

Wu et al. "Arming antibodies: prospects and challenges for immunoconjugates", Nature Biotechnology 23(9):1137-1146 (2005).

Bird et al.; "Single-Chain Antigen-Binding Proteins" Science; vol. 242; pp. 424-426; 1988.

Brinkley; "A Brief Survey of Methods for Preparing Protein Conjugates with Dyes, Haptens, and Cross-Linking Reagents" Bioconj. Chem.; vol. 3; pp. 2-13; 1992.

Caceci et al.; "Fitting Curves to Data: The Simplex algorithm is the answer"; BYTE; vol. 3; pp. 340-362; 1984.

Edelman et al.; The Covalent Structure of an Entire γG Immunoglobulin Molecule; PNAS vol. 63, pp. 78-85, 1969.

Eppstein et al.; "Biological activity of liposome-encapsulated murine interferon γ is mediated by a cell membrane receptor"; PNAS; vol. 82; pp. 3688-3692; 1985.

G. Hermanson; Modification of Nucleic Acids and Oligonucleotides, Bioconjugate Techniques, pp. 40-55, 1996.

G. Hermanson; "Chemical Modification of Nucleic Acids and Oligonucleotides", Bioconjugate Techniques, pp. 643-671, 1996.

(56) References Cited

OTHER PUBLICATIONS

Holliger et al.; "Diabodies: Small bivalent and bispecific antibody fragments"; PNAS; vol. 90; pp. 6444-6448; 1993.

Hu et al; "Minibody: A Novel Engineered Anti-Carcinoembryonic Antigen Antibody Fragment (Single-Chain Fv-CH3) Which Exhibits Rapid, High-Level Targeting of Xenografts"; Cancer Res.; vol. 56; pp. 3055-3061; 1996.

Huston et al. "Protein engineering of antibody binding sites: Recovery of specific activity in an anti-digoxin single-chain Fv analogue produced in *Escherichia coli*" PNAS; vol. 85; pp. 5879-5883; 1988.

Hwang et al. "Hepatic uptake and degradation of unilamellar sphingomyelin/cholesterol liposomes: A kinetic study"; PNAS vol. 77; No. 7; pp. 4030-4034; 1980.

Kim et al.; "Statistical Modeling of the Drug Load Distribution on Trastuzumab Emtansine (Kadcyla), a Lysine-Linked Antibody Drug Conjugate" Bioconj. Chemistry; vol. 25; pp. 1223-1232; 2014.

Kunkel; "Rapid and efficient site-specific mutagenesis without phenotypic selection" PNAS; vol. 82; pp. 488-492; 1985.

Means & Feeney; "Chemical Modifications of Proteins: History and Applications"; Bioconj. Chemistry; vol. 1; pp. 2-12; 1990.

Olafsen et al.; "Characterization of engineered anti-p185HER-2 (scFv-CH3)2 antibody fragments (minibodies) for tumor targeting" Protein Engineering, Design & Selection; vol. 17; No. 4; pp. 315-323; 2004.

Poljak; "Production and structure of diabodies: The first crystal structure of a diabody, a bivalent antibody fragment, confirms previous predicted structures and techniques for generating bispecific bivalent antibody fragments of considerable therapeutic potential" Structure; vol. 2; No. 12; 1994.

Ward et al.; "Binding activities of a repertoire of single immunoglobulin variable domains secreted from *Escherichia coli*"; Nature; vol. 341; 1989.

Wong & Lohman; "A double-filter method for nitrocellulose-filter binding: Application to protein-nucleic acid interactions" PNAS; vol. 90; pp. 5428-5432; 1993.

Zoller & Smith; "Oligonucleotide-directed mutagenesis using M13-derived vectors: an efficient and general procedure for the production of point mutations in any fragment of DNA"; Nucleic Acids Res.; vol. 10; No. 20; 1982.

Boswell et al., "Impact of Drug Conjugation on Pharmacokinetics and Tissue Distribution of Anti-STEAP1 Antibody-Drug Conjugates in Rats.", Bioconjugate Chemistry, vol. 22, 2011, pp. 1994-2004.

Boswell et al., "Impact of Drug Conjugation on Pharmacokinetics and Tissue Distribution of Anti-STEAP1 Antibody-Drug Conjugates in Rats", Bioconjugate Chemistry, Supporting Information, 2011, pp. 1-7.

Chan et al., "A proprotein convertase subtilisin/kexin type 9 neutralizing antibody reduces serum cholesterol in mice and nonhuman primates." PNAS, vol. 106, No. 24, 2009, pp. 9820-9825.

Cho et al., "Structure of the extracellular region of HER2 alone and in complex with the Herceptin Fab." Nature, vol. 421, 2003, pp. 756-760.

Stimmel et al. J. of Biological Chemistry, vol. 275, No. 39, pp. 30445-30450, 2000.

Goldmacher et al., "Antibody-drug conjugates: using monoclonal antibodies for delivery of cytotoxic payloads to cancer cells", Therapeutic Delivery, vol. 2, No. 3, 2011, pp. 397-416.

Junutula et al., "Site-specific conjugation of a cytotoxic drug to an antibody improves the therapeutic index", Nature Biotechnology, vol. 26, No. 8, 2008, pp. 925-932.

Junutula et al., "Rapid identification of reactive cysteine residues for site-specific labeling of antibody-Fabs" J. of Immunological Methods, vol. 332, 2008, pp. 41-52.

Junutula et al., "Rapid identification of reactive cysteine residues for site-specific labeling of antibody-Fabs." J. of Immunological Methods, vol. 332, 2008, Supplementary data, pp. 1-12.

Junutula et al., "Engineered Thio-Trastuzumab-DM1 Conjugate with an Improved Therapeutic Index to Target Human Epidermal Growth Factor Receptor 2-Positive Breast Cancer.", Clinical Cancer Research, vol. 16, No. 19, 2010, pp. 4769-4778.

Krivov et al., "Improved prediction of protein side-chain conformations with SCWRL4." Proteins, vol. 77, 2009, pp. 778-795.

Kipriyanov et al., "Recombinant Single-chain Fv Fragments Carrying C-Terminal Cysteine Residues: Production of Bivalent and Biotinylated Miniantibodies.", Molecular Immunology, vol. 31, No. 4, 1994, pp. 1047-1058.

Shen et al., "Conjugation site modulates the in vivo stability and therapeutic activity of antibody-drug conjugates." Nature Biotechnology, vol. 30, No. 2, 2012, pp. 184-191.

Shen et al., "Conjugation site modulates the in vivo stability and therapeutic activity of antibody-drug conjugates." Nature Biotechnology, vol. 30, No. 2, 2012, Supplementary Data, pp. 1-26.

Sondermann et al., "The 3.2-Å crystal structure of the human IgG1 Fc fragment-FcγRIII complex." Nature, vol. 406, 2000, pp. 267-273.

Spassov and Yan, "A fast and accurate computational approach to protein ionization." Protein Science, vol. 17, 2008, pp. 1955-1970.

Teplyakov et al., "Epitope Mapping of Anti-Interieukin-13 Neutralizing Antibody CNTO607." J. Molecular Biology, vol. 389, 2009, pp. 115-123.

Voynov et al. "Design and application of antibody cysteine variants", Bioconjugate Chemistry, ACS, vol. 21, No. 2, 2010, pp. 385-392.

Ye et al., "Synthetic antibodies for specific recognition and crystallization of structured RNA." PNAS, vol. 105, No. 1, 2008, pp. 82-87.

Alley et al, "Contribution of Linker Stability to the Activities of Anticancer Immunoconjugates", Bioconjugate Chemistry 19:759-765 (2008).

Anbazhagan et al, "Association of c-erbB-2 expression and S-phase fraction in the prognosis of node positive breast cancer", Annals of Oncology 2:47-53 (1991).

Andrulis et al, "neu/erbB-2 Amplification Identifies a Poor-Prognosis Group of Women With Node-Negative Breast Cancer", Journal of Clinical Oncology 16(4):1340-1349 (1998).

Badescu et al, "A New Reagent for Stable Thiol-Specific Conjugation", Bioconjugate Chemistry 25:460-469 (2014).

Badescu et al, "Bridging Disulfides for Stable and Defined Antibody Drug Conjugates", Bioconjugate Chemistry 25:1124-1136 (2014).

Bastiani et al, "Caveolae at a glance", Journal of Cell Science 123:3831-3836 (2010).

Béranger et al; "IMGT Scientific chart: Correspondence between the IMGT unique numbering for C-DOMAIN, the IMGT exon numbering, the Eu and Kabat numberings: Human IGHG" (May 17, 2001), Retrieved from the Internet: URL:http://www.imgt.org/IMGTScientificChart/Numbering/Hu_IGHGnber.html.

Boghaert et al, "Determination of pharmacokinetic values of calicheamicin-antibody conjugates in mice by plasmon resonance analysis of small (5 µl) blood samples", Cancer Chemother Pharmacol 61:1027-1035 (2008).

Boswell et al, "Effects of Charge on Antibody Tissue Distribution and Pharmacokinetics", Bioconjugate Chemistry 21:2153-2163 (2010).

Bumbaca et al, "Physiochemical and Biochemical Factors Influencing the Pharmacokinetics of Antibody Therapeutics", The AAPS Journal 14(3):554-558 (2012).

Burke et al, "Development and pharmacological properties of PEGylated glucuronide-auristatin linkers", Presentation Abstract #1786, AACR Annual Meeting, San Diego, CA, Apr. 5-9, 2014.

Burris et al, "Phase II Study of the Antibody Drug Conjugate Trastuzumab-DM1 for the Treatment of Human Epidermal Growth Factor Receptor 2 (HER2)-Positive Breast Cancer After Prior HER2-Directed Therapy", Journal of Clinical Oncology 29(4):398-405 (2010).

Burton, "Immunoglobulin G: Functional Sites", Molecular Immunology 22(3):161-206 (1985).

Carter et al, "Humanization of an anti-p185HER2 antibody for human cancer therapy", Proc. Natl. Acad. Sci. USA 89:4285-4289 (1992).

Chari et al, "Immunoconjugates Containing Novel Maytansinoids: Promising Anticancer Drugs", Cancer Research 52:127-131 (1992).

(56) References Cited

OTHER PUBLICATIONS

Chazin et al, "Transformation mediated by the human HER-2 gene independent of the epidermal growth factor receptor", Oncogene 7:1859-1866 (1992).
Christie et al, "Stabilization of cysteine-linked antibody drug conjugates with N-aryl maleimides", Journal of Controlled Release 220:660-670 (2015).
Database Genbank [online] (Mar. 30, 1995), "Human c-erb-B-2 mRNA [*Homo sapiens*]", retrieved from www.NCBI.NLM.NIH. GOV Database Accession No. X03363.1.
Di Fiore et al, "erbB-2 Is a Potent Oncogene When Overexpressed in NIH/3T3 Cells", Science 237(4811):178-182 (1987).
Di Joseph et al, "CMC-544 (inotuzamab ozogamicin): A CD22-targeted immunoconjugate of calicheamicin", Hematology Meeting Reports 5(6):74-77 (2008).
Dokter et al., "Impressive efficacy and safety profile of a novel generation duocarmycin-based HER2-targeting ADC", Presentation Abstract #2651, AACR Annual Meeting, San Diego, CA, Apr. 5-9, 2014.
Doronina et al., "Development of potent monoclonal antibody auristatin conjugates for cancer therapy", Nature Biotechnology 21(7):778-784 (2003).
Doronina et al, "Elucidating the role of drug-linker hydrophobicity in the disposition of antibody-drug conjugates", Presentation Abstract #4470, AACR Annual Meeting, San Diego, CA, Apr. 5-9, 2014.
Dorywalska et al, "Effect of Attachment Site on Stability of Cleavable Antibody Drug Conjugates", Bioconjugate Chemistry 26:650-659 (2015).
Erickson et al, "The Effect of Different Linkers on Target Cell Catabolism and Pharmacokinetics/Pharmacodynamics of Trastuzamab Maytansinoid Conjugates", Molecular Cancer Therapeutics 11(5):1133-1142 (2012).
Eustáquio et al, "Spliceostatin hemiketal biosynthesis in *Burkholderia* spp. is catalyzed by an iron/α-ketoglutarate-dependent dioxygenase", PNAS 111(33):E3376-E3385 (2014).
Fujimoto-Ouchi et al, "Antitumor activity of trastuzumab in combination with chemotherapy in human gastric cancer kenograft models", Cancer Chemother Pharmacol 59:795-805 (2007).
Gancberg et al, "Evaluation of HER-2/NEU protein expression in breast cancer by immunohistochemistry: an interlaboratory study assessing the reproducibility of HER-2/NEU testing", Breast Cancer Research and Treatment 74:113-120 (2002).
Guy et al, "Expression of the neu protooncogene in the mammary epithelium of transgenic mice induces metastatic disease", Proc. Natl. Acad. Sci. USA 89:10578-10582 (1992).
Hamblett et al, "Effects of Drug Loading on the Antitumor Activity of a Monoclonal Antibody Drug Conjugate", Clinical Cancer Research 10:7063-7070 (2004).
He et al, "Cytotoxic Spliceostatins from *Burkholderia* sp. and Their Semisynthetic Analogues", Journal of Natural Products 77:1864-1870 (2014).
Hudziak et al, "Increased expression of the putative growth factor receptor p185HER2 causes transformation and tumorigenesis of NIH 3T3 cells", Proc. Natl. Acad. Sci. USA 84:7159-7163 (1987).
Jackson et al, "In Vitro and In Vivo Evaluation of Cysteine and Site Specific Conjugated Herceptin Antibody-Drug Conjugates", PLOS ONE 9(1):E83865 (2014).
Jacobs et al, "Comparison of Fluorescence in Situ Hybridization and Immunohistochemistry for the Evaluation of HER-2/neu in Breast Cancer", Journal of Clinical Oncology 17(7):1974-1982 (1999).
Jeffrey et al, "Development and Properties of β-Glucuronide Linkers for Monoclonal Antibody-Drug Conjugates", Bioconjugate Chemistry 17:831-840 (2006).
Kellogg et al, "Disulfide-Linked Antibody-Maytansinoid Conjugates: Optimization of In Vivo Activity by Varying the Steric Hindrance at Carbon Atoms Adjacent to the Disulfide Linkage", Bioconjugate Chemistry 22:717-727 (2011).

Kern et al, "Discovery of Pyrophosphate Diesters as Tunable, Soluble, and Bioorthogonal Linkers for Site-Specific Antibody-Drug Conjugates", Journal of the American Chemical Society 138:1430-1445 (2016).
Kim et al, "Strategies and Advancement in Antibody-Drug Conjugate Optimization for Targeted Cancer Therapeutics", Biomolecules & Therapeutics 23(6):493-509 (2015).
Kovtun et al, "Antibody-Drug Conjugates Designed to Eradicate Tumors with Homogeneous and Heterogeneous Expression of the Target Antigen", Cancer Research 66(6):3214-3221 (2006).
Krop et al, "Phase I Study of Trastuzumab-DM1, an HER2 Antibody-Drug Conjugate, Given Every 3 Weeks to Patients With HER2-Positive Metastatic Breast Cancer", Journal of Clinical Oncology 28(16):2698-2704 (2010).
Lin et al, "Pharmacokinetic Considerations for Antibody Drug Conjugates", Pharm Res 29:2354-2366 (2012).
Lyon et al, "Self-hydrolyzing maleimides improve the stability and pharmacological properties of antibody-drug conjugates", Nature Biotechnology 32(10):1059-1062 (2014).
Lyon et al, "Self-stabilizing ADCs: antibody-drug conjugates prepared with maleimido drug-linkers that catalyze their own thiosuccinimide ring hydrolysis", Presentation Abstract #4333, AACR Annual Meeting, Washington, DC, Apr. 6-10, 2013.
Lyon et al., "Reducing hydrophobicity of homogeneous antibody-drug conjugates improves pharmacokinetics and therapeutic index", Nature Biotechnology 33:733-735 (2015).
Lyons et al, "Site-specific attachment to recombinant antibodies via introduced surface cystein residues", Protein Engineering 3(8):703-708 (1990).
Martin et al, "HER2 in solid tumors: more than 10 years under the microscope; where are they now?", Future Oncology 10(8):1469-1486 (2014).
Ménard et al, "HER2 overexpression in various tumor types, focussing on its relationship to the development of invasive breast cancer", Annals of Oncology 12(Suppl. 1):S15-S19 (2001).
Owens et al, "HER2 Amplification Ratios by Fluorescence In Situ Hybridization and Correlation with Immunohistochemistry in a Cohort of 6556 Breast Cancer Tissues", Clinical Breast Cancer 5(1):63-69 (2004).
PCT International Search Report and Written Opinion for International Patent Application No. PCT/IB2016/057017 dated Apr. 25, 2017.
Phillips et al, "Targeting HER2-Positive Breast Cancer with Trastuzumab-DM1, an Antibody-Cytotoxic Drug Conjugate", Cancer Research 68(22):9280-9290 (2008).
Poljak, "Production and structure of diabodies", Structure 2:1121-1123 (1994).
Polson et al, "Antibody-Drug Conjugates for the Treatment of Non-Hodgkin's Lymphoma: Target and Linker-Drug Selection", Cancer Research 69(6):2358-2364 (2009).
Press et al, "Diagnostic Evaluation of HER-2 as a Molecular Target: An Assessment of Accuracy and Reproducibility of Laboratory Testing in Large, Prospective, Randomized Clinical Trials", Clinical Cancer Research 11(18):6598-6607 (2005).
Remillard et al, "Antimitotic Activity of the Potent Tumor Inhibitor Maytansine", Science 189(4207): 1002-1005 (1975).
Sapra, "A Novel Site-Specific HER2-ADC for Treatment of HER2+ Solid Tumors", Presentation #868, 2016 AACR Annual Meeting, New Orleans, LA, Apr. 17, 2016 (15 pages).
Sapra, "A Novel Site-Specific HER2-ADC for Treatment of HER2+ Solid Tumors", Bioconjugates: From Targets to Therapeutics, San Francisco, CA, Jun. 14, 2016 (18 pages).
Sauter et al, "Guidelines for Human Epidermal Growth Factor Receptor 2 Testing: Biologic and Methodologic Considerations", Journal of Clinical Oncology 27(8):1323-1333 (2009).
Scholl et al, "Targeting HER2 in other tumor types", Annals of Oncology 12(Suppl. 1):S81-S87 (2001).
Semba et al., "A v-erbB-related protooncogene, c-erbB-2, is distinct from the c-erbB-1/epidermal growth factor-receptor gene and is amplified in a human salivary gland adenocarcinoma", Proc. Natl. Acad. Sci. USA 82:6497-6501 (1985).

(56) References Cited

OTHER PUBLICATIONS

Senter et al, "The discovery and development of brentuximab vedotin for use in relapsed Hodgkin lymphoma and systemic anaplasitc large cell lymphoma", Nature Biotechnology 30(7):631-637 (2012).
Slamon et al, "Human Breast Cancer: Correlation of Relapse and Survival with Amplification of the HER-2/neu Oncogene", Science 235(4785):177-182 (1987).
Slamon et al, "Studies of the HER-2/neu Proto-oncogene in Human Breast and Ovarian Cancer", Science 244(4905):707-712 (1989).

\* cited by examiner

US 11,364,303 B2

CYSTEINE ENGINEERED ANTIBODY DRUG CONJUGATES

CROSS REFERENCE TO RELATED APPLICATIONS

This application claims benefit under 35 U.S.C. 119(e) of U.S. Provisional Application No. 62/565,260, filed Sep. 29, 2017, the contents of which are incorporated herein by reference in their entirety.

SEQUENCE LISTING

In accordance with 37 CFR 1.52(e)(5), a Sequence Listing in the form of an ASCII text file (entitled "PC72358A_Seq_Listing_ST25.txt," created on Aug. 14, 2018, and 40.0 KB in size) is incorporated herein by reference in its entirety.

FIELD OF THE INVENTION

This invention relates to antibodies, and antigen-binding fragments thereof, engineered to introduce amino acids for site-specific conjugation.

BACKGROUND OF THE INVENTION

Antibodies have been conjugated to a variety of cytotoxic drugs, including small molecules that alkylate DNA (e.g., duocarmycin and calicheamicin), disrupt microtubules (e.g., maytansinoids and auristatins) or bind DNA (e.g., anthracyclins). One such antibody-drug conjugate (ADC) comprising a humanized anti-CD33 antibody conjugated to calicheamicin—Mylotarg™ (gemtuzumab ozogamicin)—has been approved for treating acute myeloid leukemia. Adcetris™ (brentuximab vedotin), an ADC comprising a chimeric antibody to CD30 conjugated to the auristatin monomethyl auristatin E (MMAE) has been approved for treatment of Hodgkin's lymphoma and anaplastic large cell lymphoma.

Although ADCs hold promise for cancer therapy, cytotoxic drugs are generally conjugated to the antibodies via lysine side chains or by reducing inter-chain disulfide bonds present in the antibodies to provide activated cysteine sulfhydryl groups. This non-specific conjugation approach, however, has numerous drawbacks. For example, drug conjugation to antibody lysine residues is complicated by the fact that there are many lysine residues (~30) in an antibody available for conjugation. As a result, lysine conjugation often generates a very heterogeneous profile, and this may make the drug to antibody ratio (DAR) sub-optimally high. Furthermore, many lysines are located in critical antigen binding sites of CDR region and drug conjugation may lead to a reduction in antibody affinity. On the other hand, while thiol mediated conjugation mainly targets the eight cysteines involved in hinge disulfide bonds, it is still difficult to predict and identify which four of eight cysteines are consistently conjugated among the different preparations.

Recently, genetic engineering of free cysteine residues has enabled site-specific conjugation with thiol-based chemistries. The site-specific ADCs have homogeneous profiles and well-defined conjugation sites, and showed potent in vitro cytotoxicity and strong in vivo antitumor activity.

WO 2013/093809 discloses engineered antibody constant regions (Fc, Cγ, Cκ, Cλ), or a fragment thereof, that comprise amino acid substitutions at specific sites to introduce a cysteine residue for conjugation. A number of Cys-mutation sites in IgG heavy chain and lambda/kappa light chain constant regions are disclosed.

The success of using introduced Cys residues for site-specific conjugation relies on the ability to select sites in which Cys-substitution does not alter protein structure or function. Further, using different conjugation sites can result in different characteristics, such as biological stability of the ADC. Therefore, a site-specific conjugation strategy which generates an ADC with a defined conjugation site and desired ADC characteristics would be highly useful.

SUMMARY OF THE INVENTION

The invention relates to polypeptides, antibodies, and antigen-binding fragments thereof, that comprise an engineered cysteine for site-specific conjugation.

Those skilled in the art will recognize, or be able to ascertain using no more than routine experimentation, many equivalents to the specific embodiments of the invention described herein. Such equivalents are intended to be encompassed by the following embodiments (E).

E1. An antibody drug conjugate of formula Ab-(L-D), wherein:
(a) Ab is an antibody or an antigen binding fragment comprising an antibody heavy chain constant domain containing an engineered cysteine residue at position 334, according to the numbering of the Eu index of Kabat; and
(b) L-D is a linker-drug moiety that is attached to the Ab via the engineered cysteine residue, wherein L is a linker and D is a drug.

E2. An antibody drug conjugate of formula Ab-(L-D), wherein:
(a) Ab is an antibody or an antigen binding fragment comprising an antibody heavy chain constant domain containing an engineered cysteine residue at a position corresponding to residue 104 of SEQ ID NO: 25, when said constant domain is aligned with SEQ ID NO:25; and
(b) L-D is a linker-drug moiety that is attached to the Ab via the engineered cysteine residue, wherein L is a linker and D is a drug.

E3. An antibody drug conjugate of formula Ab-(L-D), wherein:
(a) Ab is an antibody or an antigen binding fragment comprising an antibody heavy chain constant domain containing an engineered cysteine residue at position 392, according to the numbering of the EU index of Kabat; and
(b) L-D is a linker-drug moiety that is attached to the Ab via the engineered cysteine residue, wherein L is a linker and D is a drug.

E4. An antibody drug conjugate of formula Ab-(L-D), wherein:
(a) Ab is an antibody or an antigen binding fragment comprising an antibody heavy chain constant domain containing an engineered cysteine residue at a position corresponding to residue 162 of SEQ ID NO: 26, when said constant domain is aligned with SEQ ID NO: 26; and
(b) L-D is a linker-drug moiety that is attached to the Ab via the engineered cysteine residue, wherein L is a linker and D is a drug.

E5. The antibody drug conjugate of any one of E1-E4, wherein said constant domain comprises an IgG, IgA, IgD, IgE, or IgM heavy chain domain.

E6. The antibody drug conjugate of E1-E5, wherein said constant domain comprises an $IgG_1$, $IgG_2$, $IgG_3$, or $IgG_4$ heavy chain domain.

E7. The antibody drug conjugate of E1-E5, wherein said constant domain comprises an $IgA_1$ or $IgA_2$ heavy chain domain.

E8. The antibody drug conjugate of any one of E1-E7, wherein said constant domain is a human antibody constant domain.

E9. The antibody drug conjugate of any one of E1-E8, wherein said constant domain further comprises one or more engineered cysteine residues at a position selected from the group consisting of: 118, 246, 249, 265, 267, 270, 276, 278, 283, 290, 292, 293, 294, 300, 302, 303, 314, 315, 318, 320, 332, 333, 334, 336, 345, 347, 354, 355, 358, 360, 362, 370, 373, 375, 376, 378, 380, 382, 386, 388, 390, 392, 393, 401, 404, 411, 413, 414, 416, 418, 419, 421, 428, 431, 432, 437, 438, 439, 443, and 444 according to the numbering of the Eu index of Kabat.

E10. The antibody drug conjugate of any one of E1-E9, wherein said constant domain further comprises one or more engineered cysteine residues at a position selected from the group consisting of: 290, 334, 347, and 392 according to the numbering of the Eu index of Kabat.

E11. The antibody drug conjugate of any one of E1-E10, wherein said constant domain comprises an engineered cysteine residue at position 334 and at position 392, according to the numbering of the Eu index of Kabat.

E12. The antibody drug conjugate of E9-E11, wherein said constant domain comprises an IgG heavy chain $CH_2$ domain and an IgG heavy chain $CH_3$ domain.

E13. The antibody drug conjugate of any one of E1-E12, wherein said Ab further comprises an antibody light chain constant region comprising (i) an engineered cysteine residue at position 110, 111, 125, 149, 155, 158, 161, 183, 185, 188, 189, 191, 197, 205, 206, 207, 208, 210, or any combination thereof, according to the numbering of Kabat; (ii) an engineered cysteine residue at a position corresponding to residue 4, 42, 76, 81, 100, 103, or any combination thereof, of SEQ ID NO:30, when said constant domain is aligned with SEQ ID NO:30 (kappa light chain); or (iii) an engineered cysteine residue at a position corresponding to residue 4, 5, 19, 43, 49, 52, 55, 78, 81, 82, 84, 90, 96, 97, 98, 99, 101, or any combination thereof, of SEQ ID NO:31, when said constant domain is aligned with SEQ ID NO:31 (lambda light chain).

E14. The antibody drug conjugate of E13, wherein said light chain constant region comprises (i) an engineered cysteine residue at position 183, according to the numbering of Kabat; or (ii) an engineered cysteine residue at a position corresponding to residue 76 of SEQ ID NO:30, when said constant domain is aligned with SEQ ID NO:30.

E15. The antibody drug conjugate of E13 or E14, wherein said light chain constant region comprises a kappa light chain constant domain (CLκ).

E16. The antibody drug conjugate of E13 or E14, wherein said light chain constant region comprises a lambda light chain constant domain (CLλ).

E17. The antibody drug conjugate of any one of E1-E16, wherein said antibody or antigen binding fragment thereof is selected from the group consisting of a chimeric antibody, a human antibody, and a humanized antibody.

E18. The antibody drug conjugate of any one of E1-E17, wherein said antibody or antigen binding fragment binds to an antigen disclosed in paragraphs [54]-[58].

E19. The antibody drug conjugate of any one of E1-E17, wherein said antibody or antigen binding fragment binds to an antigen selected from the group of: HER2, HER3, HER4, CD22, and CD33.

E20. The antibody drug conjugate of any one of E1-E19, wherein said antibody or antigen binding fragment binds to CD33.

E21. The antibody drug conjugate of any one of E1-E20, wherein said antibody comprises
(i) a heavy chain variable region (VH) that comprises:
  (a) a VH complementarity determining region one (CDR-H1) comprising the amino acid sequence of SEQ ID NO: 5 or 6,
  (b) a VH CDR-H2 comprising the amino acid sequence of SEQ ID NO: 9 or 10,
  (c) a VH CDR-H3 comprising the amino acid sequence of SEQ ID NO: 13; and
(ii) a light chain variable region (VL) that comprises:
  (a) a VL complementarity determining region one (CDR-L1) comprising the amino acid sequence of SEQ ID NO: 17,
  (b) a VL CDR-L2 comprising the amino acid sequence of SEQ ID NO: 19; and
  (c) a VL CDR-L3 comprising the amino acid sequence of SEQ ID NO: 21.

E22. The antibody drug conjugate of any one of E1-E21, comprising (i) a VH that comprises an amino acid sequence at least 90% identical to SEQ ID NO: 1; and (ii) a VL that comprises an amino acid sequence at least 90% identical to SEQ ID NO: 3.

E23. The antibody drug conjugate of any one of E1-E22, comprising (i) a heavy chain that comprises an amino acid sequence of SEQ ID NOs: 32, 33, or 34 or an amino acid sequence at least 90% identical to SEQ ID NOs: 32, 33 or 34; and (ii) a light chain that comprises an amino acid sequence of SEQ ID NO: 23; or an amino acid sequence at least 90% identical to SEQ ID NO: 23.

E24. The antibody drug conjugate of any one of E1-E23, wherein the percent of drug-to-antibody ratio (DAR) loss in plasma, at 37° C. under 5% $CO_2$ at 72 hours, is no more than about 20%, no more than about 15%, no more than about 10%, no more than about 9%, no more than about 8%, no more than about 7%, no more than about 6%, no more than about 5%, no more than about 4%, no more than about 3%, no more than about 2%, or no more than about 1%.

E25. The antibody drug conjugate of any one of E1-E24, wherein the percent of drug-to-antibody ratio (DAR) loss in plasma, at 37° C. under 5% $CO_2$ at 72 hours is no more than about 15%.

E26. The antibody drug conjugate of any one of E1-E24, wherein the percent of drug-to-antibody ratio (DAR) loss in plasma, at 37° C. under 5% $CO_2$ at 72 hours is no more than about 5%.

E27. The antibody drug conjugate of any one of E1-E26, wherein the linker comprises valine-citrulline (val-cit; vc), 6-maleimidocaproyl (mc), methoxy-polyethylene glycol maleimide 6 (MalPeg6), p-aminobenzylcarbamate (PABC), dimethylaminoethanol (DMAE), maleimidopropanoyl (MP), hydrolyzed Peg-maleimides, m(H20)c, m(H20)cvc, alanine-phenylalanine (ala-phe), p-aminobenzyloxycarbonyl (PAB), N-Succinimidyl 4-(2-pyridylthio) pentanoate (SPP), N-succinimidyl 4-(N-maleimidomethyl) cyclohexane-1carboxylate (SMCC), N-Succinimidyl (4-iodoacetyl) aminobenzoate (SIAB), or 6-maleimidocaproyl-valine-citrulline-p-aminobenzyloxycarbonyl (MC-vc-PAB) or a combination thereof.

E28. The antibody drug conjugate of any one of E1-E27, wherein the linker comprises a combination of MalPeg6, vc, PABC, and DMAE.

E29. The antibody drug conjugate of any one of E1-E28, wherein the linker comprises MalPeg6-vc-PABC-DMAE.

E30. The antibody drug conjugate of any one of E1-E29, wherein the drug is selected from the group consisting of: a cytotoxic agent, a cytostatic agent, a chemotherapeutic agent, a toxin, a radionuclide, a DNA, an RNA, an siRNA, a microRNA, a peptide nucleic acid, a non-natural amino acid, a peptide, an enzyme, a fluorescent tag, biotin, and any combination thereof.

E31. The antibody drug conjugate of any one of E1-E30, wherein the drug is a DNA alkylating agent.

E32. The antibody drug conjugate of any one of E1-E31, wherein the drug is a DNA minor groove binding alkylating agent.

E33. The antibody drug conjugate of any one of E1-E32, wherein the drug is a CPI dimer, a CTI dimer, or a CBI dimer.

E34. The antibody drug conjugate of any one of E1-E33, wherein the drug is a CPI dimer.

E35. The antibody drug conjugate of any one of E1-E34, wherein the drug is a CPI dimer and the CPI dimer is a compound of the formula:

$$F_1\text{-}DL\text{-}F_2 \quad \text{(Formula I)}$$

or a pharmaceutically acceptable salt or solvate thereof, wherein:

$F_1$ is a CPI monomer comprising:

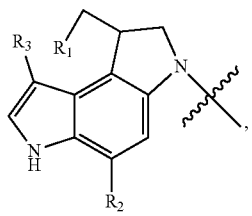

wherein $R_1$ is H, —OH, —O-acyl, azido, halo (F, Cl, Br, I), sulfonate (—OSO$_2$R), cyanate, thiocyanate, isocyanate, or thioisocyanate;

$R_2$ is $R_2$ is H, —OH, —SH, NHR, acyl, acetate, phosphate, glucuronide, or galactoside;

$R_3$ is H, —C$_1$-C$_5$ substituted or unsubstituted alkyl, substituted or unsubstituted phenyl, —C(O)OR, —C(O)SR, —C(O)NHN(R)$_2$, or —C(O)N(R)$_2$;

$F_2$ is a CPI monomer comprising:

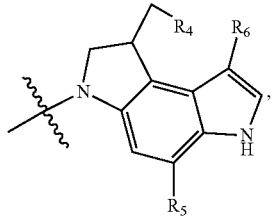

wherein $R_4$ is H, —OH, —O-acyl, azido, halo (F, Cl, Br, I), sulfonate, cyanate, thiocyanate, isocyanate, or thioisocyanate;

$R_5$ is H, —OH, —SH, NHR, acyl, acetate, phosphate, glucuronide, or galactoside;

$R_6$ is H, —C$_1$-C$_5$ substituted or unsubstituted alkyl, substituted or unsubstituted phenyl, —C(O)OR, —C(O)SR, —C(O)NHN(R)$_2$, or —C(O)N(R)$_2$;

R is selected from the group consisting of H, —C$_1$-C$_{20}$ alkyl, —C$_2$-C$_6$ alkenyl, —C$_2$-C$_6$ alkynyl, halo, hydroxyl, alkoxy, —NH$_2$, —NH(C$_1$-C$_8$ alkyl), —N(C$_1$-C$_8$ alkyl)$_2$, —NO$_2$, —C$_6$-C$_{14}$ aryl and —C$_6$-C$_{14}$ heteroaryl, wherein two or more R optionally join to form a ring or rings, and wherein said —C$_6$-C$_{14}$ aryl and —C$_6$-C$_{14}$ heteroaryl are optionally substituted with 1 to 5 substituents independently from —C$_1$-C$_{10}$ alkyl, —C$_1$-C$_{10}$ alkoxy, halo, —C$_1$-C$_{10}$ alkylthio, trifluoromethyl, —NH$_2$, —NH(C$_1$-C$_8$ alkyl), —N(C$_1$-C$_8$ alkyl)$_2$, —C$_1$-C$_{10}$ alkyl-N(C$_1$-C$_8$ alkyl)$_2$, —C$_1$-C$_3$ alkylthio, —NO$_2$, or —C$_1$-C$_{10}$ heterocyclyl for each ring system in which R appears;

DL is a dimer-linker comprising:

$$R_7\text{—}X\text{—}R_8, \text{ wherein}$$

$R_7$ and $R_8$ are each independently selected from a direct bond, carbonyl, or a carbonyl acyl group bonded to $F_1$ or $F_2$ at the free nitrogen atom of the saturated five-membered ring; and X is a —C$_1$-C$_{20}$ substituted or unsubstituted alkyl chain, a —C$_1$-C$_{20}$ substituted or unsubstituted fused or bridged cycloalkyl, or a substituted or unsubstituted saturated or aromatic heterocyclic ring comprised of from 3-20 atoms selected from C, N, O, and/or S.

E36. The antibody drug conjugate of E35, wherein the CPI dimer is:

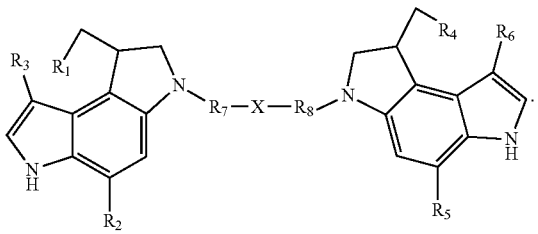

E37. The antibody drug conjugate of E36, wherein $R_1$ is a halo (F, Cl, Br, I) or sulfonate (—OSO$_2$R), $R_2$ is —OH, phosphate, glucuronide or galactoside, $R_3$ is a C$_1$-C$_5$ unsubstituted or substituted alkyl, $R_4$ is a halo (F, Cl, Br, I) or suphonate (—OSO$_2$R), $R_5$ is —OH, phosphate, glucuronide or galactoside, and $R_6$ is a C$_1$-C$_5$ unsubstituted or substituted alkyl.

E38. The antibody drug conjugate of E37, wherein $R_1$ is a halo (F, Cl, Br, I), $R_2$ is—OH or phosphate, $R_3$ is a C$_3$ or a C$_5$ unsubstituted or substituted alkyl, $R_4$ is a halo (F, Cl, Br, I), $R_5$ is —OH or phosphate, and $R_6$ is a C$_3$ or a C$_5$ unsubstituted or substituted alkyl.

E39. The antibody drug conjugate of E38, wherein the CPI dimer is selected from the group consisting of:

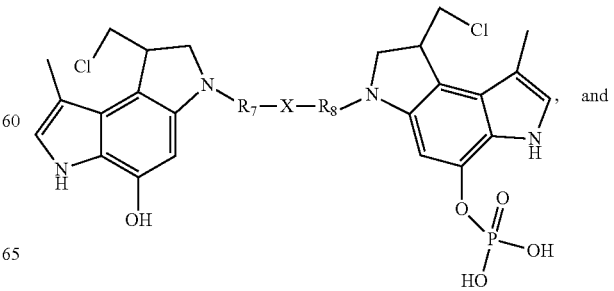

, and

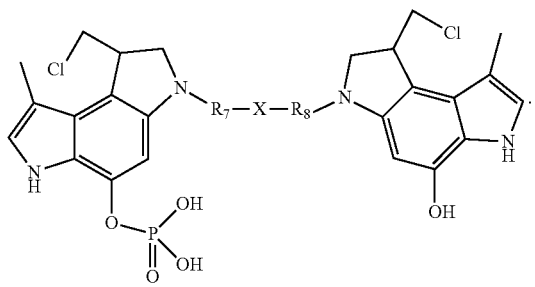

E40. The antibody drug conjugate of any one of E35-E39, wherein $R_7$ and $R_8$ each independently is a carbonyl, and X is a —$C_1$-$C_{20}$ substituted or unsubstituted alkyl chain, a —$C_1$-$C_{20}$ substituted or unsubstituted fused or bridged cycloalkyl, or a substituted or unsubstituted saturated or aromatic heterocyclic ring comprised of from 3-20 atoms selected from C, N, O, and/or S.

E41. The antibody drug conjugate of E40, wherein $R_7$ and $R_8$ each independently is a carbonyl, and X is a —$C_5$-$C_{10}$ substituted or unsubstituted alkyl chain, a —$C_5$-$C_{10}$ substituted or unsubstituted fused or bridged cycloalkyl, or a substituted or unsubstituted saturated or aromatic heterocyclic ring comprised of from 5-10 atoms selected from C, N, O, and/or S.

E42. The antibody drug conjugate of E41, wherein $R_7$ and $R_8$ each independently is a carbonyl, and X is a $C_5$ or a $C_8$ substituted or unsubstituted alkyl chain, a $C_5$ or a $C_8$ substituted or unsubstituted fused or bridged cycloalkyl, or a substituted or unsubstituted saturated or aromatic heterocyclic ring comprised of 5 or 8 atoms selected from C, N, O, and/or S.

E43. The antibody drug conjugate of any one of E1-E42, wherein the drug is a CPI dimer and is selected from the group consisting of:

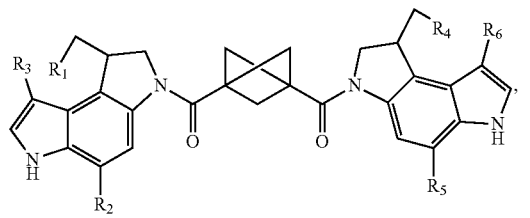

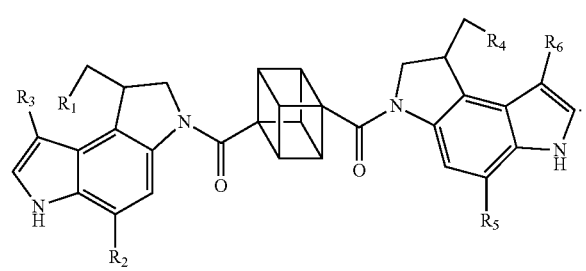

E44. The antibody drug conjugate of any one of E1-E43, wherein the drug is a CPI dimer and is selected from the group consisting of:

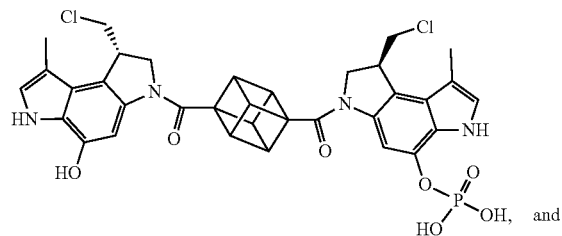

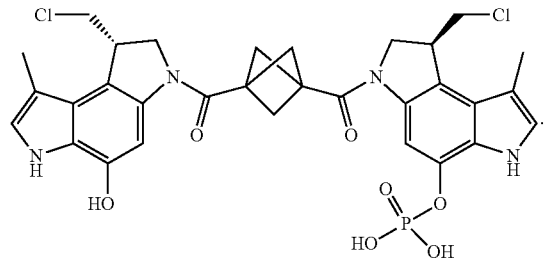

E45. The antibody drug conjugate of any one of E1-E44, wherein the linker comprises MalPeg6-vc-PABC-DMAE, and wherein D is a CPI dimer selected from the group consisting of:

E46. The antibody drug conjugate of E33, wherein the drug is a CTI dimer, and the CTI dimer is selected from the group consisting of:

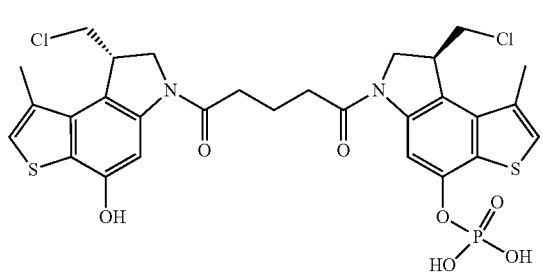

-continued

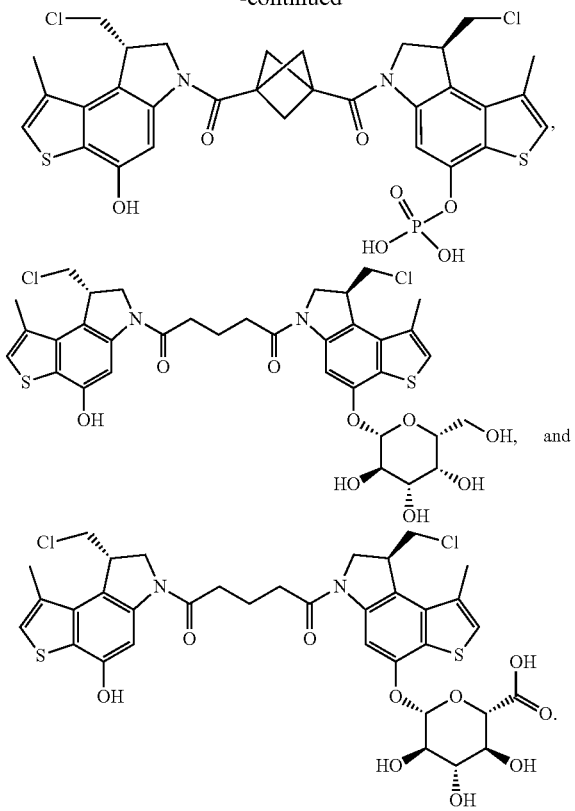

E47. The antibody drug conjugate of E33, wherein the drug is a CBI dimer and the CBI dimer is selected from the group consisting of:

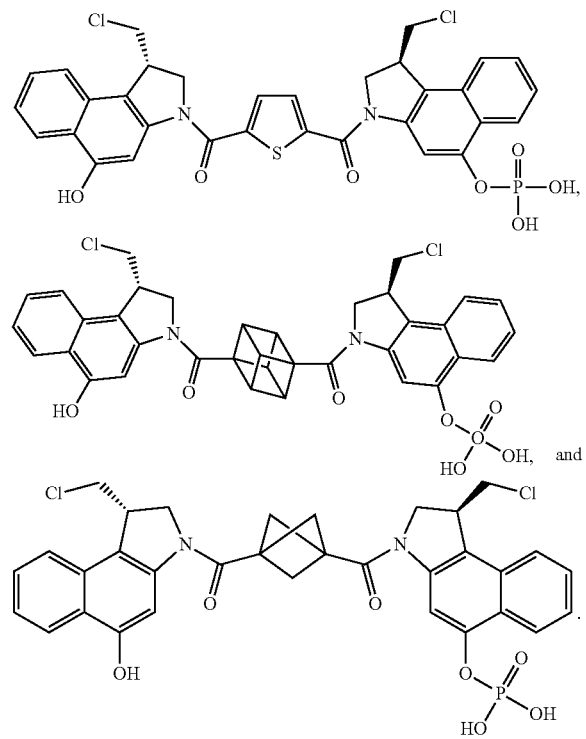

E48. The antibody drug conjugate of E47, wherein the CBI dimer is:

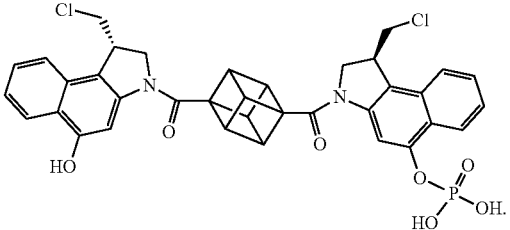 [SMILES: O=C(N1C[C@@H](CCl)c2c1cc(O)c1ccccc21)C12C3C4C1C1C2C3C41C(=O)N1C[C@@H](CCl)c2c1cc(OP(=O)(O)O)c1ccccc21]

E49. The antibody drug conjugate of any one of E1-E48, wherein L-D is selected from the group consisting of:
(i) N-[1-(2,5-dioxo-2,5-dihydro-1H-pyrrol-1-yl)-21-oxo-3,6,9,12,15,18-hexaoxahenicosan-21-yl]-L-valyl-$N^5$-carbamoyl-N-[4-({[(2-{[({(1S)-1-(chloromethyl)-3-[(5-{[(1S)-1-(chloromethyl)-5-(phosphonooxy)-1,2-dihydro-3H-benzo[e]indol-3-yl]carbonyl}thiophen-2-yl)carbonyl]-2,3-dihydro-1H-benzo[e]indol-5-yl}oxy)carbonyl](methyl)amino}ethyl)(methyl)carbamoyl]oxy}methyl)phenyl]-L-ornithinamide;
(ii) N-[1-(2,5-dioxo-2,5-dihydro-1H-pyrrol-1-yl)-21-oxo-3,6,9,12,15,18-hexaoxahenicosan-21-yl]-L-valyl-$N^5$-carbamoyl-N-[4-({[(2-{[({(1S)-1-(chloromethyl)-3-[(5-{[(1S)-1-(chloromethyl)-5-(phosphonooxy)-1,2-dihydro-3H-benzo[e]indol-3-yl]carbonyl}thiophen-2-yl)carbonyl]-2,3-dihydro-1H-benzo[e]indol-5-yl}oxy)carbonyl](ethyl)amino}ethyl) (ethyl)carbamoyl]oxy}methyl) phenyl]-L-ornithinamide;
(iii) N-[1-(2,5-dioxo-2,5-dihydro-1H-pyrrol-1-yl)-21-oxo-3,6,9,12,15,18-hexaoxahenicosan-21-yl]-L-valyl-$N^5$-carbamoyl-N-(4-{7-[({(1S)-1-(chloromethyl)-3-[(5-{[(1S)-1-(chloromethyl)-5-(phosphonooxy)-1,2-dihydro-3H-benzo[e]indol-3-yl]carbonyl}thiophen-2-yl)carbonyl]-2,3-dihydro-1H-benzo[e]indol-5-yl}oxy)carbonyl]-4-(2-methoxyethyl)-3-oxo-2,10-dioxa-4,7-diazaundec-1-yl}phenyl)-L-ornithinamide;
(iv) N-[1-(2,5-dioxo-2,5-dihydro-1H-pyrrol-1-yl)-21-oxo-3,6,9,12,15,18-hexaoxahenicosan-21-yl]-L-valyl-N-(4-{7-[({(1S)-1-(chloromethyl)-3-[(5-{[(1S)-1-(chloromethyl)-5-(phosphonooxy)-1,2-dihydro-3H-benzo[e]indol-3-yl]carbonyl}thiophen-2-yl)carbonyl]-2,3-dihydro-1H-benzo[e]indol-5-yl}oxy)carbonyl]-4-(2-methoxyethyl)-3-oxo-2,10-dioxa-4,7-diazaundec-1-yl}phenyl)-L-alaninamide;
(v) N-[1-(2,5-dioxo-2,5-dihydro-1H-pyrrol-1-yl)-21-oxo-3,6,9,12,15,18-hexaoxahenicosan-21-yl]-L-valyl-$N^5$-carbamoyl-N-[4-({[(2-{[({(1S)-1-(chloromethyl)-3-[(4-{[(1S)-1-(chloromethyl)-5-(phosphonooxy)-1,2-dihydro-3H-benzo[e]indol-3-yl]carbonyl}pentacyclo[4.2.0.0$^{2,5}$.0$^{3,8}$.0$^{4,7}$]oct-1-yl)carbonyl]-2,3-dihydro-1H-benzo[e]indol-5-yl}oxy)carbonyl](methyl)amino}ethyl)(methyl)carbamoyl]oxy}methyl)phenyl]-L-ornithinamide;
(vi) N-[1-(2,5-dioxo-2,5-dihydro-1H-pyrrol-1-yl)-21-oxo-3,6,9,12,15,18-hexaoxahenicosan-21-yl]-L-valyl-$N^5$-carbamoyl-N-[4-({[(2-{[({(1S)-1-(chloromethyl)-3-[(3-{[(1S)-1-(chloromethyl)-5-(phosphonooxy)-1,2-dihydro-3H-benzo[e]indol-3-yl]carbonyl}bicyclo[1.1.1]pent-1-yl)carbonyl]-2,3-dihydro-1H-benzo[e]indol-5-yl}oxy)carbonyl](methyl)amino}ethyl)(methyl)carbamoyl]oxy}methyl)phenyl]-L-ornithinamide;
(vii) N-[1-(2,5-dioxo-2,5-dihydro-1H-pyrrol-1-yl)-21-oxo-3,6,9,12,15,18-hexaoxahenicosan-21-yl]-L-valyl-$N^5$-carbamoyl-N-[4-({[(2-{[({(8S)-8-(chloromethyl)-6-[(3-{[(1S)-1-(chloromethyl)-8-methyl-5-(phosphonooxy)-1,6-dihydropyrrolo[3,2-e]indol-3(2H)-yl]carbonyl}bicyclo[1.1.1]pent-1-yl)carbonyl]-1-methyl-3,6,7,8-tetrahydropyrrolo[3,2-e]indol-4-yl}oxy)carbonyl](methyl)amino}ethyl)(methyl)carbamoyl]oxy}methyl)phenyl]-L-ornithinamide;

(viii) N-[1-(2,5-dioxo-2,5-dihydro-1H-pyrrol-1-yl)-21-oxo-3,6,9,12,15,18-hexaoxahenicosan-21-yl]-L-valyl-$N^5$-carbamoyl-N-[4-({[(2-{[({(8S)-8-(chloromethyl)-6-[(3-{[(8S)-8-(chloromethyl)-1-methyl-4-(phosphonooxy)-7,8-dihydro-6H-thieno[3,2-e]indol-6-yl]carbonyl}bicyclo[1.1.1]pent-1-yl)carbonyl]-1-methyl-7,8-dihydro-6H-thieno[3,2-e]indol-4 yl}oxy)carbonyl](methyl)amino}ethyl)(methyl)carbamoyl]oxy}methyl)-phenyl]-L-ornithinamide;

(ix) N-[1-(2,5-dioxo-2,5-dihydro-1H-pyrrol-1-yl)-21-oxo-3,6,9,12,15,18-hexaoxahenicosan-21-yl]-L-valyl-$N^5$-carbamoyl-N-[4-({[{2-[({[(8S)-8-(chloromethyl)-6-{5-[(8S)-8-(chloromethyl)-1-methyl-4-(phosphonooxy)-7,8-dihydro-6H-thieno[3,2-e]indol-6-yl]-5-oxopentanoyl}-1-methyl-7,8-dihydro-6H-thieno[3,2-e]indol-4-yl]oxy}carbonyl)(methyl)amino]ethyl}(methyl)carbamoyl]oxy}methyl)phenyl]-L-ornithinamide; and (x) N-[1-(2,5-dioxo-2,5-dihydro-1H-pyrrol-1-yl)-21-oxo-3,6,9,12,15,18-hexaoxahenicosan-21-yl]-L-valyl-$N^5$-carbamoyl-N-[4-({[{2-[({[(8S)-8-(chloromethyl)-6-{(8S)-8-(chloromethyl)-4-(beta-D-glucopyranuronosyloxy)-1-methyl-7,8-dihydro-6H-thieno[3,2-e]indol-6-yl]-5-oxopentanoyl}-1-methyl-7,8-dihydro-6H-thieno[3,2-e]indol-4-yl]oxy}carbonyl)(methyl)amino]ethyl}(methyl)carbamoyl]oxy}methyl) phenyl]-L-ornithinamide.

E50. The antibody drug conjugate of E49, wherein said L-D comprises N-[1-(2,5-dioxo-2,5-dihydro-1H-pyrrol-1-yl)-21-oxo-3,6,9,12,15,18-hexaoxahenicosan-21-yl]-L-valyl-$N^5$-carbamoyl-N-[4-({[(2-{[({(8S)-8-(chloromethyl)-6-[(3-{[(1S)-1-(chloromethyl)-8-methyl-5-(phosphonooxy)-1,6-dihydropyrrolo[3,2-e]indol-3(2H)-yl]carbonyl}bicyclo[1.1.1]pent-1-yl)carbonyl]-1-methyl-3,6,7,8-tetrahydropyrrolo[3,2-e]indol-4-yl}oxy)carbonyl](methyl)amino}ethyl)(methyl)carbamoyl]oxy}methyl)phenyl]-L-ornithinamide.

E51. The antibody drug conjugate of any one of E1-E50, wherein drug-to-antibody ratio (DAR) at position 334 and/or at position 392 in plasma, at 37° C. at 72 hours is at least 1.6, at least 1.7, at least 1.8, at least 1.9 or at least 2.

E52. The antibody drug conjugate of any one of E1-E51, wherein said antibody drug conjugate has a melting transition temperature greater than at least 60° C., at least 65° C., at least 70° C., at least 75° C., at least 80° C., or at least 85° C.

E53. The antibody drug conjugate of E52, wherein said antibody drug conjugate has a melting transition temperature greater than about 65° C.

E54. The antibody drug conjugate of any one of E1-E53, wherein said antibody drug conjugate has an IC50 value of no more than about 180 ng/ml, no more than about 160 ng/ml, no more than about 150 ng/ml, no more than about 100 ng/ml, no more than about 50 ng/ml, no more than about 25 ng/ml, no more than about 20 ng/ml, no more than about 15 ng/ml, no more than about 10 ng/ml, no more than about 5 ng/ml, or no more than about 2.5 ng/ml.

E55. The antibody drug conjugate of E54, wherein said antibody drug conjugate has an IC50 value of no more than about 10 ng/ml, no more than about 5 ng/ml, or no more than about 2.5 ng/ml.

E56. The antibody drug conjugate of E54 or E55, wherein said antibody or antigen binding fragment thereof binds to CD33 and said IC50 values are determined in CD33 expressing cells.

E57. The antibody drug conjugate of any one of E1-E56, wherein said antibody drug conjugate reduces mean tumor volume to less than about 150 mm³, less than about 125 mm³, less than about 100 mm³, less than about 75 mm³ by about day 4, about day 6, about day 8, about day 10, about day 12, about day 14, about day 16, or about day 18 of treatment with said conjugate in a HL60 AML tumor xenograft model.

E58. The antibody drug conjugate of any one of E1-E56, wherein said antibody drug conjugate reduces mean tumor volume by at least 5%, 10%, 15%, 20%, 25%, 30%, 35%, 40%, 45%, 50%, 55%, 60%, 65%, 70%, 75%, 80%, 85%, 90%, 95%, or 100% as compared to mean tumor volume in untreated controls in a HL60 AML tumor xenograft model.

E59. The antibody drug conjugate of any one of E1-E56, wherein said antibody drug conjugate reduces mean tumor volume to less than about 150 mm³, less than about 125 mm³, less than about 100 mm³, less than about 75 mm³ by about day 4, about day 6, about day 8, about day 10, about day 12, about day 14, about day 16, or about day 18 of treatment with said conjugate in a TF1 AML tumor xenograft model.

E60. The antibody drug conjugate of any one of E1-E56, wherein said antibody drug conjugate reduces mean tumor volume by at least 5%, 10%, 15%, 20%, 25%, 30%, 35%, 40%, 45%, 50%, 55%, 60%, 65%, 70%, 75%, 80%, 85%, 90%, 95%, or 100% as compared to mean tumor volume in untreated controls in a TF1 AML tumor xenograft model.

E61. The antibody drug conjugate of any one of E1-E56, wherein said antibody drug conjugate reduces mean tumor volume to less than about 150 mm³, less than about 125 mm³, less than about 100 mm³, less than about 75 mm³ by about day 4, about day 6, about day 8, about day 10, about day 12, about day 14, about day 16, or about day 18 of treatment with said conjugate in a Her2 expressing tumor xenograft model.

E62. The antibody drug conjugate of any one of E1-E56, wherein said antibody drug conjugate reduces mean tumor volume by at least 5%, 10%, 15%, 20%, 25%, 30%, 35%, 40%, 45%, 50%, 55%, 60%, 65%, 70%, 75%, 80%, 85%, 90%, 95%, or 100% as compared to mean tumor volume in untreated controls in a Her2 expressing tumor xenograft model.

E63. A pharmaceutical composition comprising the antibody drug conjugate of any one of E1-E62; and a pharmaceutically acceptable carrier.

E64. A method of treating cancer, an autoimmune disease, an inflammatory disease, or an infectious disease, comprising administering to a subject in need thereof a therapeutically effective amount of the antibody drug conjugate of any one of E1-E62, or the composition of E63.

E65. The antibody drug conjugate of any one of E1-E62, or the composition of E63, for use in treating cancer, an autoimmune disease, an inflammatory disease, or an infectious disease.

E66. Use of the antibody drug conjugate of any one of E1-E62, or the composition of E63, for treating cancer, an autoimmune disease, an inflammatory disease, or an infectious disease.

E67. Use of the antibody drug conjugate of any one of E1-E62, or the composition of E63, in the manufacture of a medicament for treating cancer, an autoimmune disease, an inflammatory disease, or an infectious disease.

E68. A nucleic acid encoding the antibody moiety of the antibody drug conjugate of any one of E1-E62.
E69. The nucleic acid of E68, wherein the nucleic acid encodes any one of SEQ ID NO: 1-34.
E70. A host cell comprising the nucleic acid of E68 or E69.
E71. A method of producing an antibody, comprising culturing the host cell of E70 under suitable conditions for expressing said antibody, and isolating said antibody.
E72. A method of making an antibody drug conjugate comprising conjugating an antibody or an antigen binding fragment comprising an antibody heavy chain constant domain containing an engineered cysteine residue at position 334 and/or at position 392, according to the numbering of the Eu index of Kabat to a linker and a drug so as to form an antibody drug conjugate as set forth in any one of E1-E62.
E73. The method of E72, wherein the antibody is conjugated to the linker which is then conjugated to the drug.
E74. The method of E72, wherein the linker is conjugated to the drug which is then conjugated to the antibody.

DETAILED DESCRIPTION OF THE INVENTION

Figure 1:
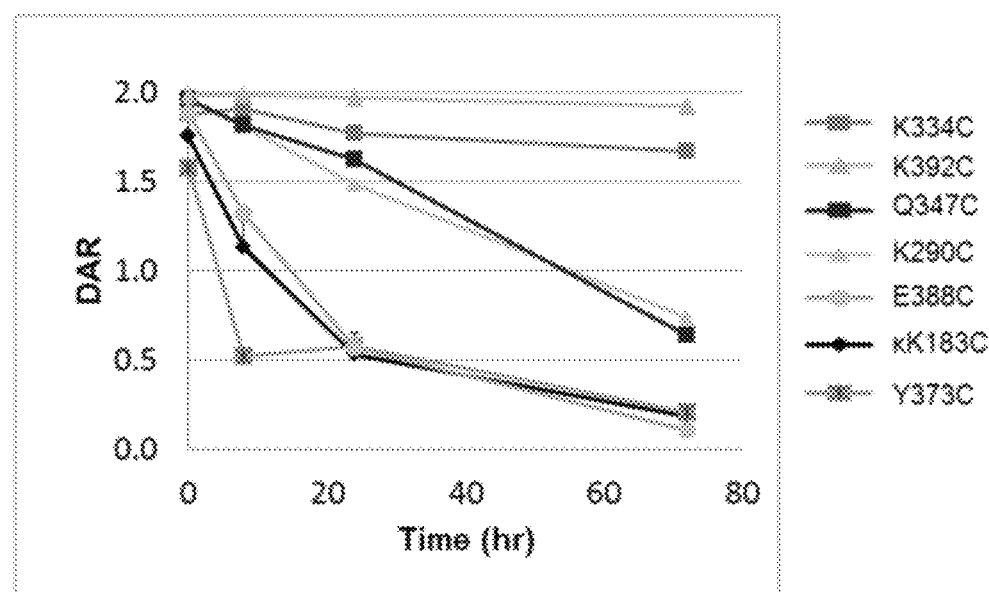
FIG. 1 depicts the loss of drug-to-antibody ratio (DAR) in plasma for CD33 ADC constructs conjugated at different sites. ADC constructs conjugated at positions 334 or 392 showed superior plasma stability as compared to the other sites.

The invention relates to polypeptides, antibodies, and antigen-binding fragments thereof, that comprise an engineered (substituted) cysteine for site-specific conjugation. In particular, it was discovered position 334 and/or position 392 in the antibody heavy chain constant region (according to the numbering of the Eu index of Kabat) can be used for site specific conjugation to make antibody drug conjugates (ADCs) with antibodies to various targets (including but not limited to CD33 and HER2). Data exemplified herein demonstrate that ADC constructs conjugated at position 334 and/or position 392 show superior in vivo properties, as compared to other conjugation sites.

A number of potential cysteine conjugation sites are known in the art (e.g., heavy chain 290 or 347, light chain 183; see WO 2017/093845). However, as shown in the Examples, the site of conjugation can have a dramatic impact on different ADC characteristics, such as biophysical properties (e.g., hydrophobicity), biological stability and ADC efficacy (e.g., ADC metabolism).

In particular, the inventors observed that the site of conjugation plays a critical role in plasma stability and in vivo efficacy. ADCs conjugated with CPI dimers at position 334 and/or at position 392 surprisingly showed superior plasma stability and in vivo efficacy as compared to ADCs conjugated at other positions, which makes these conjugation sites more advantageous for clinical use. These surprising effects could not have been predicted based on the linker payload.

In addition to favorable biological stability in vivo efficacy, engineered cysteine antibody variants (K334C and K334C/K392C double mutants) contained low levels of fragments or half molecules. These results indicate that these engineered cysteines do not impact integrity of the antibody intended for site-specific conjugation. Moreover, both K334C and K334C/K392C ADCs demonstrated excellent thermal stability post conjugation indicating that the antibody is not perturbed during conjugation.

1. Antibody-Drug Conjugates (ADCs)

ADCs comprise an antibody component conjugated to a drug payload, typically through the use of a linker. Conventional conjugation strategies for ADCs rely on randomly conjugating the drug payload to the antibody through lysines or cysteines that are endogenously found on the antibody heavy and/or light chain. Accordingly, such ADCs are a heterogeneous mixture of species showing different drug:antibody ratios (DAR). In contrast, the ADCs disclosed herein are site specific ADCs that conjugate the drug payload to the antibody at particular engineered residues on the antibody heavy and/or light chain. As such, the site specific ADCs are a homogeneous population of ADCs comprised of a species with a defined drug:antibody ratio (DAR). Thus, the site specific ADCs demonstrate uniform stoichiometry resulting in improved pharmacokinetics, biodistribution and safety profile of the conjugate. ADCs of the invention include antibodies and polypeptides of the invention conjugated to linkers and/or payloads.

The present invention provides antibody drug conjugates of the formula Ab-(L-D), wherein (a) Ab is an antibody, or antigen-binding fragment thereof, that binds an antigen, and (b) L-D is a linker-drug moiety, wherein L is a linker, and D is a drug.

Also encompassed by the present invention are antibody drug conjugates of the formula Ab-(L-D)$_p$, wherein (a) Ab is an antibody, or antigen-binding fragment thereof, that binds to CD33 or HER2, (b) L-D is a linker-drug moiety, wherein L is a linker, and D is a drug and (c) p is the number of linker/drug moieties are attached to the antibody. For site specific ADCs, p is a whole number due to the homogeneous nature of the ADC. In some embodiments, p is 4. In other embodiments, p is 3. In other embodiments, p is 2. In other embodiments, p is 1. In other embodiments, p is greater than 4.

A. Antibodies and Conjugation Sites

The polypeptides and antibodies of the invention are conjugated to the payload in a site specific manner. To accommodate this type of conjugation, the constant domain is modified to provide for a reactive cysteine residue engineered at one or more specific sites (sometimes referred to as "Cys mutants").

In general, the regions of an antibody heavy or light chain are defined as "constant" (C) region or "variable" (V) regions, based on the relative lack of sequence variation within the regions of various class members. A constant region of an antibody may refer to the constant region of the antibody light chain or the constant region of the antibody heavy chain, either alone or in combination. The constant domains are not involved directly in binding an antibody to an antigen, but exhibit various effector functions, such as Fc receptor (FcR) binding, participation of the antibody in antibody-dependent cellular toxicity (ADCC), opsonization, initiation of complement dependent cytotoxicity, and mast cell degranulation.

The constant and variable regions of an antibody heavy and light chains are folded into domains. Constant region on the light chain of an immunoglobulin is generally referred to as "CL domain." Constant domains on the heavy chain (e.g. hinge, CH1, CH2 or CH3 domains) are referred to as "CH domains." The constant regions of the polypeptide or antibody (or fragment thereof) of the invention may be derived from constant regions of any one of IgA, IgD, IgE, IgG, IgM, or any isotypes thereof as well as subclasses (e.g., $IgG_1$, $IgG_2$, $IgG_3$, $IgG_4$, $IgA_1$ and $IgA_2$) and mutated versions thereof.

CH1 domain includes the first (most amino terminal) constant region domain of an immunoglobulin heavy chain that extends, e.g., from about positions 118-215 according to the numbering of the Eu index of Kabat. The CH1 domain is adjacent to the VH domain and amino terminal to the hinge region of an immunoglobulin heavy chain molecule, and does not form a part of the Fc region of an immunoglobulin heavy chain.

The hinge region includes the portion of a heavy chain molecule that joins the CH1 domain to the CH2 domain. This hinge region comprises approximately 25 residues and is flexible, thus allowing the two N-terminal antigen binding regions to move independently. Hinge regions can be subdivided into three distinct domains: upper, middle, and lower hinge domains.

CH2 domain includes the portion of a heavy chain immunoglobulin molecule that extends, e.g., from about positions 231-340 according to the numbering of the Eu index of Kabat. The CH2 domain is unique in that it is not closely paired with another domain. Rather, two N-linked branched carbohydrate chains are interposed between the two CH2 domains of an intact native IgG molecule. In certain embodiments, the polypeptide or antibody (or fragment thereof) of the invention comprises a CH2 domain derived from an IgG molecule, such as IgG1, IgG2, IgG3, or IgG4. In certain embodiments, the IgG is a human IgG.

CH3 domain includes the portion of a heavy chain immunoglobulin molecule that extends approximately 110 residues from N-terminus of the CH2 domain, e.g., from about positions 341-447 according to the numbering of the EU index of Kabat. The CH3 domain typically forms the C-terminal portion of the antibody. In some immunoglobulins, however, additional domains may extend from CH3 domain to form the C-terminal portion of the molecule (e.g. the CH4 domain in the μ chain of IgM and the s chain of IgE). In certain embodiments, the polypeptide or antibody (or fragment thereof) of the invention comprises a CH3 domain derived from an IgG molecule, such as IgG1, IgG2, IgG3, or IgG4. In certain embodiments, the IgG is a human IgG.

CL domain includes the constant region domain of an immunoglobulin light chain that extends, e.g. from about positions 108-214 according to the numbering of the EU index of Kabat. The CL domain is adjacent to the VL domain. In certain embodiments, the polypeptide or antibody (or fragment thereof) of the invention comprises a kappa light chain constant domain (CLκ). In certain embodiments, the polypeptide or antibody (or fragment thereof) of the invention comprises a lambda light chain constant domain (CLλ). CLκ has known polymorphic loci CLκ-V/A45 and CLκ-L/V83 (using Kabat numbering) thus allowing for polymorphisms Km(1): CLκ-V45/L83; Km(1,2): CLκ-A45/L83; and Km(3): CLκ-A45/V83. Polypeptides, antibodies and ADCs of the invention can have antibody components with any of these light chain constant regions.

The Fc region generally comprises a CH2 domain and a CH3 domain. Although the boundaries of the Fc region of an immunoglobulin heavy chain might vary, the human IgG heavy chain Fc region is usually defined to stretch from an amino acid residue at position Cys226, or from Pro230 (according to the numbering of the Eu index of Kabat), to the carboxyl-terminus thereof. A Fc region of the invention may be a native sequence Fc region or a variant Fc region.

In one aspect, the invention provides a polypeptide comprising an antibody heavy chain constant domain that comprises an engineered cysteine residue at position 334, according to the numbering of the Eu index of Kabat. As disclosed and exemplified herein, conjugation at position 334 provided surprisingly desirable plasma stability and in vivo efficacy.

In one aspect, the invention provides a polypeptide comprising an antibody heavy chain constant domain that comprises an engineered cysteine residue at position 392, according to the numbering of the Eu index of Kabat. As disclosed and exemplified herein, conjugation at position 392 provided surprisingly desirable plasma stability and in vivo efficacy.

In some aspects, the invention provides a polypeptide comprising an antibody heavy chain constant domain that comprises engineered cysteine residues at position 334 and position 392, according to the numbering of the Eu index of Kabat. As disclosed and exemplified herein, conjugation at positions 334 and 392 provided surprisingly desirable plasma stability and in vivo efficacy.

Additional cysteine substitution may also be introduced, such as at positions 118, 246, 249, 265, 267, 270, 276, 278, 283, 290, 292, 293, 294, 300, 302, 303, 314, 315, 318, 320, 332, 333, 336, 345, 347, 354, 355, 358, 360, 362, 370, 373, 375, 376, 378, 380, 382, 386, 388, 390, 393, 401, 404, 411, 413, 414, 416, 418, 419, 421, 428, 431, 432, 437, 438, 439, 443, 444, or any combination thereof, according to the numbering of the Eu index of Kabat. In particular, additional positions 290 and 347, or any combination thereof may be used. Residue 118 is also referred to as A114, A114C, C114, or 114C in the examples because the initial publication of this site used Kabat numbering (114) instead of Eu index (118), and has since been generally referred in the art as the 114 site.

In another aspect, the invention provides an antibody or antigen binding fragment thereof comprising (a) a polypeptide disclosed herein and (b) an antibody light chain constant region comprising (i) an engineered cysteine residue at position 183, according to the numbering of the Eu index of Kabat; or (ii) an engineered cysteine residue at a position corresponding to residue 76 of SEQ ID NO:30, when said constant domain is aligned with SEQ ID NO:30.

In another aspect, the invention provides an antibody or antigen binding fragment thereof comprising (a) a polypeptide disclosed herein and (b) an antibody light chain constant region comprising (i) an engineered cysteine residue at position 110, 111, 125, 149, 155, 158, 161, 185, 188, 189, 191, 197, 205, 206, 207, 208, 210, or any combination thereof, according to the numbering of Kabat; (ii) an engineered cysteine residue at a position corresponding to residue 4, 42, 81, 100, 103, or any combination thereof, of SEQ ID NO:30, when said constant domain is aligned with SEQ ID NO:30 (kappa light chain); or (iii) an engineered cysteine residue at a position corresponding to residue 4, 5, 19, 43, 49, 52, 55, 78, 81, 82, 84, 90, 96, 97, 98, 99, 101, or any combination thereof, of SEQ ID NO:31, when said constant domain is aligned with SEQ ID NO:31 (lambda light chain).

In another aspect, the invention provides an antibody or antigen binding fragment thereof comprising (a) a polypeptide disclosed herein and (b) an antibody kappa light chain constant region comprising (i) an engineered cysteine residue at position 111, 149, 188, 207, 210, or any combination thereof (preferably 111 or 210), according to the numbering of Kabat; or (ii) an engineered cysteine residue at a position corresponding to residue 4, 42, 81, 100, 103, or any combination thereof, of SEQ ID NO:30 (preferably residue 4 or 103), when said constant domain is aligned with SEQ ID NO:30.

In another aspect, the invention provides an antibody or antigen binding fragment thereof comprising (a) a polypeptide disclosed herein and (b) an antibody lambda light chain constant region comprising (i) an engineered cysteine residue at position 110, 111, 125, 149, 155, 158, 161, 185, 188, 189, 191, 197, 205, 206, 207, 208, 210, or any combination thereof (preferably 110, 111, 125, 149, or 155), according to the numbering of Kabat; or (ii) an engineered cysteine residue at a position corresponding to residue 4, 5, 19, 43, 49, 52, 55, 78, 81, 82, 84, 90, 96, 97, 98, 99, 101, or any combination thereof of SEQ ID NO:31 (preferably residue 4, 5, 19, 43, or 49), when said constant domain is aligned with SEQ ID NO:31.

Amino acid modifications can be made by any method known in the art and many such methods are well known and routine for the skilled artisan. For example, but not by way of limitation, amino acid substitutions, deletions and insertions may be accomplished using any well-known PCR-based technique. Amino acid substitutions may be made by site-directed mutagenesis (see, for example, Zoller and Smith, 1982, Nucl. Acids Res. 10:6487-6500; and Kunkel, 1985, PNAS 82:488).

In applications where retention of antigen binding is required, such modifications should be at sites that do not disrupt the antigen binding capability of the antibody. In preferred embodiments, the one or more modifications are made in the constant region of the heavy and/or light chains.

Typically, the $K_D$ for the antibody with respect to the target will be 2-fold, preferably 5-fold, more preferably 10-fold less than the $K_D$ with respect to another, non-target molecule such as, but not limited to, unrelated material or accompanying material in the environment. More preferably, the $K_D$ will be 50-fold less, such as 100-fold less or 200-fold less; even more preferably 500-fold less, such as 1,000-fold less, or 10,000-fold less than the $K_D$ with respect the non-target molecule.

The value of this dissociation constant can be determined directly by well-known methods, and can be computed even for complex mixtures by methods such as those, for example, set forth in Caceci et al., 1984, Byte 9: 340-362. For example, the $K_D$ may be established using a double-filter nitrocellulose filter binding assay such as that disclosed by Wong and Lohman, 1993, Proc. Natl. Acad. Sci. USA 90: 5428-5432. Other standard assays to evaluate the binding ability of ligands such as antibodies towards targets are known in the art, including for example, ELISAs, Western blots, RIAs, and flow cytometry analysis. The binding kinetics and binding affinity of the antibody also can be assessed by standard assays known in the art, such as Surface Plasmon Resonance (SPR), e.g. by using a Biacore™ system.

A competitive binding assay can be conducted in which the binding of the antibody to the target is compared to the binding of the target by another ligand of that target, such as another antibody. The concentration at which 50 percent binding inhibition occurs is known as the $K_i$. Under ideal conditions, the $K_i$ is equivalent to $K_D$. The $K_i$ value will never be less than the $K_D$, so measurement of $K_i$ can conveniently be substituted to provide an upper limit for $K_D$.

An antibody of the invention may have a $K_D$ for its target of no more than about $1\times10^{-3}$ M, such as no more than about $1\times10^{-3}$ M, no more than about $9\times10^{-4}$ M, no more than about $8\times10^{-4}$ M, no more than about $7\times10^{-4}$ M, no more than about $6\times10^{-4}$ M, no more than about $5\times10^{-4}$ M, no more than about $4\times10^{-4}$ M, no more than about $3\times10^{-4}$ M, no more than about $2\times10^{-4}$ M, no more than about $1\times10^{-4}$ M, no more than about $9\times10^{-5}$ M, no more than about $8\times10^{-5}$ M, no more than about $7\times10^{-5}$ M, no more than about $6\times10^{-5}$ M, no more than about $5\times10^{-5}$ M, no more than about $4\times10^{-5}$ M, no more than about $3\times10^{-5}$ M, no more than about $2\times10^{-5}$ M, no more than about $1\times10^{-5}$ M, no more than about $9\times10^{-6}$ M, no more than about $8\times10^{-6}$ M, no more than about $7\times10^{-6}$ M, no more than about $6\times10^{-6}$ M, no more than about $5\times10^{-6}$ M, no more than about $4\times10^{-6}$ M, no more than about $3\times10^{-6}$ M, no more than about $2\times10^{-6}$ M, no more than about $1\times10^{-6}$ M, no more than about $9\times10^{-7}$ M, no more than about $8\times10^{-7}$ M, no more than about $7\times10^{-7}$ M, no more than about $6\times10^{-7}$ M, no more than about $5\times10^{-7}$ M, no more than about $4\times10^{-7}$ M, no more than about $3\times10^{-7}$ M, no more than about $2\times10^{-7}$ M, no more than about $1\times10^{-7}$ M, no more than about $9\times10^{-8}$ M, no more than about $8\times10^{-8}$ M, no more than about $7\times10^{-8}$ M, no more than about $6\times10^{-8}$ M, no more than about $5\times10^{-8}$ M, no more than about $4\times10^{-8}$ M, no more than about $3\times10^{-8}$ M, no more than about $2\times10^{-8}$ M, no more than about $1\times10^{-8}$ M, no more than about $9\times10^{-9}$ M, no more than about $8\times10^{-9}$ M, no more than about $7\times10^{-9}$ M, no more than about $6\times10^{-9}$ M, no more than about $5\times10^{-9}$ M, no more than about $4\times10^{-9}$ M, no more than about $3\times10^{-9}$ M, no more than about $2\times10^{-9}$ M, no more than about $1\times10^{-9}$ M, from about $1\times10^{-9}$ M to about $1\times10^{-13}$ M, $1\times10^{-4}$ M to about $1\times10^{-13}$ M, $1\times10^{-5}$ M to about $1\times10^{-13}$ M, from about $1\times10^{-6}$ M to about $1\times10^{-13}$ M, from about $1\times10^{-7}$ M to about $1\times10^{-13}$ M, from about $1\times10^{-8}$ M to about $1\times10^{-13}$ M, from about $1\times10^{-9}$ M to about $1\times10^{-13}$ M, $1\times10^{-3}$ M to about $1\times10^{-12}$ M, $1\times10^{-4}$ M to about $1\times10^{-12}$ M, from about $1\times10^{-5}$ M to about $1\times10^{-12}$ M, from about $1\times10^{-6}$ M to about $1\times10^{-12}$ M, from about $1\times10^{-7}$ M to about $1\times10^{-12}$ M, from about $1\times10^{-8}$ M to about $1\times10^{-12}$ M, from about $1\times10^{-9}$ M to about $1\times10^{-12}$ M, $1\times10^{-3}$ M to about $1\times10^{-11}$ M, $1\times10^{-4}$ M to about $1\times10^{-11}$ M, from about $1\times10^{-5}$ M to about $1\times10^{-11}$ M, from about $1\times10^{-6}$ M to about $1\times10^{-11}$ M, from about $1\times10^{-7}$ M to about $1 \times 10^{-11}$ M, from about $1 \times 10^{-8}$ M to about $1 \times 10^{-11}$ M, from about $1 \times 10^{-9}$ M to about $1 \times 10^{-11}$ M, $1 \times 10^{-3}$ M to about $1 \times 10^{-10}$ M, $1 \times 10^{-4}$ M to about $1 \times 10^{-10}$ M, from about $1 \times 10^{-5}$ M to about $1 \times 10^{-10}$ M, from about $1 \times 10^{-6}$ M to about $1 \times 10^{-10}$ M, from about $1 \times 10^{-7}$ M to about $1 \times 10^{-10}$ M, from about $1 \times 10^{-8}$ M to about $1 \times 10^{-10}$ M, or from about $1 \times 10^{-9}$ M to about $1 \times 10^{-10}$ M.

Although in general, $K_D$ at nanomolar range is desired, in certain embodiments, low affinity antibodies may be preferred, for example, for targeting highly expressed receptors in compartments and avoiding off-target binding. Further, some therapeutic applications may benefit from an antibody with lower binding affinity to facilitate antibody recycling.

Antibodies of the disclosure should retain the antigen binding capability of their native counterparts. In one embodiment, the antibodies of the disclosure exhibit essentially the same affinity as compared to an antibody prior to Cys substitution. In another embodiment, antibodies of the disclosure exhibit a reduced affinity as compared to an antibody prior to Cys substitution. In another embodiment, antibodies of the disclosure exhibit an enhanced affinity as compared to an antibody prior to Cys substitution.

In one embodiment, an antibody of the disclosure may have a dissociation constant ($K_D$) about equal to the $K_D$ of the antibody prior to Cys substitution. In one embodiment, an antibody of the disclosure may have a dissociation constant ($K_D$) about 1-fold, about 2-fold, about 3-fold, about 4-fold, about 5-fold, about 10-fold, about 20-fold, about 50-fold, about 100-fold about 150-fold, about 200-fold, about 250-fold, about 300-fold, about 400-fold, about 500-fold, about 600-fold, about 700-fold, about 800-fold, about 900-fold, or about 1000-fold greater for its cognate antigen compared with the $K_D$ of the antibody prior to Cys substitution.

In yet another embodiment, an antibody of the disclosure may have a $K_D$ about 1-fold, about 2-fold, about 3-fold, about 4-fold, about 5-fold, about 10-fold, about 20-fold, about 50-fold, about 100-fold, about 150-fold, about 200-fold, about 250-fold, about 300-fold, about 400-fold, about 500-fold, about 600-fold, about 700-fold, about 800-fold, about 900-fold, or about 1000-fold lower for its cognate antigen compared with the $K_D$ of the antibody prior to Cys substitution.

Nucleic acids encoding the heavy and light chains of the antibodies used to make the ADCs of the invention can be cloned into a vector for expression or propagation. The sequence encoding the antibody of interest may be maintained in vector in a host cell and the host cell can then be expanded and frozen for future use.

ADCs can be made with an antibody component directed to any antigen using site specific conjugation through an engineered cysteine at position 334 and/or position 392 (according to Eu index of Kabat) either alone or in combination with other positions disclosed herein (e.g., positions 290 and 347 according to Eu index of Kabat).

In some embodiments, the antibody or antigen binding fragment thereof is selected from the group consisting of: abagovomab, abatacept (ORENCIA®), abciximab (REOPRO®, c7E3 Fab), adalimumab (HUMIRA®), adecatumumab, alemtuzumab (CAMPATH®, MabCampath or Campath-1H), altumomab, afelimomab, anatumomab mafenatox, anetumumab, anrukizumab, apolizumab, arcitumomab, aselizumab, atlizumab, atorolimumab, bapineuzumab, basiliximab (SIMULECT®), bavituximab (LYMPHOSCAN®), belimumab (LYMPHOSTAT-B®), bertilimumab, besilesomab, βcept (ENBREL®), bevacizumab (AVASTIN®), biciromab brallobarbital, bivatuzumab mertansine, brentuximab vedotin (ADCETRIS®), canakinumab (ACZ885), cantuzumab mertansine, capromab (PROSTASCINT®), catumaxomab (REMOV AB®), cedelizumab (CIMZIA®), certolizumab pegol, cetuximab (ERBITUX®), clenoliximab, dacetuzumab, dacliximab, daclizumab (ZENAPAX(®), denosumab (AMG 162), detumomab, dorlimomab aritox, dorlixizumab, duntumumab, durimulumab, durmulumab, ecromeximab, eculizumab (SOLIRIS®), edobacomab, edrecolomab (Mabl7-1A, PANOREX®), efalizumab (RAPTIVA®), efungumab (MYCOGRAB®), elsilimomab, enlimomab pegol, epitumomab cituxetan, efalizumab, epitumomab, epratuzumab, erlizumab, ertumaxomab (REXOMUN®), etaracizumab (etaratuzumab, VITAXI N®, ABEGRIN™), exbivirumab, fanolesomab (NEUTROSPEC®), faralimomab, felvizumab, fontolizumab (HUZAF®), galiximab, gantenerumab, gavilimomab (ABX-CBL®), gemtuzumab ozogamicin (MYLOTARG®), golimumab (CNTO 148), gomiliximab, ibalizumab (TNX-355), ibritumomab tiuxetan (ZEVALIN®), igovomab, imciromab, infliximab (REMICAD E®), inolimomab, inotuzumab ozogamicin, ipilimumab (YERVOY®, MDX-010), iratumumab, keliximab, labetuzumab, lemalesomab, lebrilizumab, lerdelimumab, lexatumumab (HGS-ETR2, ETR2-ST01), lexitumumab, libivirumab, lintuzumab, lucatumumab, lumiliximab, mapatumumab (HGS-ETRI, TRM-I), maslimomab, matuzumab (EMD72000), mepolizumab (BOSATRIA®), metelimumab, milatuzumab, minretumomab, mitumomab, morolimumab, motavizumab (NUMAX™), muromonab (OKT3), nacolomab tafenatox, naptumomab estafenatox, natalizumab (TYSABRI®, ANTEGREN®), nebacumab, nerelimomab, nimotuzumab (THERACIM hR3®, THERA-CIM-hR3®, THERALOC®), nofetumomab merpentan (VERLUMA®), ocrelizumab, odulimomab, ofatumumab, omalizumab (XOLAIR®), oregovomab (OVAREX®), otelixizumab, pagibaximab, palivizumab (SYNAGIS®), panitumumab (ABX-EGF, VECTIBIX®), pascolizumab, pemtumomab (THERAGYN®), pertuzumab (2C4, OMNITARG®), pexelizumab, pintumomab, ponezumab, priliximab, pritumumab, ranibizumab (LUCENTIS®), raxibacumab, regavirumab, reslizumab, rituximab (RITUXAN®, MabTHERA®), rovelizumab, ruplizumab, satumomab, sevirumab, sibrotuzumab, siplizumab (MEDI-507), sontuzumab, stamulumab (Myo-029), sulesomab (LEUKOSCAN®), tacatuzumab tetraxetan, tadocizumab, talizumab, taplitumomab paptox, tefibazumab (AUREXIS®), telimomab aritox, teneliximab, teplizumab, ticilimumab, tocilizumab (ACTEMRA®), toralizumab, tositumomab, trastuzumab, tremelimumab (CP-675,206), tucotuzumab celmoleukin, tuvirumab, urtoxazumab, ustekinumab (CNTO 1275), vapaliximab, veltuzumab, vepalimomab, visilizumab (NUVION®), volociximab (M200), votumumab (HUMASPECT®), zalutumumab, zanolimumab (HuMAX-CD4), ziralimumab, or zolimomab aritox.

In some embodiments the antigen binding domain comprises a heavy and light chain variable domain having six CDRs, and/or competes for binding with an antibody selected from the preceding list. In some embodiments the antigen binding domain binds to the same epitope as the antibodies in the preceding list. In some embodiments the antigen binding domain comprises a heavy and light chain variable domain having six total CDRs, and binds to the same antigen as the antibodies in the preceding list.

In some embodiments the antigen binding domain comprises a heavy and light chain variable domain having six (6) total CDRs, and specifically binds to an antigen selected from the group consisting of: PDGFRα, PDGFRβ, PDGF, VEGF, VEGF-A, VEGF-B, VEGF-C, VEGF-D, VEGF-E, VEGF-F, VEGFR1, VEGFR2, VEGFR3, FGF, FGF2, HGF, KDR, FLT-1, FLK-1, Ang-2, Ang-1, PLGF, CEA, CXCL13, BAFF, IL-21, CCL21, TNF-α, CXCL12, SDF-I, bFGF, MAC-I, IL23p19, FPR, IGFBP4, CXCR3, TLR4, CXCR2, EphA2, EphA4, EphrinB2, EGFR(ErbBI), HER2(ErbB2 or pl85neu), HER3(ErbB3), HER4 ErbB4 or tyro2), SCI, LRP5, LRP6, RAGE, s100A8, s100A9, Navl.7, GLPI, RSV, RSV F protein, Influenza HA protein, Influenza NA protein, HMGBI, CD16, CD19, CD20, CD21, CD28, CD32, CD32b, CD64, CD79, CD22, ICAM-I, FGFRI, FGFR2, HDGF, EphB4, GITR, β-amyloid, hMPV, PIV-I, PIV-2, OX40L, IGFBP3, cMet, PD-I, PLGF, Neprolysin, CTD, IL-18, IL-6, CXCL-13, IL-IRI, IL-15, IL-4R, IgE, PAI-I, NGF, EphA2, uPARt, DLL-4, avβ5, avβ6, α5β1, a3β1, interferon receptor type I and type II, CD 19, ICOS, IL-17, Factor II, Hsp90, IGF, IGF-I, IGF-II, CD 19, GM-CSFR, PIV-3, CMV, IL-13, IL-9, and EBV.

In some embodiments the antigen binding domain specifically binds to a member (receptor or ligand) of the TNF superfamily. The TNF superfamily member may be selected from the group including, but not limited to, Tumor Necrosis Factor-α ("TNF-α"), Tumor Necrosis Factor-β ("TNF-β"), Lymphotoxin-α ("LT-α"), CD30 ligand, CD27 ligand, CD40 ligand, 4-1 BB ligand, Apo-1 ligand (also referred to as Fas ligand or CD95 ligand), Apo-2 ligand (also referred to as TRAIL), Apo-3 ligand (also referred to as TWEAK), osteoprotegerin (OPG), APRIL, RANK ligand (also referred to as TRANCE), TALL-I (also referred to as BlyS, BAFF or THANK), DR4, DR5 (also known as Apo-2, TRAIL-R2, TR6, Tango-63, hAPO8, TRICK2, or KILLER), DR6, DcRI, DcR2, DcR3 (also known as TR6 or M68), CARI, HVEM (also known as ATAR or TR2), GITR, ZTNFR-5, NTR-I, TNFLI, CD30, LTBr, 4-1BB receptor and TR9.

In some embodiments the antigen binding domain is capable of binding one or more targets chosen from the group including, but not limited to, 5T4, ABL, ABCB5, ABCFI, ACVRI, ACVRIB, ACVR2, ACVR2B, ACVRLI, ADORA2A, Aggrecan, AGR2, AICDA, AIFI, AIGI, AKAPI, AKAP2, AMH, AMHR2, angiogenin (ANG), ANGPTI, ANGPT2, ANGPTL3, ANGPTL4, Annexin A2, ANPEP, APC, APOCI, AR, aromatase, ATX, AXI, AZGPI (zinc-a-glycoprotein), B7.1, B7.2, B7-H1, BAD, BAFF, BAG1, BAll, BCR, BCL2, BCL6, BDNF, BLNK, BLRI (MDR15), BlyS, BMP1, BMP2, BMP3B (GDFIO), BMP4, BMP6, BMP7, BMP8, BMP9, BMP11, BMP12, BMPR1A, BMPR1B, BMPR2, BPAGI (plectin), BRCAI, C19orflO (IL27w), C3, C4A, C5, C5R1, CANTI, CASPI, CASP4, CAVI, CCBP2 (D6/JAB61), CCLI (1-309), CCLI 1 (eotaxin), CCL13 (MCP-4), CCL15 (MIP-Id), CCL16 (HCC-4), CCL17 (TARC), CCL18 (PARC), CCL19 (MIP-3b), CCL2 (MCP-1), MCAF, CCL20 (MIP-3a), CCL21 (MEP-2), SLC, exodus-2, CCL22(MDC/STC-I), CCL23 (MPIF-1), CCL24 (MPIF-2/eotaxin-2), CCL25 (TECK), CCL26 (eotaxin-3), CCL27 (CTACK/ILC), CCL28, CCL3 (MIP-Ia), CCL4 (MIP-Ib), CCL5(RANTES), CCL7 (MCP-3), CCL8 (mcp-2), CCNAI, CCNA2, CCNDI, CCNEI, CCNE2, CCRI (CKRI/HM145), CCR2 (mcp-IRB/RA), CCR3 (CKR3/CMKBR3), CCR4, CCR5(CMKBR5/ChemR13), CCR6 (CMKBR6/CKR-L3/STRL22/DRY6), CCR7 (CKR7/EBI1), CCR8 (CMKBR8/TERI/CKR-LI), CCR9 (GPR-9-6), CCRLI (VSHKI), CCRL2 (L-CCR), CD164, CD19, CDIC, CD20, CD200, CD-22, CD24, CD28, CD3, CD33, CD35, CD37, CD38, CD3E, CD3G, CD3Z, CD4, CD40, CD40L, CD44, CD45RB, CD46, CD52, CD69, CD72, CD74, CD79A, CD79B, CD8, CD80, CD81, CD83, CD86, CD105, CD137, CDHI (E-cadherin), CDCP1CDH10, CDH12, CDH13, CDH18, CDH19, CDH20, CDH5, CDH7, CDH8, CDH9, CDK2, CDK3, CDK4, CDK5, CDK6, CDK7, CDK9, CDKNIA (p21WapI/CipI), CDKNIB (p27KipI), CDKNIC, CDKN2A (pl6INK4a), CDKN2B, CDKN2C, CDKN3, CEBPB, CERI, CHGA, CHGB, Chitinase, CHSTIO, CKLFSF2, CKLFSF3, CKLFSF4, CKLFSF5, CKLFSF6, CKLFSF7, CKLFSF8, CLDN3, CLDN7 (claudin-7), CLN3, CLU (clusterin), CMKLRI, CMKORI (RDCI), CNRI, COLI 8AI, COL1A1.COL4A3, COL6A1, CR2, Cripto, CRP, CSF1 (M-CSF), CSF2 (GM-CSF), CSF3 (GCSF), CTLA4, CTL8, CTNNBI (b-catenin), CTSB (cathepsin B), CX3CL1 (SCYDI), CX3CR1 (V28), CXCLI(GROI), CXCLIO (IP-IO), CXCL11 (1-TAC/IP-9), CXCL12 (SDFI), CXCL13, CXCL 14, CXCL 16, CXCL2 (GR02), CXCL3 (GR03), CXCL5 (ENA-78/LIX), CXCL6 (GCP-2), CXCL9 (MIG), CXCR3 (GPR9/CKR-L2), CXCR4, CXCR6 (TYMSTR/STRL33/Bonzo), CYB5, CYCI, Cyr61, CYSLTRI, c-Met, DAB21P, DES, DKFZp451J0118, DNCLI, DPP4, E2F1, ECGFI5EDGI, EFNAI, EFNA3, EFNB2, EGF, ELAC2, ENG, endoglin, ENOI, EN02, EN03, EPHAI, EPHA2, EPHA3, EPHA4, EPHA5, EPHA6, EPHA7, EPHA8, EPHA9, EPHAIO, EPHBI, EPHB2, EPHB3, EPHB4, EPHB5, EPHB6, EPHRIN-AI, EPHRIN-A2, EPHRIN-A3, EPHRIN-A4, EPHRIN-A5, EPHRIN-A6, EPHRIN-BI, EPHRIN-B2, EPHRTN-B3, EPHB4, EPG, ERBB2 (Her-2), EREG, ERK8, Estrogen receptor, ESRI, ESR2, F3 (TF), FADD, farnesyltransferase, FasL, FASNf, FCER1A, FCER2, FCGR3A, FGF, FGF1 (aFGF), FGF10, FGF11, FGF12, FGF12B, FGF13, FGF14, FGF16, FGF17, FGF18, FGF19, FGF2 (bFGF), FGF20, FGF21 (such as mimAbl), FGF22, FGF23, FGF3 (int-2), FGF4 (HST), FGF5, FGF6 (HST-2), FGF7 (KGF), FGF8, FGF9, FGFR3, FIGF (VEGFD), FILI(EPSILON), FBLI (ZETA), FLJ12584, FLJ25530, FLRTI (fibronectin), FLTI, FLT-3, FOS, FOSLI (FRA-I), FY (DARC), GABRP (GABAa), GAGEBI, GAGECI, GALNAC4S-6ST, GATA3, GD2, GD3, GDF5, GDF8, GFII, GGTI, GM-CSF, GNASI, GNRHI, GPR2 (CCRIO), GPR31, GPR44, GPR81 (FKSG80), GRCCIO (CIO), gremlin, GRP, GSN (Gelsolin), GSTPI, HAVCR2, HDAC, HDAC4, HDAC5, HDAC7A, HDAC9, Hedgehog, HGF, HIFIA, HIPI, histamine and histamine receptors, HLA-A, HLA-DRA, HM74, HMOXI, HSP90, HUMCYT2A, ICEBERG, ICOSL, ID2, IFN-a, IFNAI, IFNA2, IFNA4, IFNA5, EFNA6, BFNA7, IFNB1, IFN-gamma, IFNWI, IGBPI, IGF1, IGF1R, IGF2, IGFBP2, IGFBP3, IGFBP6, DL-I, ILIO, ILIORA, ILIORB, IL-1, ILIRI (CD121a), ILIR2(CD121b), IL-IRA, IL-2, IL2RA (CD25), IL2RB(CD122), IL2RG(CD132), IL-4, IL-4R (CD123), IL-5, IL5RA(CD125), IL3RB(CD131), IL-6, IL6RA (CD126), IR6RB(CD130), IL-7, IL7RA(CD127), IL-8, CXCRI (IL8RA), CXCR2 (IL8RB/CD128), IL-9, IL9R (CD129), IL-10, IL10RA(CD210), IL10RB (CDW210B), IL-11, ILI IRA, IL-12, IL-12A, IL-12B, IL-12RB1, IL-12RB2, IL-13, IL13RA1, IL13RA2, IL14, IL15, IL15RA, 1L16, IL17, IL17A, IL17B, IL17C, IL17R, IL18, IL18BP, IL18R1, IL18RAP, IL19, IL1A, IL1B, IL1F10, IL1F5, IL1F6, IL1F7, IL1F8, DL1F9, IL1HYI, IL1R1, IL1R2, IL1RAP, IL1RAPL1, IL1RAPL2, IL1RL1, IL1RL2, IL1RN, IL2, IL20, IL20RA, IL21R, IL22, IL22R, IL22RA2, IL23, DL24, IL25, IL26, IL27, IL28A, IL28B, IL29, IL2RA, IL2RB, IL2RG, IL3, IL30, IL3RA, IL4, IL4R, IL6ST (glycoprotein 130), ILK, INHA, INHBA, INSL3, INSL4, IRAKI, IRAK2, ITGA1, ITGA2, ITGA3, ITGA6 (α 6 integrin), ITGAV, ITGB3, ITGB4 (β 4 integrin), JAK1, JAK3, JTB, JUN, K6HF, KAII, KDR, KIM-1, KITLG, KLF5 (GC Box BP), KLF6, KLK10, KLK12, KLK13, KLK14, KLK15, KLK3, KLK4, KLK5, KLK6, KLK9, KRT1, KRT19 (Keratin 19), KRT2A, KRTHB6 (hair-specific type II keratin), LAMA5, LEP (leptin), Lingo-p75, Lingo-Troy, LPS, LRP5, LRP6, LTA (TNF-b), LTB, LTB4R (GPR16), LTB4R2, LTBR, MACMARCKS, MAG or Omgp, MAP2K7 (c-Jun), MCP-I, MDK, MIBI, midkine, MIF, MISRII, MJP-2, MK, MK167 (Ki-67), MMP2, MMP9, MS4A1, MSMB, MT3 (metallothionectin-Ui), mTOR, MTSSI, MUCI (mucin), MYC, MYD88, NCK2, neurocan, neuregulin-1, neuropilin-1, NFKBI, NFKB2, NGFB (NGF), NGFR, NgR-Lingo, NgR-Nogo66 (Nogo), NgR-p75, NgR-Troy, NMEI (NM23A), NOTCH, NOTCH1, N0X5, NPPB, NROBI, NROB2, NRIDI, NR1D2, NR1H2, NR1H3, NR1H4, NR1I2, NR1I3, NR2C1, NR2C2, NR2E1, NR2E3, NR2F1, NR2F2, NR2F6, NR3C1, NR3C2, NR4A1, NR4A2, NR4A3, NR5A1, NR5A2, NR6A1, NRPI, NRP2, NT5E, NTN4, OCT-1, ODZ1, OPN1, OPN2, OPRDI, P2RX7, PAP, PARTI, PATE, PAWR, PCA3, PCDGF, PCNA, PDGFA, PDGFB, PDGFRA, PDGFRB, PECAMI, peg-asparaginase, PF4 (CXCL4), Plexin B2 (PLXNB2), PGF, PGR, phosphacan, PIAS2, PI3 Kinase, PIK3CG, PLAU (uPA), PLG5PLXDCI, PKC, PKC-β, PPBP (CXCL7), PPID, PRI, PRKCQ, PRKDI, PRL, PROC, PROK2, pro-NGF, prosaposin, PSAP, PSCA, PTAFR, PTEN, PTGS2 (COX-2), PTN, RAC2 (P21Rac2), RANK, RANK ligand, RARE, RGSI, RGS13, RGS3, RNFI10 (ZNF144), Ron, ROB02, RXR, selectin, S100A2, S100A8, S100A9, SCGB 1D2 (lipophilin B), SCGB2A1 (mammaglobin 2), SCGB2A2 (mammaglobin 1), SCYEI (endothelial Monocyte-activating cytokine), SDF2, SERPENA1, SERPINA3, SERPINB5 (maspin), SERPINEI (PAI-I), SERPINFI, SHIP-I, SHIP-2, SHBI, SHB2, SHBG, SfcAZ, SLC2A2, SLC33A1, SLC43A1, SLIT2, SPPI, SPRRIB (Sprl), ST6GAL1, STABI, STAT6, STEAP, STEAP2, SULF-1, Sulf-2, TB4R2, TBX21, TCPIO, TDGFI, TEK, TGFA, TGFB1, TGFBIII, TGFB2, TGFB3, TGFBI, TGFBRI, TGFBR2, TGFBR3, THIL, THBSI (thrombospondin-1), THBS2/THBS4, THPO, TIE (Tie-1), TIMP3, tissue factor, TIKI2, TLR10, TLR2, TLR3, TLR4, TLR5, TLR6JLR7, TLR8, TLR9, TM4SF1, TNF, TNF-a, TNFAIP2 (B94), TNFAIP3, TNFRSFIIA, TNFRSFIA, TNFRSFIB, TNFRSF21, TNFRSF5, TNFRSF6 (Fas), TNFRSF7, TNFRSF8, TNFRSF9, TNFSFIO (TRAIL), TNFSFI 1 (TRANCE), TNFSF12 (AP03L), TNFSF13 (April), TNFSF13B, TNFSF14 (HVEM-L), TNFSF15 (VEGI), TNFSF 18, TNFSF4 (OX40 ligand), TNFSF5 (CD40 ligand), TNFSF6 (FasL), TNFSF7 (CD27 ligand), TNFSF8 (CD30 ligand), TNFSF9 (4-1BB ligand), TOLLIP, Toll-like receptors, TLR2, TLR4, TLR9, TOP2A (topoisomerase lia), TP53, TPMI, TPM2, TRADD, TRAFI, TRAF2, TRAF3, TRAF4, TRAF5, TRAF6, TRKA, TREMI, TREM2, TRPC6, TROY, TSLP, TWEAK, Tyrosinase, uPAR, VEGF, VEGFB, VEGFC, versican, VHL C5, VLA-4, Wnt-1, XCLI (lymphotactin), XCL2 (SCM-Ib), XCRI (GPR5/CCXCRI), YYI, and ZFPM2.

In some embodiments, the antibody, or antigen-binding fragment thereof, binds to extra-domain B (EDB) of fibronectin (FN). FN-EDB is a small domain of 91 amino acids, which can be inserted into fibronectin molecules by a mechanism of alternative splicing. The amino acid sequence of FN-EDB is 100% conserved between human, cynomolgus monkey, rat and mouse. FN-EDB is overexpressed during embryonic development and broadly expressed in human cancers, but virtually undetectable in normal adult except female reproductive tissues.

In some embodiments, the antibody or antigen binding fragment thereof binds to an antigen selected from the group consisting of: HER2, HER3, HER4, CD22, and CD33. In some embodiments, the antibody or antigen binding fragment thereof binds to Her2. In some embodiments, the antibody comprises trastuzumab. In some embodiments, the antibody or antigen binding fragment thereof binds to CD33.

Table 18 provides the amino acid (protein) and nucleic acid sequences of CD33 antibody used in constructing exemplary site specific ADCs of the invention. The CDRs shown are defined by Kabat and Chothia numbering. The heavy chain constant region and light chain constant region were altered to contain on or more modifications to allow for site specific conjugation when making the exemplary ADCs of the invention. Modifications to the amino acid sequences in the antibody constant region to allow for site specific conjugation (positions 334 and 392) are underlined and bolded. In the instant disclosure, the nomenclature for the modified antibodies is the antigen (e.g., CD33 or Her2) followed by a dash and then the position of the amino acid of modification flanked by the single letter amino acid code for the wild type residue and the single letter amino acid code for the residue that is now in that position in the modified antibody (e.g., CD33-K334C or Her2-K392C).

In certain embodiments, the antibody, or antigen-binding fragment thereof, described herein comprises the following heavy chain CDR sequences: (i) a VH complementarity determining region one (CDR-H1) sharing at least 90%, at least 91%, at least 92%, at least 93%, at least 94%, or at least 95% identity to SEQ ID NO: 5 or 6, a CDR-H2 sharing at least 90%, at least 91%, at least 92%, at least 93%, at least 94%, or at least 95% identity with SEQ ID NO: 9 or 10, and a CDR-H3 sharing at least 90%, at least 91%, at least 92%, at least 93%, at least 94%, or at least 95% identity with SEQ ID NO: 13; and/or (ii) the following light chain CDR sequences: a VL complementarity determining region one (CDR-L1) sharing at least 90%, at least 91%, at least 92%, at least 93%, at least 94%, or at least 95% identity with SEQ ID NO: 17, a CDR-L2 sharing at least 90%, at least 91%, at least 92%, at least 93%, at least 94%, or at least 95% identity with SEQ ID NO: 19, and a CDR-L3 sharing at least 90%, at least 91%, at least 92%, at least 93%, at least 94%, or at least 95% identity with SEQ ID NO: 21.

In certain embodiments, the antibody or antigen-binding fragment thereof described herein comprises (i) a heavy chain variable region (VH) comprising an amino acid sequence that is at least 50%, at least 60%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% identical to SEQ ID NO: 1, and/or (ii) light chain variable region (VL) comprising an amino acid sequence that is at least 50%, at least 60%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% identical to SEQ ID NO: 3. Any combination of these VL and VH sequences is also encompassed by the invention.

In certain embodiments, the antibody or antigen-binding fragment thereof described herein comprises an Fc domain. The Fc domain can be derived from IgA (e.g., $IgA_1$ or $IgA_2$), IgG, IgE, or IgG (e.g., $IgG_1$, $IgG_2$, $IgG_3$, or $IgG_4$).

In certain embodiments, the antibody or antigen-binding fragment thereof described herein comprises (i) a heavy chain comprising an amino acid sequence that is at least 50%, at least 60%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% identical to SEQ ID NO:

15, 32, 33 or 34 and/or (ii) a light chain comprising an amino acid sequence that is at least 50%, at least 60%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% identical to SEQ ID NO: 23. The heavy chain constant domain comprises an engineered cysteine at position 334 and/or position 392 (according to Eu index of Kabat) either alone or in combination with other positions. Any combination of these heavy chain and light chain sequences is also encompassed by the invention.

The invention provides a nucleic acid encoding an engineered polypeptide described herein. The invention also provides a nucleic acid encoding an antibody comprising an engineered polypeptide described herein.

The invention also provides a host cell comprising a nucleic acid encoding the engineered polypeptide described herein. The invention also provides a host cell comprising a nucleic acid encoding an antibody comprising the engineered polypeptide described herein.

The invention provides a nucleic acid encoding an antibody, or antigen-binding fragment thereof, of any one of the CD33 antibodies disclosed herein, and a host cell comprising such a nucleic acid.

The invention provides a method of producing an engineered polypeptide described herein, or antibody, or antigen-binding portion thereof, comprising such an engineered polypeptide. The method comprises culturing the host cell under suitable conditions for expressing the polypeptide, the antibody, or antigen-binding portion thereof, and isolating the polypeptide, or the antibody or antigen-binding fragment.

B. Drugs

Drugs useful in preparation of the site specific ADCs of the invention include any therapeutic agent useful in the treatment of cancer including, but not limited to, cytotoxic agents, cytostatic agents, immunomodulating agents and chemotherapeutic agents. A cytotoxic effect refers to the depletion, elimination and/or the killing of a target cells (i.e., tumor cells). A cytotoxic agent refers to an agent that has a cytotoxic effect on a cell. A cytostatic effect refers to the inhibition of cell proliferation. A cytostatic agent refers to an agent that has a cytostatic effect on a cell, thereby inhibiting the growth and/or expansion of a specific subset of cells (i.e., tumor cells). An immunomodulating agent refers to an agent that stimulates the immune response though the production of cytokines and/or antibodies and/or modulating T cell function thereby inhibiting or reducing the growth of a subset of cells (i.e., tumor cells) either directly or indirectly by allowing another agent to be more efficacious. A chemotherapeutic agent refers to an agent that is a chemical compound useful in the treatment of cancer. A drug may also be a drug derivative, wherein a drug has been functionalized to enable conjugation with an antibody of the invention.

In some embodiments the drug is a membrane permeable drug. In such embodiments, the payload can elicit a bystander effect wherein cells surrounding the cell that initially internalized the ADC are killed by the payload. This occurs when the payload is released from the antibody (i.e., by cleaving of a cleavable linker) and crosses the cellular membrane and, upon diffusion, induces the killing of surrounding cells.

In accordance with the disclosed methods, the drugs are used to prepare antibody drug conjugates of the formula Ab-(L-D), wherein (a) Ab is an antibody that binds to a specific target; and (b) L-D is a linker-drug moiety, wherein L is a linker, and D is a drug.

The drug-to-antibody ratio (DAR) or drug loading indicates the number of drug (D) molecules that are conjugated per antibody. The antibody drug conjugates of the present invention use site specific conjugation such that there is essentially a homogeneous population of ADCs having one DAR in a composition of ADCs. In some embodiments, the DAR is about 1, 2, 3, 4, or greater. In some embodiments, the DAR is 1. In some embodiments, the DAR is 2. In other embodiments, the DAR is 3. In other embodiments, the DAR is 4. In other embodiments, the DAR is greater than 4.

Using conventional conjugation (rather than site specific conjugation) results in a heterogeneous population of different species of ADCs, each of which with a different individual DAR. Compositions of ADCs prepared in this way include a plurality of antibodies, each antibody conjugated to a particular number of drug molecules. As such, the compositions have an average DAR. T-DM1 (Kadcyla®) uses conventional conjugation on lysine residues and has an average DAR of around 4 with a broad distribution including ADCs loaded with 0, 1, 2, 3, 4, 5, 6, 7 or 8 drug molecules (Kim et al., 2014, Bioconj Chem 25(7):1223-32).

DAR can be determined by various conventional means such as UV spectroscopy, mass spectroscopy, ELISA assay, radiometric methods, hydrophobic interaction chromatography (HIC), electrophoresis and HPLC.

In one embodiment, the drug component of the ADCs of the invention is a DNA alkylating agent. In some embodiments, the DNA alkylating agent is a DNA minor groove binding alkylating agent. In some embodiments, the DNA minor groove binding alkylating agent is a CPI, a CTI, or a CBI dimer.

As used herein, CPI refers to 1,2,8,8a-tetrahydrocyclopropa[c]pyrrolo[3,2-e]indol-4(5H)-one or a substituted or a derivatized form thereof. CPI can also refer to the seco form of CPI, or seco-CPI, which is also known as 8-(chloromethyl)-1-methyl-3,6,7,8-tetrahydropyrrolo[3,2-e]indol-4-ol, or a substituted or derivatized form (or forms) thereof. CPI dimers induce inter-strand DNA crosslinking and potent cytotoxicity.

As used herein, CBI refers to 1,2,9,9a-tetrahydro-4H-benzo[e]cyclopropa[c]indol-4-one, or a substituted or a derivatized form thereof. CBI can also refer to the seco form of CBI, or seco-CBI, which is also known as 1-(chloromethyl)-2,3-dihydro-1H-benzo[e]indol-5-ol, or a substituted or derivatized form (or forms) thereof.

As used herein, CTI refers to 1,2,8,8a-tetrahydro-4H-cyclopropa[c]thieno[3,2-e]indol-4-one, or a substituted or a derivatized form thereof. CTI can also refer to the seco form of CTI, or seco-CTI, which is also known as 8-(chloromethyl)-1-methyl-7,8-dihydro-6H-thieno[3,2-e]indol-4-01, or a substituted or derivatized form (or forms) thereof.

Two CBI and/or CPI and/or CTI cores may be linked together to form a dimeric species (so called CBI dimers, CPI dimers, CTI dimers, CBI/CPI dimers, CBI/CTI dimers, or CPI/CTI dimers).

PCT International Publication No. WO2015/110935, which is incorporated herein by reference in its entirety, discloses CPI and CBI dimers that are useful in the ADCs of the present invention and provides methods of producing the CPI and CBI dimers. PCT International Publication No. WO2016/151432, which is incorporated herein by reference in its entirety, discloses CTI dimers that are useful in the ADCs of the present invention and provides methods of producing the CTI dimers.

In some embodiments, the drug component of the ADCs of the present disclosure is a compound of Formula I:

$$F_1\text{-DL-}F_2 \quad \text{(Formula I)},$$

or a pharmaceutically acceptable salt or solvate thereof, wherein:

$F_1$ is a CPI monomer comprising:

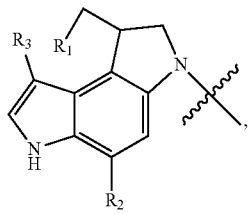

wherein $R_1$ is H, —OH, —O-acyl, azido, halo (F, Cl, Br, I), sulfonate (—OSO$_2$R), cyanate, thiocyanate, isocyanate, or thioisocyanate;

$R_2$ is $R_2$ is H, —OH, —SH, NHR, acyl, acetate, phosphate, glucuronide, or galactoside;

$R_3$ is H, —C$_1$-C$_5$ substituted or unsubstituted alkyl, substituted or unsubstituted phenyl, —C(O)OR, —C(O)SR, —C(O)NHN(R)$_2$, or —C(O)N(R)$_2$;

$F_2$ is a CPI monomer comprising:

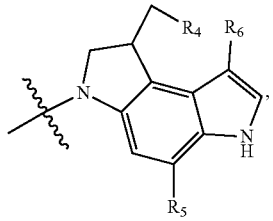

wherein $R_4$ is H, —OH, —O-acyl, azido, halo (F, Cl, Br, I), sulfonate (—OSO$_2$R), cyanate, thiocyanate, isocyanate, or thioisocyanate;

$R_5$ is H, —OH, —SH, NHR, acyl, acetate, phosphate, glucuronide, or galactoside;

$R_6$ is H, —C$_1$-C$_5$ substituted or unsubstituted alkyl, substituted or unsubstituted phenyl, —C(O)OR, —C(O)SR, —C(O)NHN(R)$_2$, or —C(O)N(R)$_2$;

R is selected from the group consisting of H, —C$_1$-C$_{20}$ alkyl, —C$_2$-C$_6$ alkenyl, —C$_2$-C$_6$ alkynyl, halo, hydroxyl, alkoxy, —NH$_2$, —NH(C$_1$-C$_8$ alkyl), —N(C$_1$-C$_8$ alkyl)$_2$, —NO$_2$, —C$_6$-C$_{14}$ aryl and —C$_6$-C$_{14}$ heteroaryl, wherein two or more R optionally join to form a ring or rings, and wherein said —C$_6$-C$_{14}$ aryl and —C$_6$-C$_{14}$ heteroaryl are optionally substituted with 1 to 5 substituents independently from —C$_1$-C$_{10}$ alkyl, —C$_1$-C$_{10}$ alkoxy, halo, —C$_1$-C$_{10}$ alkylthio, trifluoromethyl, —NH$_2$, —NH(C$_1$-C$_8$ alkyl), —N(C$_1$-C$_8$ alkyl)$_2$, —C$_1$-C$_{10}$ alkyl-N(C$_1$-C$_8$ alkyl)$_2$, —C$_1$-C$_3$ alkylthio, —NO$_2$, or —C$_1$-C$_{10}$ heterocyclyl for each ring system in which R appears;

DL is a dimer-linker comprising: R$_7$—X—R$_8$, wherein $R_7$ and $R_8$ are each independently selected from a direct bond, carbonyl, or a carbonyl acyl group bonded to $F_1$ or $F_2$ at the free nitrogen atom of the saturated five-membered ring; and X is a —C$_1$-C$_{20}$ substituted or unsubstituted alkyl chain, a —C$_1$-C$_{20}$ substituted or unsubstituted fused or bridged cycloalkyl, or a substituted or unsubstituted saturated or aromatic heterocyclic ring comprised of from 3-20 atoms selected from C, N, O, and/or S.

In some embodiments, the drug component of the ADCs of the invention is:

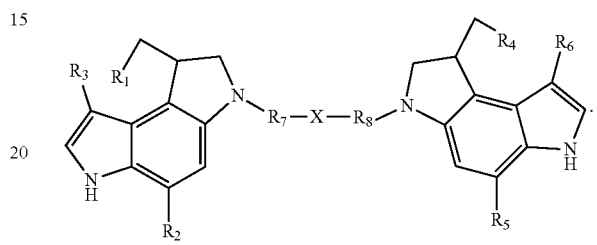

In some embodiments, $R_1$ is a halo (F, Cl, Br, I) or suphonate (—OSO$_2$R), $R_2$ is —OH, phosphate, glucuronide or galactoside, $R_3$ is a C$_1$-C$_5$ unsubstituted or substituted alkyl, $R_4$ is a halo (F, Cl, Br, I) or suphonate (—OSO$_2$R), $R_5$ is —OH, phosphate glucuronide or galactoside, and $R_6$ is a C$_1$-C$_5$ unsubstituted or substituted alkyl. In some embodiments, $R_1$ is halo. In some embodiments, $R_1$ is Cl. In some embodiments, $R_1$ is sulfonate. In some embodiments, $R_2$ is —OH. In some embodiments, $R_2$ is a phosphate group. In some embodiments, $R_3$ is a C$_3$ or C$_5$ unsubstituted or substituted alkyl group. In some embodiments, $R_3$ is a methyl group. In some embodiments, $R_4$ is halo. In some embodiments, $R_4$ is Cl. In some embodiments, $R_4$ is sulfonate. In some embodiments, $R_5$ is —OH. In some embodiments, $R_5$ is a phosphate group. In some embodiments, $R_6$ is a C$_3$ or C$_5$ unsubstituted or substituted alkyl group. In some embodiments, $R_6$ is a methyl group.

In some embodiments, $R_1$ is Cl, $R_2$ is phosphate, $R_3$ is methyl, $R_4$ is Cl, $R_5$ is —OH, and $R_6$ is methyl. In some embodiments, R, is Cl, $R_2$ is —OH, $R_3$ is methyl, $R_4$ is Cl, $R_5$ is phosphate group, and $R_6$ is methyl. In some embodiments, the drug component of the ADCs of the invention is selected from the group consisting of:

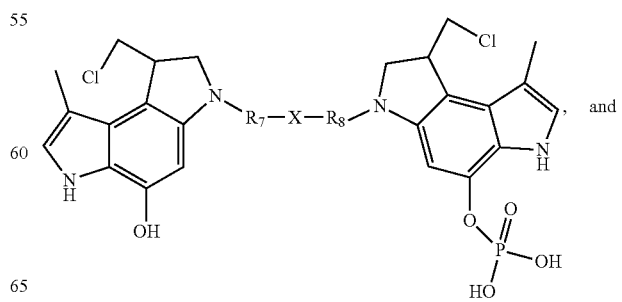

29
-continued

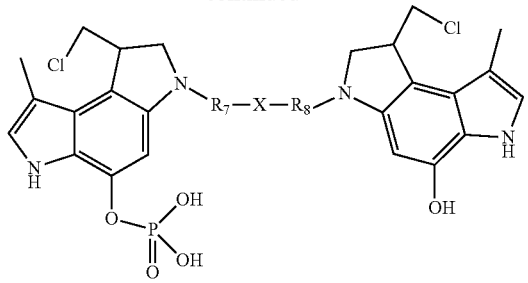

In some embodiments, $R_7$ and $R_8$ of the dimer-linker (DL) each independently is a carbonyl. In some embodiments, X is $C_1$-$C_{20}$ substituted or unsubstituted alkyl chain, a $C_1$-$C_{20}$ substituted or unsubstituted fused or bridged cycloalkyl, or a substituted or unsubstituted saturated or aromatic heterocyclic ring comprised of from 3-20 atoms selected from C, N, O, and/or S. In some embodiments, $R_7$ and $R_8$ each independently is a carbonyl, and X is a —$C_5$-$C_{10}$ substituted or unsubstituted alkyl chain, a —$C_5$-$C_{10}$ substituted or unsubstituted fused or bridged cycloalkyl, or a substituted or unsubstituted saturated or aromatic heterocyclic ring comprised of from 5-10 atoms selected from C, N, O, and/or S. In some embodiments, $R_7$ and $R_8$ each independently is a carbonyl, and X is a $C_5$ or a $C_8$ substituted or unsubstituted alkyl chain, a $C_5$ or a $C_8$ substituted or unsubstituted fused or bridged cycloalkyl, or a substituted or unsubstituted saturated or aromatic heterocyclic ring comprised of 5 or 8 atoms selected from C, N, O, and/or S.

In some embodiments, the drug component of the ADCs of the invention is selected from the group consisting of:

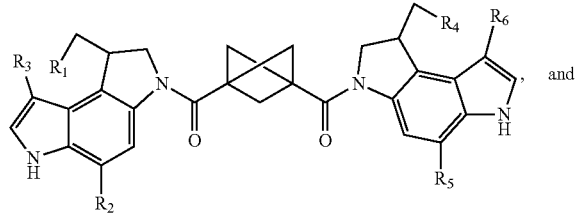, and

30
-continued

In some embodiments, the CPI dimer is selected from the group consisting of:

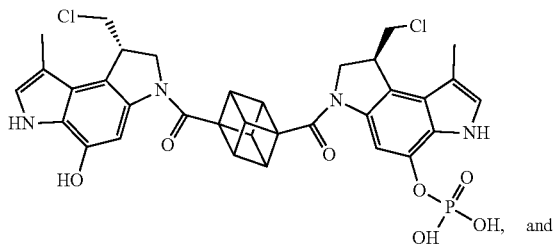, and

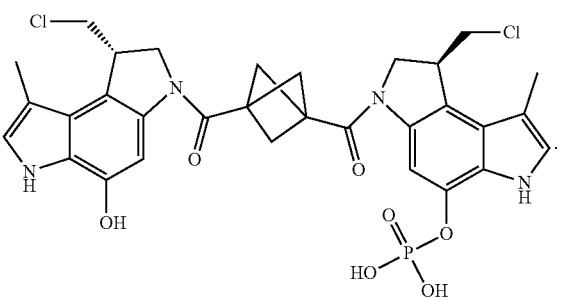

In some embodiments, the drug/payload is selected from the group disclosed in Table 1.

TABLE 1

| | Drugs | |
|---|---|---|
| Payload ID | Structure | IUPAC Name |
| P1 | 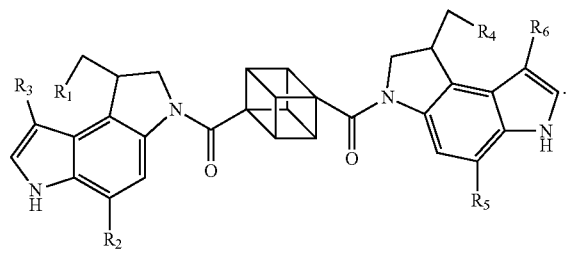 | (1S)-1-(chloromethyl)-3-[(5-{[(1S)-1-(chloromethyl)-5-hydroxy-1,2-dihydro-3H-benzo[e]indol-3-yl]carbonyl}thiophen-2-yl)carbonyl]-2,3-dihydro-1H-benzo[e]indol-5-yl dihydrogen phosphate |

TABLE 1-continued

Drugs

| Payload ID | Structure | IUPAC Name |
|---|---|---|
| P2 | 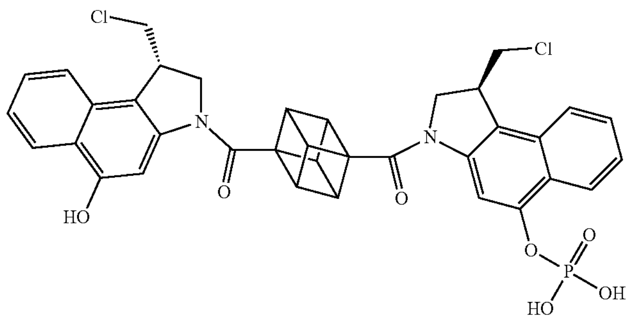 [SMILES: O=C(N1C[C@@H](CCl)c2c1cc(O)c1ccccc21)C12C3C4C1C1C2C3C41C(=O)N1C[C@@H](CCl)c2c1cc(OP(=O)(O)O)c1ccccc21] | (1S)-1-(chloromethyl)-3-[(4-{[(1S)-1-(chloromethyl)-5-hydroxy-1,2-dihydro-3H-benzo[e]indol-3-yl]carbonyl}pentacyclo[4.2.0.0$^{2,5}$.0$^{3,8}$.0$^{4,7}$]oct-1-yl)carbonyl]-2,3-dihydro-1H-benzo[e]indol-5-yl dihydrogen phosphate |
| P3 | 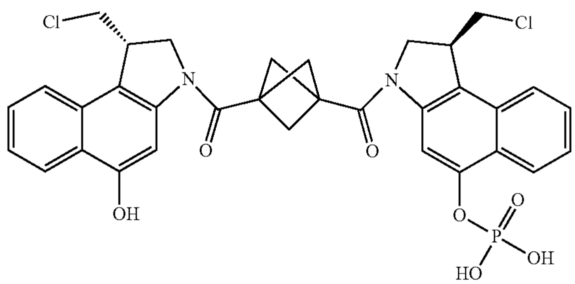 [SMILES: O=C(N1C[C@@H](CCl)c2c1cc(O)c1ccccc21)C12CC(C(=O)N3C[C@@H](CCl)c4c3cc(OP(=O)(O)O)c3ccccc43)(C1)C2] | (1S)-1-(chloromethyl)-3-[(3-{[(1S)-1-(chloromethyl)-5-hydroxy-1,2-dihydro-3H-benzo[e]indol-3-yl]carbonyl}bicyclo[1.1.1]pent-1-yl)carbonyl]-2,3-dihydro-1H-benzo[e]indol-5-yl dihydrogen phosphate |
| P4 | 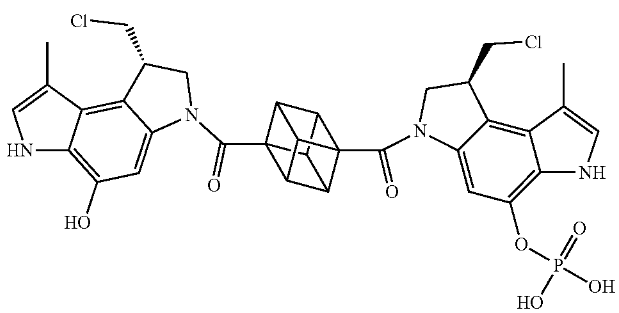 [SMILES: Cc1c[nH]c2c(O)cc3c(c12)[C@H](CCl)CN3C(=O)C12C3C4C1C1C2C3C41C(=O)N1C[C@@H](CCl)c2c1cc(OP(=O)(O)O)c1[nH]cc(C)c21] | (8S)-8-(chloromethyl)-6-[(4-{[(1S)-1-(chloromethyl)-5-hydroxy-8-methyl-1,6-dihydropyrrolo[3,2-e]indol-3(2H)-yl]carbonyl}pentacyclo[4.2.0.0$^{2,5}$.0$^{3,8}$.0$^{4,7}$]oct-1-yl)carbonyl]-1-methyl-3,6,7,8-tetra-hydropyrrolo[3,2-e]indol-4-yl dihydrogen phosphate |
| P5 | 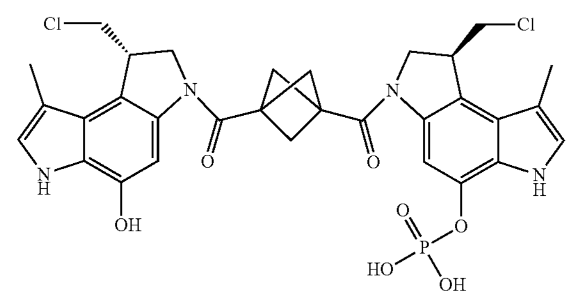 | (8S)-8-(chloromethyl)-6-[(3-{[(1S)-1-(chloromethyl)-5-hydroxy-8-methyl-1,6-dihydropyrrolo[3,2-e]indol-3(2H)-yl]carbonyl}bicyclo[1.1.1]pent-1-yl)carbonyl]-1-methyl-3,6,7,8-tetrahydropyrrolo[3,2-e]indol-4-yl dihydrogen phosphate |
| P6 | 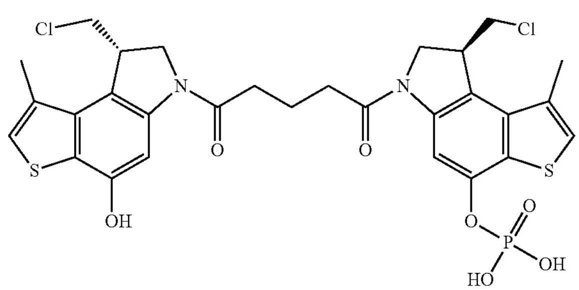 [SMILES: Cc1csc2c(O)cc3c(c12)[C@H](CCl)CN3C(=O)CCCC(=O)N1C[C@@H](CCl)c2c1cc(OP(=O)(O)O)c1scc(C)c21] | (8S)-8-(chloromethyl)-6-{5-[(8S)-8-(chloromethyl)-4-hydroxy-1-methyl-7,8-dihydro-6H-thieno[3,2-e]indol-6-yl]-5-oxopentanoyl}-1-methyl-7,8-dihydro-6H-thieno[3,2-e]indol-4-yl dihydrogen phosphate |

TABLE 1-continued

Drugs

| Payload ID | Structure | IUPAC Name |
|---|---|---|
| P7 | 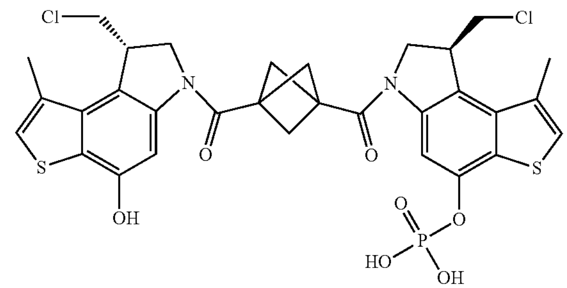 [SMILES: Cc1csc2c(O)cc3c(c12)[C@H](CCl)CN3C(=O)C12CC(C(=O)N3C[C@@H](CCl)c4c3cc(OP(=O)(O)O)c3scc(C)c43)(C1)C2] | (8S)-8-(chloromethyl)-6-[(3-{[(8S)-8-(chloromethyl)-4-hydroxy-1-methyl-7,8-dihydro-6H-thieno[3,2-e]indol-6-yl]carbonyl}bicyclo[1.1.1]pent-1-yl)carbonyl]-1-methyl-7,8-dihydro-6H-thieno[3,2-e]indol-4-yl dihydrogen phosphate |
| P8 | 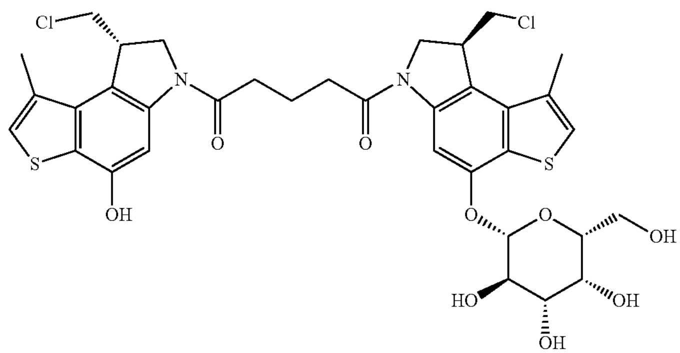 [SMILES: Cc1csc2c(O)cc3c(c12)[C@H](CCl)CN3C(=O)CCCC(=O)N1C[C@@H](CCl)c2c1cc(O[C@@H]1O[C@H](CO)[C@H](O)[C@H](O)[C@H]1O)c1scc(C)c21] | (8S)-8-(chloromethyl)-6-{5-[(8S)-8-(chloromethyl)-4-hydroxy-1-methyl-7,8-dihydro-6H-thieno[3,2-e]indol-6-yl]-5-oxopentanoyl}-1-methyl-7,8-dihydro-6H-thieno[3,2-e]indol-4-yl beta-D-galactopyranoside |
| P9 | 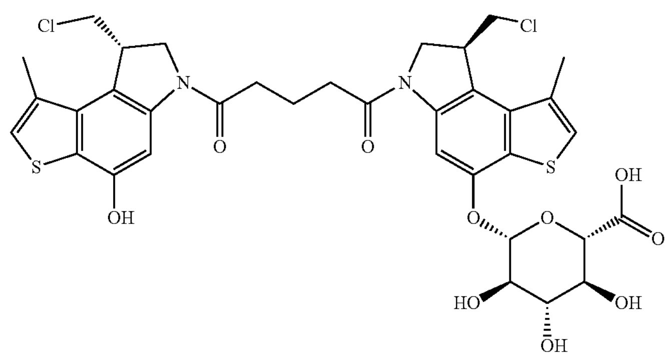 [SMILES: Cc1csc2c(O)cc3c(c12)[C@H](CCl)CN3C(=O)CCCC(=O)N1C[C@@H](CCl)c2c1cc(O[C@@H]1O[C@H](C(=O)O)[C@@H](O)[C@H](O)[C@H]1O)c1scc(C)c21] | (8S)-8-(chloromethyl)-6-{5-[(8S)-8-(chloromethyl)-4-hydroxy-1-methyl-7,8-dihydro-6H-thieno[3,2-e]indol-6-yl]-5-oxopentanoyl}-1-methyl-7,8-dihydro-6H-thieno[3,2-e]indol-4-yl beta-D-glucopyranosiduronic acid |

In some embodiments, the drug is P5 ((8S)-8-(chloromethyl)-6-[(3-{[(1S)-1-(chloromethyl)-5-hydroxy-8-methyl-1,6-dihydropyrrolo[3,2-e]indol-3(2H)-yl]carbonyl}bicyclo[1.1.1]pent-1-yl)carbonyl]-1-methyl-3,6,7,8-tetrahydropyrrolo[3,2-e]indol-4-yl dihydrogen phosphate).

In some aspects of the invention, the cytotoxic agent can be made using a liposome or biocompatible polymer. The antibodies as described herein can be conjugated to the biocompatible polymer to increase serum half-life and bioactivity, and/or to extend in vivo half-lives. Examples of biocompatible polymers include water-soluble polymer, such as polyethylene glycol (PEG) or its derivatives thereof and zwitterion-containing biocompatible polymers (e.g., a phosphorylcholine containing polymer).

C. Linkers

Site specific ADCs of the invention are prepared using a linker to link or conjugate a drug to an antibody. A linker is a bifunctional compound which can be used to link a drug and an antibody to form an antibody drug conjugate (ADC). Such conjugates allow the selective delivery of drugs to tumor cells. Suitable linkers include, for example, cleavable and non-cleavable linkers. A cleavable linker is typically susceptible to cleavage under intracellular conditions. Major mechanisms by which a conjugated drug is cleaved from an antibody include hydrolysis in the acidic pH of the lysosomes (hydrazones, acetals, and cis-aconitate-like amides), peptide cleavage by lysosomal enzymes (the cathepsins and other lysosomal enzymes), and reduction of disulfides. As a result of these varying mechanisms for cleavage, mechanisms of linking the drug to the antibody also vary widely and any suitable linker can be used.

Suitable cleavable linkers include, but are not limited to, a peptide linker, such as mc-vc, MalPeg6-vc, and m(H20) c-vc, cleavable by an intracellular protease (Table 2 infra). In specific embodiments, the linker is a cleavable linker such that the payload can induce a bystander effect once the linker is cleaved. The bystander effect is when a membrane permeable drug is released from the antibody (i.e., by cleaving of a cleavable liner) and crosses the cellular membrane and, upon diffusion, induce killing of cells surrounding the cell that initially internalized the ADC.

Suitable non-cleavable linkers include, but are not limited to, mc, MalPeg6, Mal-PEG2, Mal-PEG3 and m(H20)c (Table 2 infra).

Other suitable linkers include linkers hydrolyzable at a specific pH or a pH range, such as a hydrazone linker. Additional suitable cleavable linkers include disulfide linkers. The linker may be covalently bound to the antibody to such an extent that the antibody must be degraded intracellularly in order for the drug to be released e.g. the mc linker and the like.

In particular aspects of the invention, the linker in the site specific ADCs of the invention are cleavable and may be vc, MalPeg6-vc-PABC or MalPeg6-vc-PABC-DMAE.

Many of the therapeutic agents conjugated to antibodies have little, if any, solubility in water and that can limit drug loading on the conjugate due to aggregation of the conjugate. One approach to overcoming this is to add solublizing groups to the linker. Conjugates made with a linker consisting of PEG and a dipeptide can been used, including those having a PEG di-acid, thiol-acid, or maleimide-acid attached to the antibody, a dipeptide spacer, and an amide bond to the amine of an anthracycline or a duocarmycin analogue. Another example is a conjugate prepared with a PEG-containing linker disulfide bonded to a cytotoxic agent and amide bonded to an antibody. Approaches that incorporate PEG groups may be beneficial in overcoming aggregation and limits in drug loading.

TABLE 2

Linkers

| Name | Structure |
|---|---|
| vc (MC-vc-PAB) | 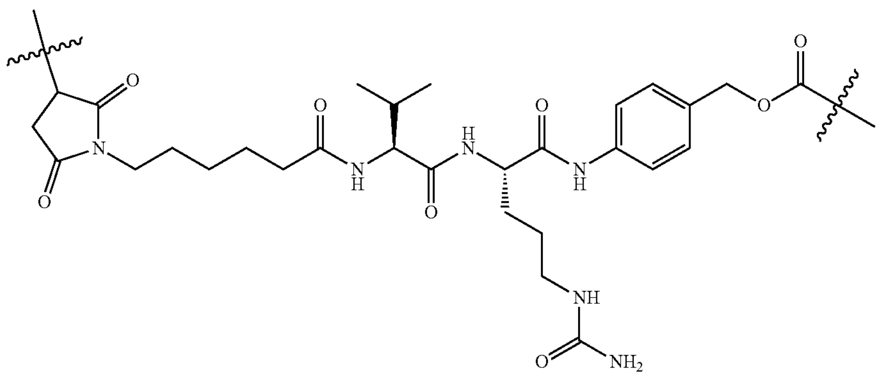 [SMILES: *C(=O)OCc1ccc(NC(=O)[C@H](CCCNC(N)=O)NC(=O)[C@@H](NC(=O)CCCCCN2C(=O)CC(*)C2=O)C(C)C)cc1] |
| mc | 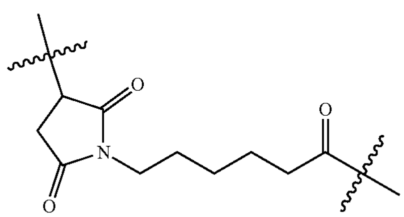 [SMILES: *C(=O)CCCCCN1C(=O)CC(*)C1=O] |
| MalPeg6 | 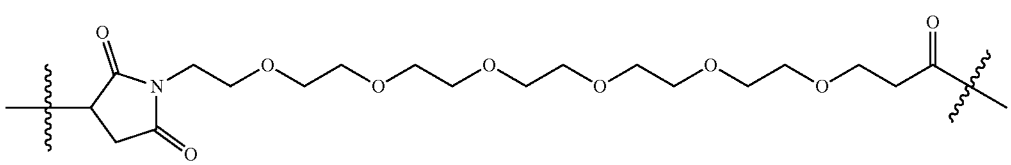 [SMILES: *C(=O)CCOCCOCCOCCOCCOCCOCCN1C(=O)CC(*)C1=O] |
| m(H20)c | |
| m(H20)c | |

TABLE 2-continued
Linkers
| Name | Structure |
|---|---|
| m(H2O)c-vc (m(H2O)c-vc-PAB) | 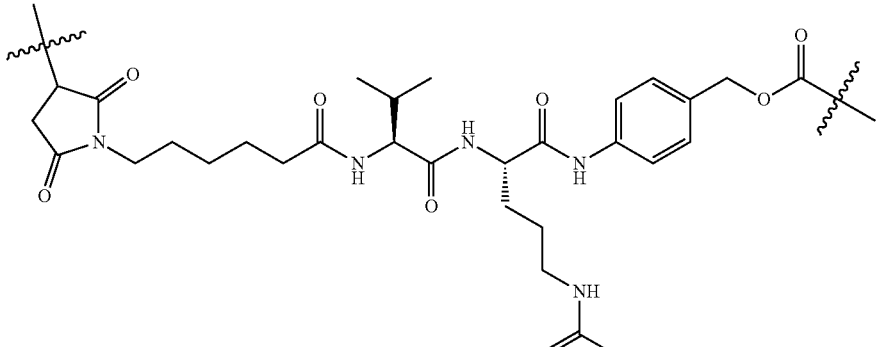 |
Linkers are attached to the monoclonal antibody via the left side of the molecule and the drug via the right side of the molecule as depicted in Table 2.
Additional non-limiting examples of linkers are provided in Table 3.
TABLE 3
Additional Linkers
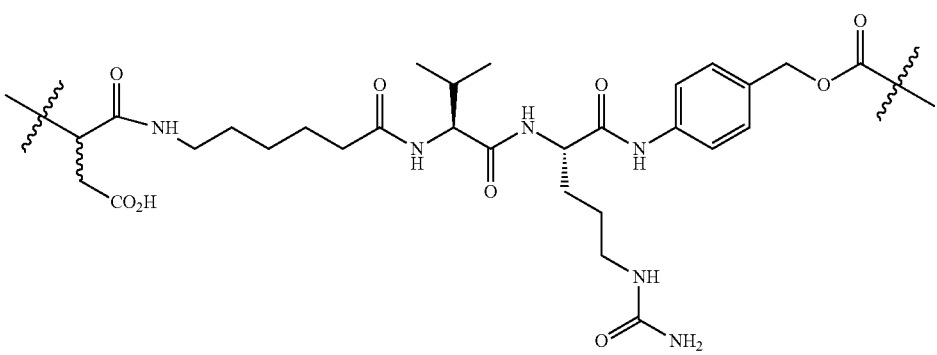 [SMILES: *C(=O)OCc1ccc(NC(=O)[C@H](CCCNC(N)=O)NC(=O)[C@@H](NC(=O)CCCCCNC(=O)C(*)CC(=O)O)C(C)C)cc1]
LP1-linker
LP2-linker

TABLE 3-continued

Additional Linkers

LP3-linker 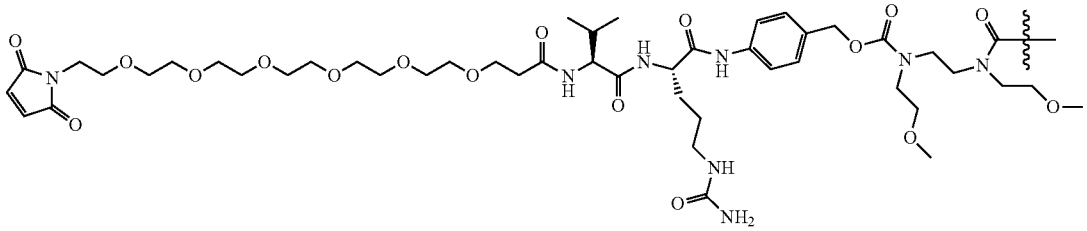 [SMILES: *C(=O)N(CCOC)CCN(CCOC)C(=O)OCc1ccc(NC(=O)[C@H](CCCNC(N)=O)NC(=O)[C@@H](NC(=O)CCOCCOCCOCCOCCOCCOCCN2C(=O)C=CC2=O)C(C)C)cc1]

LP4-linker 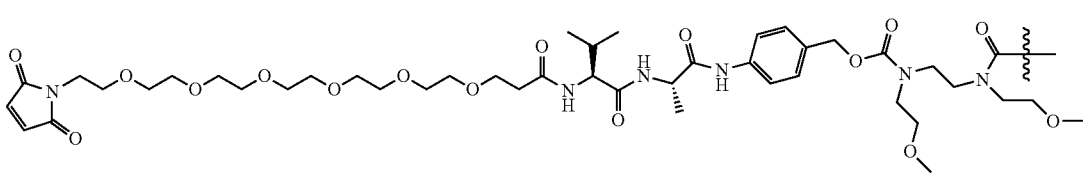 [SMILES: *C(=O)N(CCOC)CCN(CCOC)C(=O)OCc1ccc(NC(=O)[C@H](C)NC(=O)[C@@H](NC(=O)CCOCCOCCOCCOCCOCCOCCN2C(=O)C=CC2=O)C(C)C)cc1]

In certain embodiments, the antibody drug conjugates comprise linkers LP1, LP2, LP3 or LP4 (Table 3).

In certain embodiment, the antibody of the invention is conjugated to a thiol-reactive agent in which the reactive group is, for example, a maleimide, an iodoacetamide, a pyridyl disulfide, or other thiol-reactive conjugation partner (Haugland, 2003, Molecular Probes Handbook of Fluorescent Probes and Research Chemicals, Molecular Probes, Inc.; Brinkley, 1992, Bioconjugate Chem. 3:2; Garman, 1997, Non-Radioactive Labelling: A Practical Approach, Academic Press, London; Means (1990) Bioconjugate Chem. 1:2; Hermanson, G. in Bioconjugate Techniques (1996) Academic Press, San Diego, pp. 40-55, 643-671).

PCT publication no. WO 2018/025168, which is incorporated herein by reference in its entirety, discloses non-maleimide based linkers and linker components that are useful in the ADCs of the present invention and provides methods of preparing these linkers.

In certain embodiments, the invention provides an antibody drug conjugate of the formula Ab-(L-D), wherein (a) Ab is an antibody that binds to a specific target; and (b) L-D is a linker-drug moiety, wherein L is a linker, and D is a drug.

In certain embodiments, the Ab-(L-D) comprises a succinimide group, a maleimide group, a hydrolyzed succinimide group, or a hydrolyzed maleimide group.

In certain embodiments, the Ab-(L-D) comprises a maleimide group, a hydrolyzed maleimide group or hydrolyzed Peg-maleimides. Maleimides such as N-ethylmaleimide are considered to be specific to sulfhydryl groups, especially at pH values below 7, where other groups are protonated.

In certain embodiments, the Ab-(L-D) comprises 6-maleimidocaproyl (MC), maleimidopropanoyl (MP), valine-citrulline (val-cit; vc), methoxy-polyethylene glycol maleimide 6 (MalPeg6), p-aminobenzylcarbamate (PABC), dimethylaminoethanol (DMAE), alanine-phenylalanine (ala-phe), p-aminobenzyloxycarbonyl (PAB), N-Succinimidyl (4-iodo-acetyl) aminobenzoate (SIAB), or 6-maleimidocaproyl-valine-citrulline-p-aminobenzyloxycarbonyl (MC-vc-PAB) or a combination thereof. In some embodiments, the linker comprises a combination of MalPeg6, vc, PABC, and DMAE. In some embodiments, the linker comprises MalPeg6-vc-PABC-DMAE.

In certain embodiments, the linker-drug (L-D) component of the ADC comprises:

(LP1)

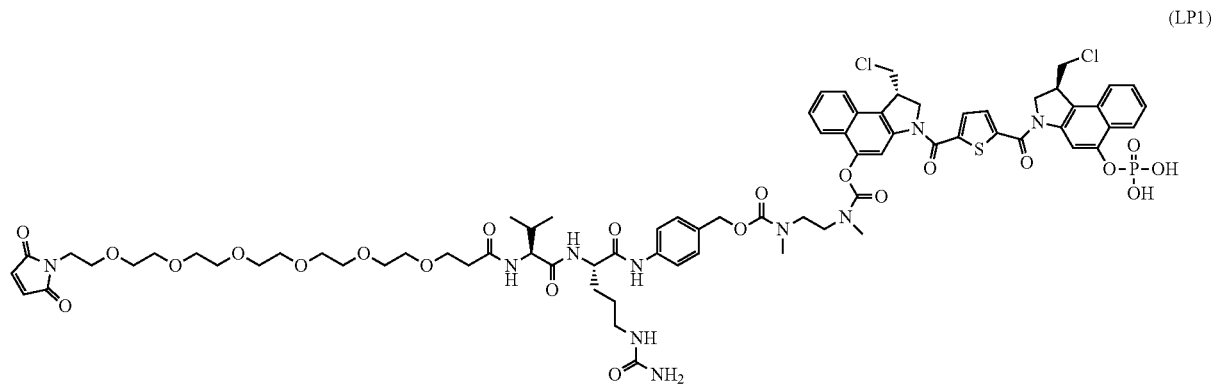 [SMILES: CC(C)[C@H](NC(=O)CCOCCOCCOCCOCCOCCOCCN1C(=O)C=CC1=O)C(=O)N[C@@H](CCCNC(N)=O)C(=O)Nc1ccc(COC(=O)N(C)CCN(C)C(=O)Oc2cc3c(c4ccccc24)[C@H](CCl)CN3C(=O)c2ccc(C(=O)N3C[C@@H](CCl)c4c3cc(OP(=O)(O)O)c3ccccc43)s2)cc1]

Ab is an antibody that binds to a specific target; and (b) L-D is a linker-drug moiety, wherein L is a linker, and D is a drug.

(N-[1-(2,5-dioxo-2,5-dihydro-1H-pyrrol-1-yl)-21-oxo-3,6,9,12,15,18-hexaoxahenicosan-21-yl]-L valyl-N$^5$-carbamoyl-N-[4-({[(2-{[({(1S)-1-(chloromethyl)-3-[(5-{[(1S)-1-(chloromethyl)-5-(phosphonooxy)-1,2-dihydro-3H-benzo[e]indol-3-yl]carbonyl}thiophen-2-yl)carbonyl]-2,3-dihydro-1H-benzo[e]indol-5-yl}oxy)carbonyl](methyl)amino}ethyl)(methyl)carbamoyl]oxy}methyl)phenyl]-L-ornithinamide).

In certain embodiments, the linker-drug (L-D) component of the ADC comprises:

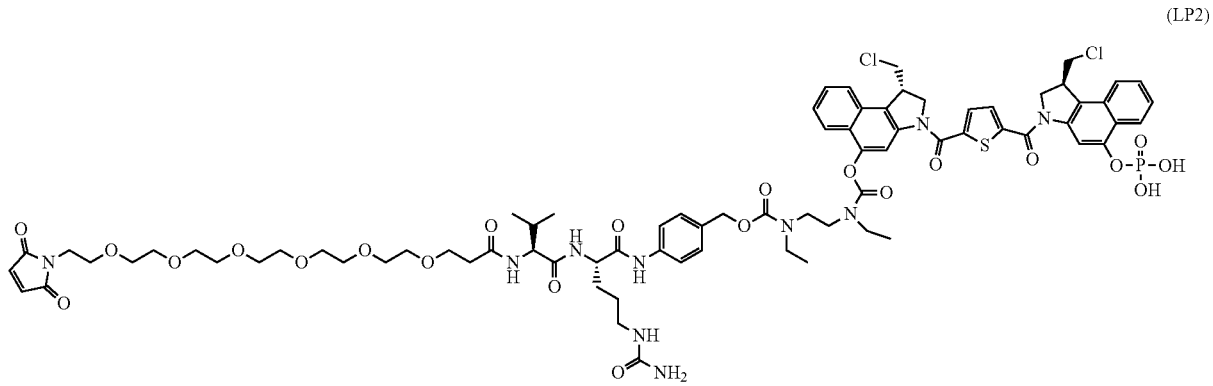 [SMILES: CCN(CCN(CC)C(=O)Oc1cc2c(c3ccccc13)[C@H](CCl)CN2C(=O)c1ccc(C(=O)N2C[C@@H](CCl)c3c2cc(OP(=O)(O)O)c2ccccc32)s1)C(=O)OCc1ccc(NC(=O)[C@H](CCCNC(N)=O)NC(=O)[C@@H](NC(=O)CCOCCOCCOCCOCCOCCOCCN2C(=O)C=CC2=O)C(C)C)cc1]

(LP2)

(N-[1-(2,5-dioxo-2,5-dihydro-1H-pyrrol-1-yl)-21-oxo-3,6,9,12,15,18-hexaoxahenicosan-21-yl]-L-valyl-$N^5$-carbamoyl-N-[4-({[(2-{[({(1S)-1-(chloromethyl)-3-[(5-{[(1S)-1-(chloromethyl)-5-(phosphonooxy)-1,2-dihydro-3H-benzo[e]indol-3-yl]carbonyl}thiophen-2-yl)carbonyl]-2,3-dihydro-1H-benzo[e]indol-5-yl}oxy)carbonyl](ethyl)amino}ethyl)(ethyl)carbamoyl]oxy}methyl)phenyl]-L-ornithinamide).

In certain embodiments, the linker-drug (L-D) component of the ADC comprises:

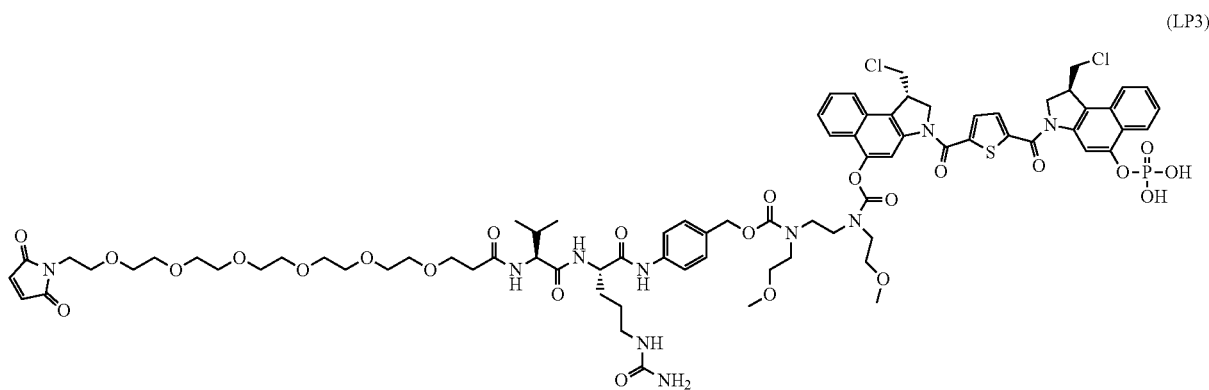 [SMILES: COCCN(CCN(CCOC)C(=O)Oc1cc2c(c3ccccc13)[C@H](CCl)CN2C(=O)c1ccc(C(=O)N2C[C@@H](CCl)c3c2cc(OP(=O)(O)O)c2ccccc32)s1)C(=O)OCc1ccc(NC(=O)[C@H](CCCNC(N)=O)NC(=O)[C@@H](NC(=O)CCOCCOCCOCCOCCOCCOCCN2C(=O)C=CC2=O)C(C)C)cc1]

(LP3)

(N-[1-(2,5-dioxo-2,5-dihydro-1H-pyrrol-1-yl)-21-oxo-3,6,9,12,15,18-hexaoxahenicosan-21-yl]-L-valyl-$N^5$-carbamoyl-$N^5$-(4-{7-[({(1S)-1-(chloromethyl)-3-[(5-{[(1S)-1-(chloromethyl)-5-(phosphonooxy)-1,2-dihydro-3H-benzo[e]indol-3-yl]carbonyl}thiophen-2-yl)carbonyl]-2,3-dihydro-1H-benzo[e]indol-5-yl}oxy)carbonyl]-4-(2-methoxyethyl)-3-oxo-2,10-dioxa-4,7-diazaundec-1-yl}phenyl)-L-ornithinamide).

In certain embodiments, the linker-drug (L-D) component of the ADC comprises:

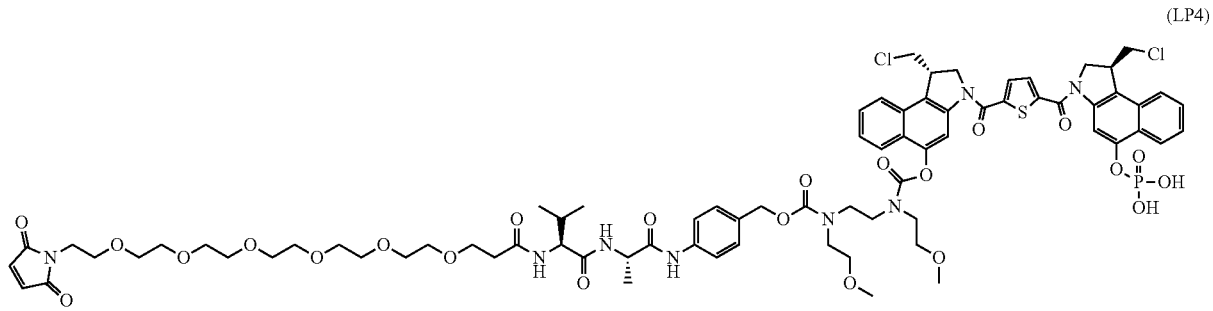 [SMILES: COCCN(CCN(CCOC)C(=O)Oc1cc2c(c3ccccc13)[C@H](CCl)CN2C(=O)c1ccc(C(=O)N2C[C@@H](CCl)c3c2cc(OP(=O)(O)O)c2ccccc32)s1)C(=O)OCc1ccc(NC(=O)[C@H](C)NC(=O)[C@@H](NC(=O)CCOCCOCCOCCOCCOCCOCCN2C(=O)C=CC2=O)C(C)C)cc1]

(LP4)

(N-[1-(2,5-dioxo-2,5-dihydro-1H-pyrrol-1-yl)-21-oxo-3,6,
9,12,15,18-hexaoxahenicosan-21-yl]-L-valyl-N-(4-{7-[({
(1S)-1-(chloromethyl)-3-[(5-{[(1S)-1-(chloromethyl)-5-
(phosphonooxy)-1,2-dihydro-3H-benzo[e]indol-3-yl]
carbonyl}thiophen-2-yl)carbonyl]-2,3-dihydro-1H-benzo[e]
indol-5-yl}oxy)carbonyl]-4-(2-methoxyethyl)-3-oxo-2,10-
dioxa-4,7-diazaundec-1-yl}phenyl)-L-alaninamide).

In certain embodiments, the linker-drug (L-D) component of the ADC comprises:

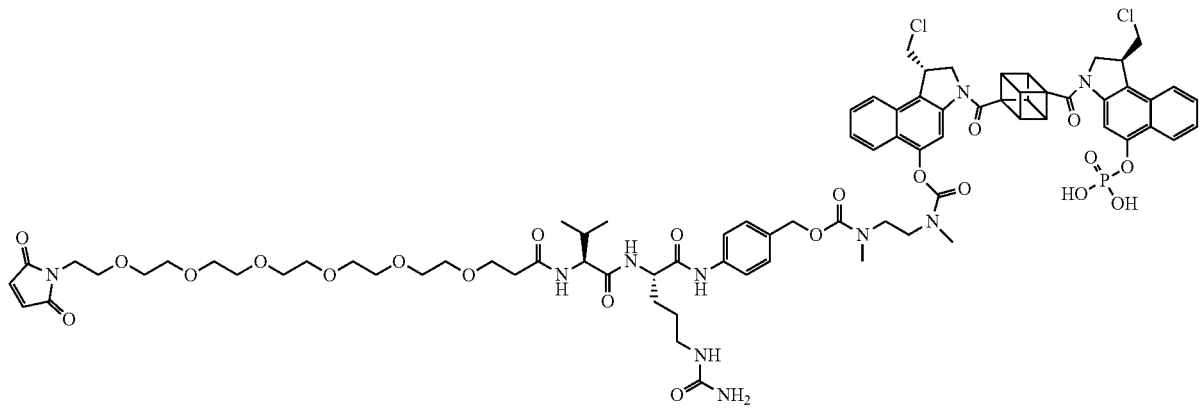

(LP5)

(N-[1-(2,5-dioxo-2,5-dihydro-1H-pyrrol-1-yl)-21-oxo-3,6,
9,12,15,18-hexaoxahenicosan-21-yl]-L-valyl-$N^5$-carbam-
oyl-N-[4-({[(2-{[({(1S)-1-(chloromethyl)-3-[(4-{[(1S)-1-
(chloromethyl)-5-(phosphonooxy)-1,2-dihydro-3H-benzo
[e]indol-3-yl]carbonyl}pentacyclo[4.2.0.0$^{2,5}$.0$^{3,8}$.0$^{4,7}$]oct-1-
yl)carbonyl]-2,3-dihydro-1H-benzo[e]indol-5-yl}oxy)
carbonyl](methyl)amino}ethyl)(methyl)carbamoyl]
oxy}methyl)phenyl]-L-ornithinamide).

In certain embodiments, the linker-drug (L-D) component of the ADC comprises:

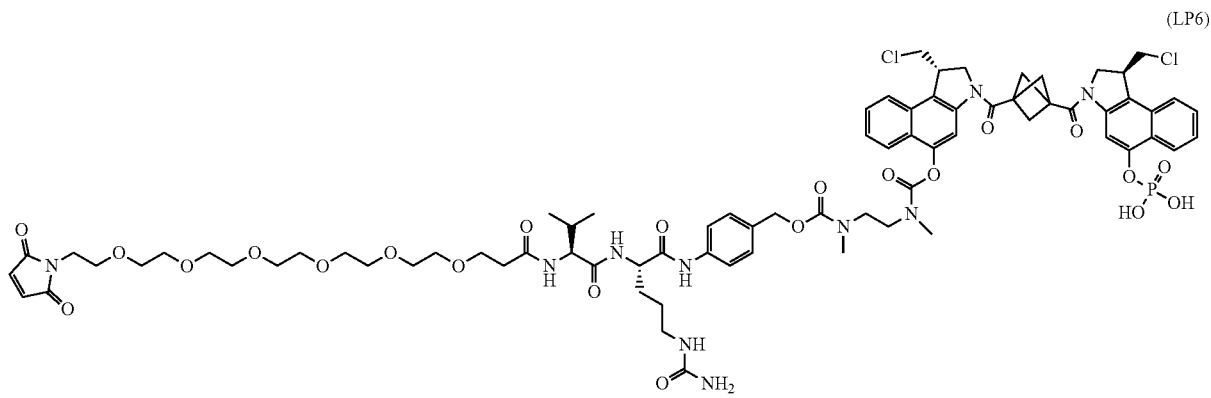 [SMILES: CC(C)[C@H](NC(=O)CCOCCOCCOCCOCCOCCOCCN1C(=O)C=CC1=O)C(=O)N[C@@H](CCCNC(N)=O)C(=O)Nc1ccc(COC(=O)N(C)CCN(C)C(=O)Oc2cc3c(c4ccccc24)[C@H](CCl)CN3C(=O)C23CC(C(=O)N4C[C@@H](CCl)c5c4cc(OP(=O)(O)O)c4ccccc54)(C2)C3)cc1]

(LP6)

(N-[1-(2,5-dioxo-2,5-dihydro-1H-pyrrol-1-yl)-21-oxo-3,6,
9,12,15,18-hexaoxahenicosan-21-yl]-L-valyl-$N^5$-carbam-
oyl-N-[4-({[(2-{[({(1S)-1-(chloromethyl)-3-[(3-{[(1S)-1-
(chloromethyl)-5-(phosphonooxy)-1,2-dihydro-3H-benzo
[e]indol-3-yl]carbonyl}bicyclo[1.1.1]pent-1-yl)carbonyl]-2,
3-dihydro-1H-benzo[e]indol-5-yl}oxy)carbonyl](methyl)
amino}ethyl)(methyl)carbamoyl]oxy}methyl)phenyl]-L-
ornithinamide).

In certain embodiments, the linker-drug (L-D) component of the ADC comprises:

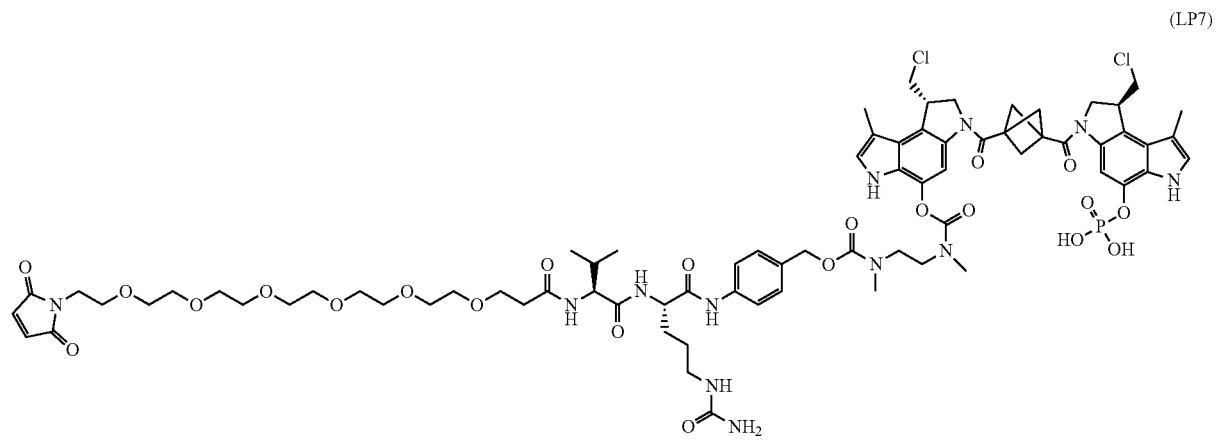

(LP7)

(N-[1-(2,5-dioxo-2,5-dihydro-1H-pyrrol-1-yl)-21-oxo-3,6,9,12,15,18-hexaoxahenicosan-21-yl]-L-valyl-N-carbamoyl-N-[4-({[(2-{[({(8S)-8-(chloromethyl)-6-[(3-{[(1S)-1-(chloromethyl)-8-methyl-5-(phosphonooxy)-1,6-dihydropyrrolo[3,2-e]indol-3(2H)-yl]carbonyl}bicyclo[1.1.1]pent-1-yl)carbonyl]-1-methyl-3,6,7,8-tetrahydropyrrolo[3,2-e]indol-4-yl}oxy)carbonyl](methyl)amino}ethyl)(methyl)carbamoyl]oxy}methyl)phenyl]-L-ornithinamide).

In certain embodiments, the linker-drug (L-D) component of the ADC comprises:

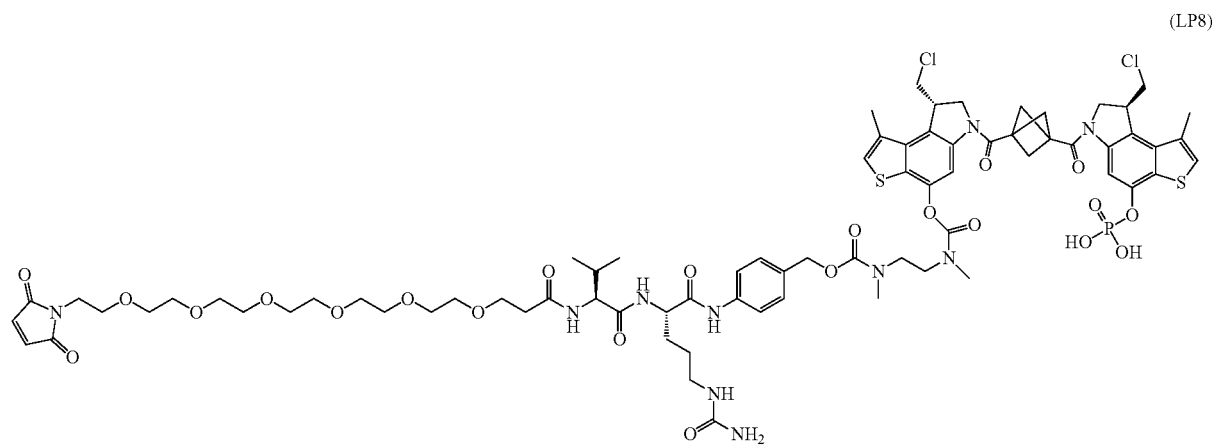 [SMILES: Cc1csc2c(OC(=O)N(C)CCN(C)C(=O)OCc3ccc(NC(=O)[C@H](CCCNC(N)=O)NC(=O)[C@@H](NC(=O)CCOCCOCCOCCOCCOCCOCCN4C(=O)C=CC4=O)C(C)C)cc3)cc3c(c12)[C@H](CCl)CN3C(=O)C12CC(C(=O)N3C[C@@H](CCl)c4c3cc(OP(=O)(O)O)c3scc(C)c43)(C1)C2]

(LP8)

(N-[1-(2,5-dioxo-2,5-dihydro-1H-pyrrol-1-yl)-21-oxo-3,6,9,12,15,18-hexaoxahenicosan-21-yl]-L-valyl-$N^5$-carbamoyl-N-[4-({[(2-{[({(8S)-8-(chloromethyl)-6-[(3-{[(8S)-8-(chloromethyl)-1-methyl-4-(phosphonooxy)-7,8-dihydro-6H-thieno[3,2-e]indol-6-yl]carbonyl}bicyclo[1.1.1]pent-1-yl)carbonyl]-1-methyl-7,8-dihydro-6H-thieno[3,2-e]indol-4-yl}oxy)carbonyl](methyl)amino}ethyl)(methyl)carbamoyl]oxy}methyl)-phenyl]-L-ornithinamide).

In certain embodiments, the linker-drug (L-D) component of the ADC comprises:

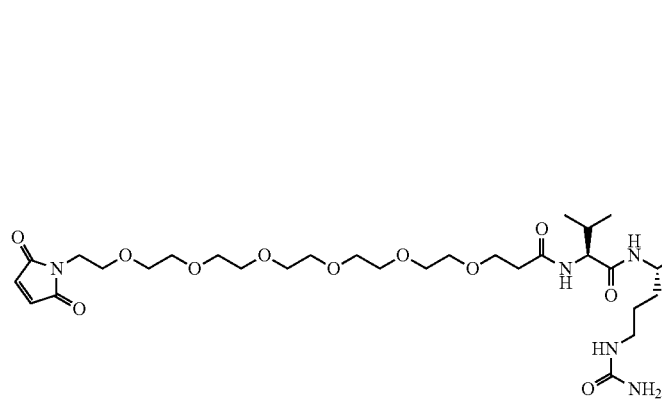
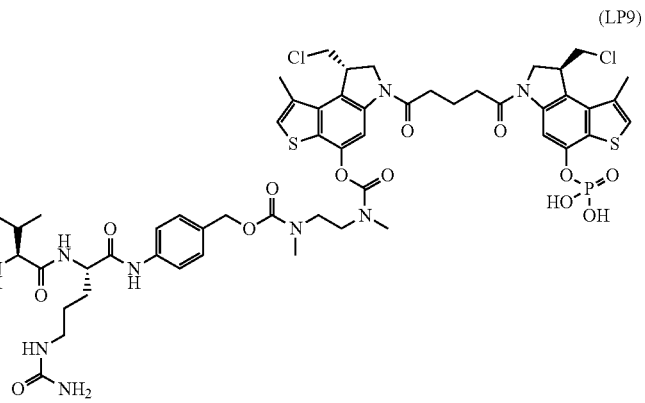

(LP9)

(N-[1-(2,5-dioxo-2,5-dihydro-1H-pyrrol-1-yl)-21-oxo-3,6,9,12,15,18-hexaoxahenicosan-21-yl]-L-valyl-N⁵-carbamoyl-N-[4-({[{2-[({[(8S)-8-(chloromethyl)-6-{5-[(8S)-8-(chloromethyl)-1-methyl-4-(phosphonooxy)-7,8-dihydro-6H-thieno[3,2-e]indol-6-yl]-5-oxopentanoyl}-1-methyl-7,8-dihydro-6H-thieno[3,2-e]indol-4-yl]oxy}carbonyl)(methyl)amino]ethyl}(methyl)carbamoyl]oxy}methyl)phenyl]-L-ornithinamide).

In certain embodiments, the linker-drug (L-D) component of the ADC comprises:

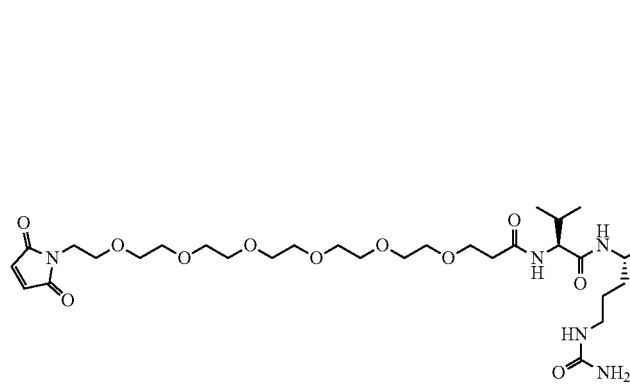
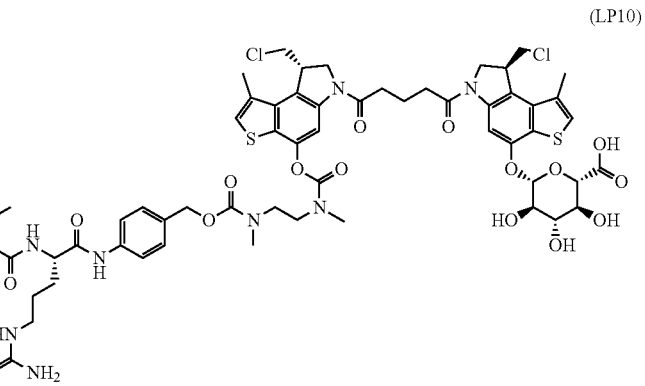

(LP10)

(N-[1-(2,5-dioxo-2,5-dihydro-1H-pyrrol-1-yl)-21-oxo-3,6,9,12,15,18-hexaoxahenicosan-21-yl]-L-valyl-N⁵-carbamoyl-N-[4-({[{2-[({[(8S)-8-(chloromethyl)-6-{5-[(8S)-8-(chloromethyl)-4-(beta-D-glucopyranuronosyloxy)-1-methyl-7,8-dihydro-6H-thieno[3,2-e]indol-6-yl]-5-oxopentanoyl}-1-methyl-7,8-dihydro-6H-thieno[3,2-e]indol-4-yl]oxy}carbonyl)(methyl)amino]ethyl}(methyl)carbamoyl]oxy}methyl)phenyl]-L-ornithinamide).

D. Methods of Preparing Site Specific ADCs

Also provided are methods for preparing antibody drug conjugates of the present invention. For example, a process for producing a site specific ADC as disclosed herein can include (a) linking the linker to the drug; (b) conjugating the linker drug moiety to the antibody; and (c) purifying the antibody drug conjugate.

The ADCs of the present invention use site specific methods to conjugate the antibody to the drug payload. In one embodiment, the site specific conjugation occurs through one or more cysteine residues that have been engineered into an antibody constant region. Methods of preparing antibodies for site specific conjugation through cysteine residues can be performed as described in PCT Publication No. WO2013/093809, which is incorporated by reference in its entirety. The engineered cysteine can be at position 334 and/or position 392 (according to the numbering of the Eu index of Kabat). Additionally, one or more of the following positions can be altered to be a cysteine and thus also serve as a site for conjugation: a) on the heavy chain constant region, residues 246, 249, 265, 267, 270, 276, 278, 283, 290, 292, 293, 294, 300, 302, 303, 314, 315, 318, 320, 327, 332, 333, 336, 345, 347, 354, 355, 358, 360, 362, 370, 373, 376, 378, 380, 382, 386, 388, 390, 393, 401, 404, 411, 413, 414, 416, 418, 419, 421, 428, 431, 432, 437, 438, 439, 443, and 444 (according to the Eu index of Kabat for the heavy chain) and/or b) on the light chain constant region, residues 110, 111, 125, 149, 155, 158, 161, 183, 185, 188, 189, 191, 197, 205, 206, 207, 208, and 210 (according to the Kabat numbering for light chain).

In certain embodiments, the one or more positions that may be altered to be a cysteine on the heavy chain constant region are 334 or 392 (according to the Eu index of Kabat for the heavy chain). In a more specific embodiment, positions 334 and 392 on the heavy chain constant region according to the Eu index of Kabat are altered to cysteine for conjugation.

In certain embodiments, the one or more positions that may be altered to be a cysteine a) on the heavy chain constant region are 290, 334, 392 and/or 347 (according to the Eu index of Kabat for the heavy chain) and/or b) on the light chain constant region is 183 (according to the Kabat numbering for the light chain).

Optimal reaction conditions for formation of a conjugate may be empirically determined by variation of reaction variables such as temperature, pH, linker-payload moiety input, and additive concentration. Conditions suitable for conjugation of other drugs may be determined by those skilled in the art without undue experimentation. Site specific conjugation through engineered cysteine residues is exemplified in Examples 1 and 3 infra.

To further increase the number of drug molecules per antibody drug conjugate, the drug may be conjugated to polyethylene glycol (PEG), including straight or branched polyethylene glycol polymers and monomers. A PEG monomer is of the formula: —($CH_2CH_2O$)—. Drugs and/or peptide analogs may be bound to PEG directly or indirectly, i.e. through appropriate spacer groups such as sugars. A PEG-antibody drug composition may also include additional lipophilic and/or hydrophilic moieties to facilitate drug stability and delivery to a target site in vivo. Representative methods for preparing PEG-containing compositions may be found in, e.g., U.S. Pat. Nos. 6,461,603; 6,309,633; and 5,648,095.

Following conjugation, the conjugates may be separated and purified from unconjugated reactants and/or aggregated forms of the conjugates by conventional methods. This can include processes such as size exclusion chromatography (SEC), ultrafiltration/diafiltration, ion exchange chromatography (IEC), chromatofocusing (CF) HPLC, FPLC, or Sephacryl S-200 chromatography. The separation may also be accomplished by hydrophobic interaction chromatography (HIC). Suitable HIC media includes Phenyl Sepharose 6 Fast Flow chromatographic medium, Butyl Sepharose 4 Fast Flow chromatographic medium, Octyl Sepharose 4 Fast Flow chromatographic medium, Toyopearl Ether-650M chromatographic medium, Macro-Prep methyl HIC medium or Macro-Prep t-Butyl HIC medium.

Table 4 shows ADCs with antibodies to CD33, Her2 and 1.1 used to generate data in the Examples Section. The site specific CD33, Her2 and 1.1 ADCs shown in Table 4 are examples of site specific ADCs of the invention.

To make a site specific ADC of the invention any antibody disclosed herein can be conjugated using site specific techniques to any drug disclosed herein via any linker disclosed herein. In certain embodiments, the linker is cleavable (e.g., vc). In certain embodiments, the drug is a CPI or CBI dimer.

Polypeptides, antibodies and ADCs of the invention may be site-specific conjugated through an engineered cysteine at position 334 (according to the numbering of the Eu index of Kabat). The IgG1 antibody heavy chain CH2 region is shown in SEQ ID NO:25 (Table 18; K334, using the numbering of the Eu index of Kabat, is bold and underlined). The IgG1 antibody heavy chain CH2 and CH3 regions are shown in SEQ ID NO:26 (Table 18; K334 and K392, using the numbering of the Eu index of Kabat, are bold and underlined).

TABLE 4

Exemplified ADCs

CD33-K334C-CPI (SEQ ID Nos: 23 and 32)

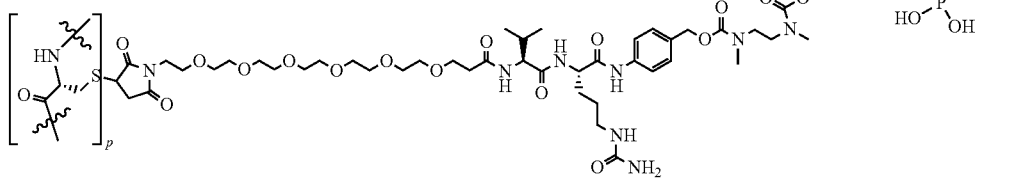

CD33-K392C-CPI (SEQ ID Nos: 23 and 33)

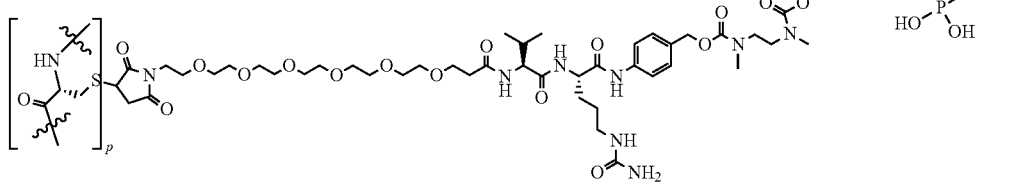

TABLE 4-continued

Exemplified ADCs

| Name | Structure |
|---|---|
| CD33-K334C/K392C-CPI (SEQ ID Nos: 23 and 34) | |
| Her2-K334C-CPI (Trastuzumab with Cys substituion) | |
| 1.1-K334C-CPI (Trastuzumab with Cys substituion) | |

In the above table, the bracketed portion of the structural representations of the compounds represent the amino acid within the peptide sequence of the antibodies to which the respective linker payloads are conjugated.

2. Formulations and Uses

Polypeptides, antibodies, and ADCs described herein can be formulated as pharmaceutical formulations. The pharmaceutical formulation may further comprise pharmaceutically acceptable carriers, excipients, or stabilizers. Further, the compositions can include more than one of the ADCs disclosed herein.

The compositions used in the present invention can further include pharmaceutically acceptable carriers, excipients, or stabilizers (Remington: The Science and practice of Pharmacy 21st Ed., 2005, Lippincott Williams and Wilkins, Ed. K. E. Hoover), in the form of lyophilized formulations or aqueous solutions. Acceptable carriers, excipients, or stabilizers are nontoxic to recipients at the dosages and concentrations, and may include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrans; chelating agents such as EDTA; sugars such as sucrose, mannitol, trehalose or sorbitol; salt-forming counter-ions such as sodium; metal complexes (e. g. Zn-protein complexes); and/or non-ionic surfactants such as TWEEN™, PLURONICS™ or polyethylene glycol (PEG). "Pharmaceutically acceptable salt" as used herein refers to pharmaceutically acceptable organic or inorganic salts of a molecule or macromolecule. Pharmaceutically acceptable excipients are further described herein.

Various formulations of one or more ADCs of the invention may be used for administration including, but not limited to formulations comprising one or more pharmaceutically acceptable excipients. Pharmaceutically acceptable excipients are known in the art, and are relatively inert substances that facilitate administration of a pharmacologically effective substance. For example, an excipient can give form or consistency, or act as a diluent. Suitable excipients include but are not limited to stabilizing agents, wetting and emulsifying agents, salts for varying osmolarity, encapsulating agents, buffers, and skin penetration enhancers. Excipients as well as formulations for parenteral and non-parenteral drug delivery are set forth in Remington, The Science and Practice of Pharmacy 20th Ed. Mack Publishing, 2000.

In some aspects of the invention, these agents are formulated for administration by injection (e.g., intraperitoneally, intravenously, subcutaneously, intramuscularly, etc.). Accordingly, these agents can be combined with pharmaceutically acceptable vehicles such as saline, Ringer's solution, dextrose solution, and the like. The particular dosage regimen, i.e., dose, timing and repetition, will depend on the particular individual and that individual's medical history.

Therapeutic formulations of the ADCs of the invention are prepared for storage by mixing an ADC having the desired degree of purity with optional pharmaceutically acceptable carriers, excipients or stabilizers (Remington, The Science and Practice of Pharmacy 21st Ed. Mack Publishing, 2005), in the form of lyophilized formulations or aqueous solutions. Acceptable carriers, excipients, or stabilizers are nontoxic to recipients at the dosages and concentrations employed, and may include buffers such as phosphate, citrate, and other organic acids; salts such as sodium chloride; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens, such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e. g. Zn-protein complexes); and/or non-ionic surfactants such as TWEEN™, PLURONICS™ or polyethylene glycol (PEG).

Liposomes containing the ADCs of the invention can be prepared by methods known in the art, such as described in Eppstein, et al., 1985, PNAS 82:3688-92; Hwang, et al., 1908, PNAS 77:4030-4; and U.S. Pat. Nos. 4,485,045 and 4,544,545. Liposomes with enhanced circulation time are disclosed in U.S. Pat. No. 5,013,556. Particularly useful liposomes can be generated by the reverse phase evaporation method with a lipid composition including phosphatidylcholine, cholesterol and PEG-derivatized phosphatidylethanolamine (PEG-PE). Liposomes are extruded through filters of defined pore size to yield liposomes with the desired diameter.

The active ingredients may also be entrapped in microcapsules prepared, for example, by coacervation techniques or by interfacial polymerization, for example, hydroxymethylcellulose or gelatin-microcapsules and poly-(methylmethacrylate) microcapsules, respectively, in colloidal drug delivery systems (for example, liposomes, albumin microspheres, microemulsions, nanoparticles and nanocapsules) or in macroemulsions. Such techniques are disclosed in Remington, The Science and Practice of Pharmacy 21st Ed. Mack Publishing, 2005.

Sustained-release preparations may be prepared. Suitable examples of sustained-release preparations include semipermeable matrices of solid hydrophobic polymers containing the antibody, which matrices are in the form of shaped articles, e. g. films, or microcapsules. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and 7 ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), sucrose acetate isobutyrate, and poly-D-(−)-3-hydroxybutyric acid.

The formulations to be used for in vivo administration must be sterile. This is readily accomplished by, for example, filtration through sterile filtration membranes. Therapeutic ADC compositions are generally placed into a container having a sterile access port, for example, an intravenous solution bag or vial having a stopper pierceable by a hypodermic injection needle.

Suitable surface-active agents include, in particular, non-ionic agents, such as polyoxyethylenesorbitans (e.g., TWEEN™ 20, 40, 60, 80 or 85) and other sorbitans (e. g. Span™ 20, 40, 60, 80 or 85). Compositions with a surface-active agent will conveniently include between 0.05 and 5% surface-active agent, and can be between 0.1 and 2.5%. It will be appreciated that other ingredients may be added, for example mannitol or other pharmaceutically acceptable vehicles, if necessary.

Suitable emulsions may be prepared using commercially available fat emulsions, such as INTRALIPID™, LIPOSYN™, INFONUTROL™, LIPOFUNDIN™ and LIPIPHYSAN™. The active ingredient may be either dissolved in a pre-mixed emulsion composition or alternatively it may be dissolved in an oil (e.g., soybean oil, safflower oil, cottonseed oil, sesame oil, corn oil or almond oil) and an emulsion formed upon mixing with a phospholipid (e. g. egg phospholipids, soybean phospholipids or soybean lecithin) and water. It will be appreciated that other ingredients may be added, for example glycerol or glucose, to adjust the tonicity of the emulsion. Suitable emulsions will typically contain up to 20% oil, for example, between 5 and 20%. The fat emulsion can include fat droplets between 0.1 and 1.0 μm, particularly 0.1 and 0.5 μm, and have a pH in the range of 5.5 to 8.0. The emulsion compositions can be those prepared by mixing an ADC with INTRALIPID™ or the components thereof (soybean oil, egg phospholipids, glycerol and water).

The invention also provides kits for use in the instant methods. Kits of the invention include one or more containers including one or more ADCs of the invention and instructions for use in accordance with any of the methods of the invention described herein. Generally, these instructions include a description of administration of the ADC for therapeutic treatments.

The instructions relating to the use of the ADCs of the invention generally include information as to dosage, dosing schedule, and route of administration for the intended treatment. The containers may be unit doses, bulk packages (e.g., multi-dose packages) or sub-unit doses. Instructions supplied in the kits of the invention are typically written instructions on a label or package insert (e.g., a paper sheet included in the kit), but machine-readable instructions (e.g., instructions carried on a magnetic or optical storage disk) are also acceptable.

The kits of this invention are in suitable packaging. Suitable packaging includes, but is not limited to, vials, bottles, jars, flexible packaging (e.g., sealed Mylar or plastic bags), and the like. Also contemplated are packages for use in combination with a specific device, such as an infusion device such as a minipump. A kit may have a sterile access port (for example the container may be an intravenous solution bag or a vial having a stopper pierceable by a hypodermic injection needle). The container may also have a sterile access port (for example the container may be an intravenous solution bag or a vial having a stopper pierceable by a hypodermic injection needle). At least one active agent in the composition is an ADC of the invention. The container may further include a second pharmaceutically active agent.

Kits may optionally provide additional components such as buffers and interpretive information. Normally, the kit includes a container and a label or package insert(s) on or associated with the container.

The ADCs of the invention can be used for therapeutic, diagnostic, or non-therapeutic purposes. For example, the antibody or antigen-binding fragment thereof may be used as an affinity purification agents (e.g., for in vitro purification), as a diagnostic agent (e.g., for detecting expression of an antigen of interest in specific cells, tissues, or serum)

For therapeutic applications, the ADCs of the invention can be administered to a mammal, especially a human by conventional techniques, such as intravenously (as a bolus or by continuous infusion over a period of time), intramuscularly, intraperitoneally, intra-cerebrospinally, subcutaneously, intra-articularly, intrasynovially, intrathecally, orally, topically, or by inhalation. The antibodies or antigen-binding fragments also are suitably administered by intra-tumoral, peri-tumoral, intra-lesional, or peri-lesional routes. The ADCs of the invention can be used in prophylactic treatment or therapeutic treatment. For example, the ADCs of the invention may be used for the prophylactic or therapeutic treatment of cancers, autoimmune diseases, inflammatory diseases or infectious diseases.

3. Definitions

Unless otherwise defined herein, scientific and technical terms used in connection with the present invention shall have the meanings that are commonly understood by those of ordinary skill in the art. Further, unless otherwise required by context, singular terms shall include pluralities and plural terms shall include the singular. Generally, nomenclatures used in connection with, and techniques of, cell and tissue culture, molecular biology, immunology, microbiology, genetics and protein and nucleic acid chemistry and hybridization described herein are those well-known and commonly used in the art.

The term "L-D" refers to a linker-drug moiety resulting from a drug (D) linked to a linker (L). The term "Drug (D)" refers to any therapeutic agent useful in treating a disease. The drug has biological or detectable activity, for example, a cytotoxic agent, a chemotherapeutic agent, a cytostatic agent, or an immunomodulatory agent. In the context of cancer treatment, a therapeutic agent has a cytotoxic effect on tumors including the depletion, elimination and/or the killing of tumor cells. The terms drug, payload, and drug payload are used interchangeably. In certain embodiments, therapeutic agents have a cytotoxic effect on tumors including the depletion, elimination and/or the killing of tumor cells. In certain embodiments, the drug is DNA alkylating agent. In certain embodiments, the drug is a CPI or CBI dimer. In certain embodiments, the drug is (8S)-8-(chloromethyl)-6-[(3-{[(1S)-1-(chloromethyl)-5-hydroxy-8-methyl-1,6-dihydropyrrolo[3,2-e]indol-3(2H)-yl]carbonyl}bicyclo[1.1.1]pent-1-yl)carbonyl]-1-methyl-3,6,7,8-tetrahydropyrrolo[3,2-e]indol-4-yl dihydrogen phosphate. In certain embodiments, the drug is preferably membrane permeable.

The term "Linker (L)" describes the direct or indirect linkage of the antibody to the drug payload. Attachment of a linker to an antibody can be accomplished in a variety of ways, such as through surface lysines, reductive-coupling to oxidized carbohydrates, cysteine residues liberated by reducing interchain disulfide linkages, reactive cysteine residues engineered at specific sites, and acyl donor glutamine-containing tag or an endogenous glutamine made reactive by polypeptide engineering in the presence of transglutaminase and an amine. The present invention uses site specific methods to link the antibody to the drug payload. In one embodiment, conjugation occurs through cysteine residues that have been engineered into the antibody constant region. Linkers can be cleavable (i.e., susceptible to cleavage under intracellular conditions) or non-cleavable. In some embodiments, the linker is a cleavable linker.

An "antigen-binding fragment" of an antibody refers to a fragment of a full-length antibody that retains the ability to specifically bind to an antigen (preferably with substantially the same binding affinity). Examples of an antigen-binding fragment includes: an Fab fragment; an F(ab')2 fragment; an Fd fragment; an Fv fragment; a dAb fragment (Ward et al., (1989) Nature 341:544-546); an isolated complementarity determining region (CDR); a disulfide-linked Fv (dsFv); an anti-idiotypic (anti-Id) antibodies; an intrabody; a single chain Fv (scFv, see e. g., Bird et al. Science 242:423-426 (1988) and Huston et al. Proc. Natl. Acad. Sci. USA 85:5879-5883 (1988)); and a diabody (see e. g., Holliger et al. Proc. Natl. Acad. Sci. USA 90:6444-6448 (1993); Poljak et al., 1994, Structure 2:1121-1123). The antigen-binding fragment of the invention comprises the engineered antibody constant domain described herein, but does not need to comprise the full length Fc-region of a native antibody. For example, the antigen-binding fragment of the invention can be a "minibody" (VL-VH-CH3 or (scFv-CH3)$_2$; see, Hu et al., Cancer Res. 1996; 56(13):3055-61, and Olafsen et al., Protein Eng Des Sel. 2004; 17(4):315-23).

Residues in a variable domain of an antibody are numbered according Kabat, which is a numbering system used for heavy chain variable domains or light chain variable domains of the compilation of antibodies. See, Kabat et al., Sequences of Proteins of Immunological Interest, 5th Ed. Public Health Service, National Institutes of Health, Bethesda, Md. (1991)). Using this numbering system, the actual linear amino acid sequence may contain fewer or additional amino acids corresponding to a shortening of, or insertion into, a FR or CDR of the variable domain. For example, a heavy chain variable domain may include a single amino acid insert (residue 52a according to Kabat) after residue 52 of H2 and inserted residues (e. g. residues 82a, 82b, and 82c, according to Kabat) after heavy chain FR residue 82. The Kabat numbering of residues may be determined for a given antibody by alignment at regions of homology of the sequence of the antibody with a "standard" Kabat numbered sequence. Various algorithms for assigning Kabat numbering are available. The algorithm implemented in the 2012 release of Abysis (www.abysis.org) is used herein to assign Kabat numbering to variable regions unless otherwise noted.

Unless otherwise specified, amino acid residues in the IgG heavy constant domain of an antibody are numbered according the Eu index of Edelman et al., 1969, Proc. Natl. Acad. Sci. USA 63(1):78-85 as described in Kabat et al., 1991, referred to herein as the "EU index of Kabat". Typically, the Fc domain comprises from about amino acid residue 236 to about 447 of the human IgG1 constant domain. Correspondence between C numberings can be found, e.g., at IGMT database. Amino acid residues of the light chain constant domain are numbered according to Kabat et al., 1991. Numbering of antibody constant domain amino acid residues is also shown in International Patent Publication No. WO 2013/093809.

Unless otherwise specified, amino acid residues in the light chain constant domain of an antibody are numbered according to Kabat et al., 1991.

An amino acid residue of a query sequence "corresponds to" a designated position of a reference sequence (e. g., position 104 of SEQ ID NO:25 or position 162 of SEQ ID NO:26) when, by aligning the query amino acid sequence with the reference sequence, the position of the residue matches the designated position. Such alignments can be done by hand or by using well-known sequence alignment programs such as ClustalW2, or "BLAST 2 Sequences" using default parameters.

The term "about", as used here, refers to +/−10% of a value.

As used herein, the terms "engineered" (as in engineered cysteine) and "substituted" (as in substituted cysteine) are used interchangeably, and refer to mutating an amino acid to cysteine, in order to create a conjugation site for attaching another moiety to a polypeptide or antibody.

EXAMPLES

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

Example 1: Production of Stably Transfected Cells K334C Derived Antibody Variants 1A. Production of CD33-K334C CHO cells were transfected with DNA encoding CD33-K334C antibody variant and stable high production pools were isolated using standard procedures well-known in the art. The variant was purified to >95% homogeneity by capturing it from the conditioned medium on a MabSelect SuRe protein A column followed by additional purification using ion exchange column as follows. 20 liters of stable CHO clarified conditioned media was spiked with 5% (v/v) 0.55 M HEPES, 110 mM EDTA, pH 6.75 and was loaded onto a 0.94 L MabSelect SuRe (GE Healthcare Life Sciences Cat#17-5438-03 Lot#10204103) Protein A affinity column (GE BPG, 10 cm ID×12 cm H) equilibrated with TBS (50 mM Tris, 150 mM NaCl, pH 7.5). The column was washed with 2 column volumes (CV) of TBS pH 7.5 followed by 5 CVs of 50 mM Tris, 0.5 M CaCl2 pH 7.5 and 3 CVs of 10 mM Tris, 10 mM NaCl pH 7.5. The bound antibody was then step eluted with 100% 150 mM Glycine, pH 3.5. MabSelect SuRe peak pool was adjusted to pH 3.5 using 2 M Glycine, pH 2.7. The low pH pool was then immediately neutralized to pH 7.0 with 2 M Tris base and stored at 4° C. The neutralized protein A pool was titrated to pH 8.1 and was loaded onto an IEX column (HiScale: 2.6 cm I.D×19 cm H) packed with 100 ml of Fractogel EMD TMAE HiCap M resin (cat#1.10316.5003 lot#K93326916-316). The TMAE column was equilibrated with 50 mM Tris at pH 8.1. MabSelect SuRe peak pool was injected then washed with 3CV of 50 mM Tris pH8.1. The flow-through and wash containing the pure protein of interest was collected. The TMAE Pool was then concentrated and dialyzed against 20 mM NaSuccinate 8.5% Sucrose pH 5.8 buffer by a TFF unit (Millipore Pellicon 3, fully regenerated cellulose membrane, cat#P3C010C01, 30 kDa; 2×0.11m2; 1 cycle). Final pool was analyzed by OD280 (SoloVPE), SDS-PAGE, isoelectric focusing (IEF) (pH3-10) and analytical SEC (YMC-Pack Diol-200). Endotoxin was tested using Endosafe PTS RMPTS964 and Endosafe strip PTS-20 from Charles River Laboratories.

All the other CD33-cys variants as outlined in Table 7 were generated using similar procedures.

1B. Production of her 2-K334C Variant

CHO cells were transfected with DNA encoding Her2-K334C antibody variant and stable high production pools were isolated using standard procedures well-known in the art. The variant was purified to >95% homogeneity by capturing it from the conditioned medium on a MabSelect SuRe protein A column followed by additional purification using pre-packed G25 size exclusion column as follows. 3*50 mL of stable SSI CHO pool (from production study of the clone) clarified conditioned media (no spike of 5% (v/v) 0.55 M HEPES, 110 mM EDTA, pH 6.75) was loaded directly onto a 2 mL Mabselect SurRe (GE Healthcare Life Sciences Cat#17-5438-03 Lot#10204103) affinity column equilibrated with TBS (50 mM Tris, 150 mM NaCl, pH 7.5). The column was washed with 2 column volumes (CV) of TBS pH 7.5 followed by 5 CVs of 50 mM Tris, 0.5 M CaCl2 pH 7.5 and 3 CVs of 10 mM Tris, 10 mM NaCl pH 7.5. The bound antibody was then step eluted with 100% 150 mM Glycine, pH 3.5. Mabseclect Sure peak pool was adjusted to pH 3.5 using 2 M Glycine, pH 2.7 and then titrated to pH 8.1 with 2 M Tris base (27 µL used). The titrated pool was filtered and then loaded (200 mg/ml challenge) onto an IEX column (.D*H 0.5 cm*10 cm) packed with 0.7 ml of Fractogel EMD TMAE HiCap M resin (cat#1.10316.5003 lot#K93326916-316). The TMAE column was equilibrated with 50 mM Tris pH 8.1. Mabselect peak pool was injected then washed with 6CV of 50 mM Tris pH 8.1. The flow-through fractions containing the pure protein of interest were collected, and pooled. The TMAE Pool was then buffer exchanged to PBS via a pre-packed G25 (30 mL/CV). The final pool was 0.2 um filtered and analyzed by OD280 (NanoDrop), SDS-PAGE, IEF (pH3-10), and analytical SEC (YMC-Pack Diol-200).

1C. Production of 1.1-K334C Variant

CHO cells were transfected with DNA encoding 1.1-K334C antibody variant and stable high production pools were isolated using standard procedures well-known in the art. A two-column process, i.e., Protein-A capture followed by size-exclusion chromatography, was used to isolate this variant from the concentrated CHO pool starting material. Using these purification process, 1.1-K334C variant has >97% peak-of-interest (POI) as determined by analytical size-exclusion chromatography.

Example 2: Integrity of CD33 Derived Antibodies

Molecular assessment of the K334C cysteine variants (CD33-K334C and CD33-K334C/K392C) was performed to evaluate key biophysical properties to ensure that the variant would be amenable to a standard antibody manufacturing platform process.

To determine integrity of the purified engineered cysteine antibody variant preparations produced via stable CHO expression (and formulated in 20 mM sodium phosphate, 400 mM sodium chloride, pH 7.2), the percent purity of peaks was calculated using non-reduced capillary gel electrophoresis (Caliper LabChip GXII: Perkin Elmer Waltham, Mass.). Results as tabulated in Table 5 show that the engineered cysteine antibody variants contain low levels of fragments or half molecules. The double mutant K334C/K392C contained slightly more fragments relative to the single mutant (3.4% versus 1.2%). The main peak represents >95% intact antibody for both variants.

TABLE 5

Percent Purity of Peaks Calculated from Non-Reduced Electropherogram

| Antibody | Main Peak (%) | Fragments (%) |
|---|---|---|
| CD33-K334C | 98.8 | 1.2 |
| CD33-(K334C/K392C) | 96.6 | 3.4 |

Example 3: Generation of CD33-K334C-CPI ADC

3A. Preparation of Antibody for Conjugation

To 2060 µL CD33-K334C antibody (9.72 mg/mL solution in Dulbecco's Phosphate Buffered Saline (DPBS), 20 mg) was added 323.3 µL DPBS (Lonza, pH 7.4), 90 µL Ethylenediaminetetraacetic acid (EDTA, 0.5M solution in water) and 26.7 µL tris(2-carboxyethyl)phosphine hydrochloride (TCEP, 0.5M solution in water, 100 eq.). Reagents were mixed thoroughly and the mixture aged at ambient temperature overnight. The reaction mixture was then buffer exchanged via GE Sephadex gel desalting column and DPBS/5 mM EDTA eluent. The resulting reduced antibody solution (in 3.5 mL total volume) was treated with 131 µL dehydroascorbic acid (DHA, 50 mM solution in 50% ethanol in DPBS (v/v), 49 eq.). Reagents were thoroughly mixed and the mixture aged overnight at 4° C. The reaction mixture was then buffer exchanged via GE Sephadex gel desalting column and DPBS/5 mM EDTA eluent. The resulting antibody solution was concentrated to 1.7 mL total volume via Millipore Amicon Ultra 50 KD ultrafiltration device, and antibody concentration measured via NanoDrop 2000 spectrophotometer to be 11.18 mg/mL in DPBS/5 mM EDTA (19 mg, 95%).

3B. Conjugation of Linker-Payload to Prepared Antibody

The CPI drug compound was made according to methods disclosed in PCT Publication WO 2015/110935.

To 1340 µL prepared CD33-K334C antibody (11.18 mg/mL DPBS/5 mM EDTA, 15 mg) was added 77 µL DPBS/5 mM EDTA, 150 µL N,N-dimethylacetamide (DMA) and 100 µL of a solution of linker-payload, N-[1-(2,5-dioxo-2,5-dihydro-1H-pyrrol-1-yl)-21-oxo-3,6,9,12,15,18-hexaoxahenicosan-21-yl]-L-valyl-N$^5$-carbamoyl-N-[4-({[(2-{[({(8S)-8-(chloromethyl)-6-[(3-{[(1S)-1-(chloromethyl)-8-methyl-5-(phosphonooxy)-1,6-dihydropyrrolo[3,2-e]indol-3(2H)-yl]carbonyl}bicyclo[1.1.1]pent-1-yl)carbonyl]-1-methyl-3,6,7,8-tetrahydropyrrolo[3,2-e]indol-4-yl}oxy)carbonyl](methyl)amino}ethyl)(methyl)carbamoyl]oxy}methyl)phenyl]-L-ornithinamide (MalPeg6-vc-PABC-DMAE-CPI; LP7; Table 4) (10 mM solution in DMA, 10 eq.). Reagents were thoroughly mixed and the mixture aged at ambient temperature for 2 hours. Next, the crude reaction was buffer exchanged via GE Sephadex gel desalting column to DPBS pH 7.4 and purified by size exclusion chromatography via GE Akta Explorer system using GE SEC HiLoad 26/60 Superdex 200 PG column with DPBS pH 7.4 as eluent to afford monomeric ADC. The resulting ADC, CD33-K334C-CPI, was characterized using the analytical methods described below.

Identical methods were employed in the preparation of other CD33-Cys variant ADCs (Tables 6 and 7), Her2-K334C variant ADC and 1.1-K334C ADC, respectively.

Example 4: Analytical Characterization of K334C ADCs

4A. Protein LC/MS Analysis.

Samples were prepped for LCMS analysis by combining approximately 1-5 µl of sample (approximately 1-5 mg/ml ADC in pH 7.4 PBS buffer) to 10 µl total volume with additional pH 7.4 PBS buffer. Approximately 5 µl of 0.5M solution of tris(2-carboxyethyl)phosphine (TCEP) in water was added, and the mixture was incubated at 37° C. for 5-10 minutes prior to analysis. The samples were injected into an Agilent 110 HPLC system fitted with an Agilent Poroshell 300SB-C8 (2. 1×75 mm) column. The system temperature was set to 60° C. A 5 minute gradient from 20% to 45% acetonitrile in water (with 0.1% formic acid modifier) was utilized. The eluent was monitored by UV (220 nM) and by a Waters Micromass ZQ mass spectrometer (ESI ionization; cone voltage: 20V; Source temp: 120° C.; Desolvation temp: 350° C.). The crude spectrum containing the multiple-charged species was deconvoluted using MaxEnt1 within MassLynx 4. 1 software package according to the manufacturer's instructions.

4B. MS Determination of Loading Per Antibody

The total loading of the payload to the antibody to make an ADC is referred to as the Drug Antibody Ratio or DAR. The DAR was calculated for each of the ADCs made and reported in Tables 6 and 7.

The spectra for the entire elution window (usually 5 minutes) were combined into a single summed spectrum (i.e., a mass spectrum that represents the MS of the entire sample). MS results for ADC samples were compared directly to the corresponding MS of the identical non-loaded control antibody. This allowed for the identification of loaded/nonloaded heavy chain (HC) peaks and loaded/non-loaded light chain (LC) peaks. The ratio of the various peaks can be used to establish loading based on the equation below (Equation 1). Calculations are based on the assumption that loaded and non-loaded chains ionize equally which has been determined to be a generally valid assumption. The following calculation was performed in order to establish the DAR:

$$\text{Loading} = 2*[LC1/(LC1+LC0)] + 2*[HC1/(HC0+HC1+HC2)] + 4*[HC2/(HC0+HC1+HC2)] \quad \text{Equation 1:}$$

Where the indicated variables are the relative abundance of: LC0=unloaded light chain, LC1=single loaded light chain, HC0=unloaded heavy chain, HC1=single loaded heavy chain, and HC2=double loaded heavy chain. One of ordinary skill in the art would appreciate that the invention encompasses expansion of this calculation to encompass higher loaded species such as LC2, LC3, HC3, HC4, HC5, and the like.

4C. Analytical Size Exclusion Chromatography

Column: GE Superdex 200 (5/150 GL); Mobile phase: Phosphate buffered saline (PBS, 1×, pH 7.4) with 2% acetonitrile; Isocratic; Flow rate: 0.25 mL/minute. Temperature: room temperature; Injection Volume: 10 µL of 1 mg/mL stock; Instrument: Agilent 1100 HPLC. The resulting conjugates were >95% pure by SEC.

4D. Hydrophobic Interaction Chromatography (HIC)

Compounds were prepared for HIC analysis by diluting samples to approximately 1 mg/ml with PBS. The samples were analyzed by auto-injection of 15 µl onto an Agilent 1200 HPLC with a TSK-GEL Butyl NPR column (4.6×3.5 mm, 2.5 µm pore size; Tosoh Biosciences part #14947). The system includes an auto-sampler with a thermostat, a column heater and a UV detector.

The gradient method was used as follows: Mobile phase A: 1.5M ammonium sulfate, 50 mM potassium phosphate dibasic (pH 7); Mobile phase B: 20% isopropyl alcohol, 50 mM potassium phosphate dibasic (pH 7); T=0 min. 100% A; T=12 min., 0% A.

Relative retention times (RRT) are calculated by comparing the retention times of ADC to its naked antibody counterpart. Relative retention times are shown in Table 7. As shown, these vary widely between different conjugates indicating that the position where payload is conjugated can dictate the hydrophobicity of the resulting conjugate.

TABLE 6

Analytical Data for Exemplified ADCs

| ADC ID | Linker-Payload ID | Theoretical Δ mass or linker-payload molecular weight | Mass Spectra: SEC-HPLC retention time and HPLC Δ mass for the Heavy Chain (HC) portion | Loading or Drug per Antibody Ratio (DAR) |
|---|---|---|---|---|
| CD33-K334C-CPI | LP7 | 1608 | SEC (Protocol B): 6.514 minutes; HPLC (Protocol A): HC Δ mass = 1608 | 1.9 |
| CD33-K392C-CPI | LP7 | 1608 | SEC (Protocol B): 6.499 minutes; HPLC (Protocol A): HC Δ mass = 1607 | 2.0 |
| CD33-K334C/K392C-CPI | LP7 | 3216 (1608 × 2) | SEC (Protocol B): 6.427 minutes; HPLC (Protocol A): HC Δ mass = 3216 | 4.0 |
| Her2-K334C-CPI | LP7 | 1608 | SEC (Protocol B): 6.601 minutes; HPLC (Protocol A): HC Δ mass = 1610 | 2.0 |
| 1.1-K334C-CPI | LP7 | 1608 | SEC (Protocol B): 6.569 minutes; HPLC (Protocol A): HC Δ mass = 1608 | 2.0 |

Example 5. Generation of CD33-(K334C/K392C)-MalPeg6-Vc-PABC-DMAE-CPI ADC

5A. Preparation of Antibody for Conjugation

To 4500 µL CD33-(K334C/K392C) antibody (10.94 mg/mL solution in Dulbecco's Phosphate Buffered Saline (DPBS), 49 mg) was added 253 µL DPBS (Lonza, pH 7.4), 180 µL Ethylenediaminetetraacetic acid (EDTA, 0.5M solution in water) and 66.7 µL tris(2-carboxyethyl)phosphine hydrochloride (TCEP, 0.5M solution in water, 100 eq.). Reagents were mixed thoroughly and the mixture aged at ambient temperature overnight. The reaction mixture was then buffer exchanged via GE Sephadex gel desalting columns and DPBS/5 mM EDTA eluent. The resulting reduced antibody solution (in 7.0 mL total volume) was treated with 166 µL DPBS/5 mM EDTA solution and 334 µL dehydroascorbic acid (DHA, 50 mM solution in 50% ethanol in DPBS (v/v), 50 eq.). Reagents were thoroughly mixed and the mixture aged overnight at 4° C. The reaction mixture was then buffer exchanged via GE Sephadex gel desalting columns and DPBS/5 mM EDTA eluent. The resulting antibody solution was concentrated to 4.6 mL total volume via Millipore Amicon Ultra 50 KD ultrafiltration device, and antibody concentration measured via NanoDrop 2000 spectrophotometer to be 8.29 mg/mL in DPBS/5 mM EDTA (38 mg, 78%).

5B. Conjugation of Linker-Payload to Prepared Antibody:

The CPI drug compound was made according to methods disclosed in PCT Publication WO 2015/110935.

To 1810 µL prepared CD33-(K334C/K392C)-human IgG1 antibody (8.29 mg/mL DPBS/5 mM EDTA, 15 mg) was added 220 µL N,N-dimethylacetamide (DMA) and 100 µL of a solution of linker-payload, N-[1-(2,5-dioxo-2,5-dihydro-1H-pyrrol-1-yl)-21-oxo-3,6,9,12,15,18-hexaoxa-henicosan-21-yl]-L-valyl-$N^5$-carbamoyl-N-[4-({[(2-{[({(8S)-8-(chloromethyl)-6-[(3-{[(1S)-1-(chloromethyl)-8-methyl-5-(phosphonooxy)-1,6-dihydropyrrolo[3,2-e]indol-3(2H)-yl]carbonyl}bicyclo[1.1.1]pent-1-yl)carbonyl]-1-methyl-3,6,7,8-tetrahydropyrrolo[3,2-e]indol-4-yl}oxy)carbonyl](methyl)amino}ethyl)(methyl)carbamoyl]oxy}methyl)phenyl]-L-ornithinamide (MalPeg6-vc-PABC-DMAE-CPI) (10 mM solution in DMA, 10 eq.). Reagents were thoroughly mixed and the mixture aged at ambient temperature for 2 hours. Next, the crude reaction was buffer exchanged via GE Sephadex gel desalting column to DPBS pH 7.4 and purified by size exclusion chromatography via GE Akta Explorer system using GE SEC HiLoad 26/60 Superdex 200 PG column with DPBS pH 7.4 as eluent to afford monomeric ADC. The resulting ADC was characterized using the analytical methods described in Example 4 and DAR values can be found in Tables 6 and 7.

Example 6. Plasma Stability of CD33 ADCs

From stock ADC solutions, 50 µg/mL of each ADC was prepared in fresh pooled male CD-1 mouse plasma with sodium heparin. In a frozen 96-well plate, 0-min time-point was sampled immediately after the ADC plasma preparation. The plate was then placed in a −80° C. freezer. The remaining ADC plasma samples in capped tubes were incubated at 37° C. in a $CO_2$ controlled incubator. Aliquots were removed after 8, 24 and 72-hours and frozen at −80° C. until analysis. At the time of analysis, the plasma samples were thawed and deglycosylated for 2 hr at 37° C. using 2 µl of IgZero (Genovis, Switzerland). The incubation time is reported as the total time period for which ADCs were in contact with plasma. The deglycosylated samples were analyzed utilizing an immunocapture high resolution LC/MS method. Briefly, 50 µl of plasma sample was added to a 96 well lo-bind plate (Eppendorf, Hamburg, Germany) and deglycosylated for 1.5 hr at 37° C. using 2 µl of IgZero (Genovis, Switzerland) prepared in water. Capture of ADC was performed using biotinylated goat anti-human FC gamma (Jackson ImmunoResearch, West Grove, Pa.) at a ratio of 3:1 capture:ADC for 1 hr at room temperature, under gentle shaking. Streptavidin T1 beads (Life Technologies, Grand Island, N.Y.) were washed and added to the samples, mixing for 0.5 hr, then a magnet was used to wash, and finally elute with 50 µl of 2% formic acid. The samples were analyzed in a reduced format and were treated with the addition of 200 mM tris(2-carboxyethyl)phosphine (TCEP) for a final TCEP concentration of 20 mM. The samples (2 µl) were injected onto a BEH C4 column (150 µm×50 mm, 1.7 µm, 300A, Waters) set at 85° C., with an autosampler set at 4° C. LC separation was achieved using a nano-acquity LC system (Waters Technology). Spectra were collected from 2-8 min using a Waters Synapt-G2S QToF equipped with an ionKey nanospray source (Waters Technology). Positive TOF-MS scan was collected over m/z range of 800-2100 amu using MassLynx (Waters Technology) software, and was deconvoluted using the MaxEnt1 algorithm in BioPharmaLynx software (Waters Technology).

As shown in FIG. 1, all the CD33 ADCs showed different degrees of plasma stability (represented by loss of DAR). This demonstrates that the site of conjugation dictates the relative plasma stability of the payload. The plasma stability of ADCs were also classified as low, high and medium as shown in Table 7. The drug-to-antibody ratio (DAR) in plasma at 37° C. at 72 hours for CD33-K334C is 1.7, while DAR for CD33-K392C is 1.9. Conversely, DAR in plasma at 37° C. at 72 hours for all other conjugates tested was less than 1.0 (FIG. 1).

TABLE 7

Plasma Stability of CD33 ADCs

| Variant | RRT | Plasma stability | DAR |
|---|---|---|---|
| Light Chain | | | |
| K183C | 1.25 | poor | 1.9 |
| Heavy Chain | | | |
| K290C | 1.52 | Moderate | 1.9 |
| K334C | 1.11 | good | 1.9 |
| Q347C | 1.70 | Moderate | 1.9 |
| Y373C | 1.36 | poor | 1.7 |
| E388C | 1.73 | poor | 1.9 |
| K392C | 1.21 | good | 2 |
| K334C/K392C | 1.07 | N/A | 4 |

Example 7. Thermal Stability of ADCs

Differential Scanning Calorimetry (DCS) was used to determine the thermal stability of the engineered cysteine antibody CPI conjugates shown in Table 8. For this analysis, samples formulated in PBS-CMF pH 7.2 were dispensed into the sample tray of a MicroCal VP-Capillary DSC with Autosampler (GE Healthcare Bio-Sciences, Piscataway, N.J.), equilibrated for 5 minutes at 10° C. and then scanned up to 110° C. at a rate of 100° C. per hour. A filtering period of 16 seconds was selected. Raw data was baseline corrected and the protein concentration was normalized. Origin Software 7.0 (OriginLab Corporation, Northampton, Mass.) was used to fit the data to an MN2-State Model with an appropriate number of transitions.

As shown in Table 8, both single K334C and double mutant K334C/K392C ADCs exhibited excellent thermal stability as determined by the first melting transition (Tm1) >65° C. These results demonstrated that both antibody variants are not perturbed during conjugation.

TABLE 8

Thermal Stability of CD33 ADCs

| CD33 ADC | $T_m1$ | $T_m2$ | $T_m3$ |
|---|---|---|---|
| K334C | 68.19 ± 0.06 | 74.11 ± 0.21 | 83.94 ± 0.14 |
| K334C/K392C | 68.28 ± 0.06 | 74.14 ± 0.20 | 83.75 ± 0.14 |

Example 8: ADC Binding to Human FcRn

It is believed in the art that FcRn interacts with IgG regardless of subtype in a pH dependent manner and protects the antibody from degradation by preventing it from entering the lysosomal compartment where it is degraded. Therefore, a consideration for selecting positions for introduction of reactive cysteines into the wild type IgG1-Fc region was to avoid altering the FcRn binding properties and half-life of the antibody comprising the engineered cysteine.

BIAcore® analysis was performed to determine the steady-state affinity (KD) for the anti-CD33 derived monoclonal antibodies and their respective ADCs for binding to human FcRn. BIAcore® technology utilizes changes in the refractive index at the surface layer of a sensor upon binding of the anti-CD33 derived monoclonal antibodies or their respective ADCs to human FcRn protein immobilized on the layer. Binding was detected by surface plasmon resonance (SPR) of laser light refracting from the surface. Human FcRn was specifically biotinylated through an engineered Avi-tag using the BirA reagent (Catalog #: BIRA500, Avidity, LLC, Aurora, Colo.) and immobilized onto a streptavidin (SA) sensor chip to enable uniform orientation of the FcRn protein on the sensor. Next, various concentrations of the anti-CD33 derived monoclonal antibodies or their respective ADCs or in 20 mM MES (2-(N-morpholino)ethanesulfonic acid pH 6.0, with 150 mM NaCl, 3 mM EDTA (ethylenediaminetetraacetic acid), 0.5% Surfactant P20 (MES-EP) were injected over the chip surface. The surface was regenerated using HBS-EP+0.05% Surfactant P20 (GE Healthcare, Piscataway, N.J.), pH 7.4, between injection cycles. The steady-state binding affinities were determined for the anti-CD33 derived monoclonal antibodies or their respective ADCs, and these were compared with the wild type anti-CD33 antibody (comprising no cysteine mutations in the IgG1 Fc region).

These data demonstrated that incorporation of engineered cysteine residues into the IgG-Fc region at positions 334 and/or 392 did not alter affinity to FcRn (Table 9).

TABLE 9

Steady-State Affinities of Site-Specific Conjugates Binding Human FcRn

| mAb/ADC | $K_D$ (nM) |
|---|---|
| Wild-type | 1274.0 |
| CD33-K334C | 1067.0 |
| CD33-K334C-CPI | 922.3 |
| CD33-K392C | 1177.0 |
| CD33-K392C-CPI | 993.6 |
| CD33-(K334C/K392C) | 964.1 |
| CD33-(K334C/K392C)-CPI | 1220.0 |

Example 9: ADC Binding to Fcγ Receptors

Binding of the ADCs using site-specific conjugation to human Fc-γ receptors was evaluated in order to understand if conjugation to a payload alters binding which can impact antibody related functionality such as antibody-dependent cell-mediated cytotoxicity (ADCC). FcγIIIa (CD16) is expressed on NK cells and macrophages, and co-engagement of this receptor with the target expressing cells via antibody binding induces ADCC. BIAcore® analysis was used to examine binding of the anti-CD33 derived monoclonal antibodies and their respective ADCs to Fc-γ receptors IIa (CD32a), IIb(CD32b), IIIa (CD16) and FcγRI (CD64).

For this surface plasmon resonance (SPR) assay, CD33 extra-cellular domain protein was immobilized on a CM5 chip (GE Healthcare, Piscataway, N.J.) and ~300-400 response units (RU) of either a CD33 monoclonal antibody or its respective ADC was captured. Various concentrations of the Fcγ receptors FcγIIa (CD32a), FcγIIb(CD32b), FcγIIIa (CD16a) and FcγRI (CD64) were injected over the surface and binding was determined.

FcγRs IIa, IIb and IIIa exhibited rapid on/off rates and therefore the sensorgrams were fit to steady state model to obtain $K_D$ values. FcγRI exhibited slower on/off rates so data was fit to a kinetic model to obtain $K_D$ values.

with CelltiterGlo (Promega, Madison, Wis.). Luminescence was determined using a Victor plate reader (Perkin Elmer, Waltham, Mass.). $IC_{50}$ values were calculated using a four-parameter logistic model with XLfit (IDBS, Bridgewater, N.J.) and reported ng/ml antibody concentration in Table 11. The $IC_{50}$ are shown +/−the standard deviation.

Table 11 shows IC50 (ng/mL) values of the anti-CD33 ADC treatments in several cell lines. These data demonstrate that CD33-K334C-CPI with drug-antibody ratio (DAR) of 2 induces cell death in CD33 expressing cell lines (HL60, NB4, Hel92.1.7, TF-1). The data further demonstrates that the double cysteine mutant CD33-K334C/K392C-CPI with a DAR of 4 is more potent than the DAR2 K334C version. All ADCs were minimally active in the CD33 negative cell line, Raji indicating that the activity seen in CD33 expressing cell lines is selective. Corroborating this observation, the non-targeted control 1.1-K334C-CPI ADC with DAR of 2 was substantially less active at the highest doses tested. In addition, it is worth noting that potent activity is also observed in CD33 expressing cell lines like HEL92.1.7 that express multi-drug resistant pumps (e.g., MDR) indicating that CPI evades multi-drug resistance pumps.

TABLE 11

In Vitro Cytotoxicity Data (ng/mL) for CD33 Conjugates and Negative Control

| ADC | DAR | IC50 Values (ng/ml) | | | | |
|---|---|---|---|---|---|---|
| | | HL60 | NB4 | HEL92.1.7 | TF-1 | Raji |
| CD33-K334C-CPI | 1.9 | 10.3 ± 11.4 | 1.9 ± 3.1 | 10.1 ± 16.6 | 52.2 ± 53.6 | 1440.9 ± 604.5 |
| CD33-K334C/K392C-CPI | 4 | 2.5 ± 2.1 | 0.4 ± 0.1 | 0.9 ± 0.3 | 158.6 ± 163.9 | 1045.4 ± 497.1 |
| 1.1-K334C- CPI | 2 | 232.3 ± 118.4 | 143.3 ± 33 | 414.7 ± 308.5 | 3198.6 ± 2218.4 | 1616 ± 1061.2 |

Conjugation of payload at the engineered cysteine position 334 showed a moderate loss in FcγR affinity compared to their unconjugated counterparts while conjugation at position 392 did not modulate the FcγR affinity (Table 10). This loss in binding is also reflected in the double K334C/K392C conjugate and presence of the four payloads in the double mutant exacerbated this loss. It is important to note that these mutations alone do not result in the loss of binding to FcγR prior to conjugation. Taken together, these results suggested that location of the conjugated payload can impact binding of the ADC to FcγR and may impact the effector functionality of the conjugate.

TABLE 10

Binding Affinity (μM) of Site-Specific Conjugates for Fcγ Receptors binding to CD16a, CD32a, CD32b and CD64

| | CD16a | CD32a | CD32b | CD64 |
|---|---|---|---|---|
| Wild-type | 0.40 | 1.11 | 3.90 | 0.00015 |
| CD33-K334C | 0.19 | 0.84 | 3.30 | 0.00002 |
| CD33-K334C-CPI | 1.75 | 3.90 | 6.30 | 0.00007 |
| CD33-K392C | 0.39 | 1.03 | 3.60 | 0.00010 |
| CD33-K392C-CPI | 0.19 | 2.08 | 4.37 | 0.00015 |
| CD33-(K334C/K392C) | 0.21 | 0.90 | 3.46 | 0.00002 |
| CD33-(K334C/K392C)-CPI | 5.65 | 12.90 | 20.10 | 0.00017 |

Example 10. Cytotoxicity of ADCs

10A. Cytotoxicity of CD33 K334C ADC

For in vitro cytotoxicity assay with AML cell lines, cells were incubated with different concentrations of ADCs/payload for 96 hours after which cell viability was measured 10B. Cytotoxicity of Her2 K334C ADC Her2-Target expressing N87 (gastric cancer), MDA-MB-453 (breast cancer)) or Her2-non-expressing (HT29) cells were seeded in 96-well cell culture plates for 24 hours before treatment. Cells were treated with 3-fold serially diluted antibody-drug conjugates in duplicate at 10 concentrations. Cell viability was determined by CellTiter 96® AQ$_{ueous}$ One Solution Cell Proliferation MTS Assay (Promega, Madison Wis.) 96 hours after treatment. Relative cell viability was determined as percentage of untreated control. IC50 values were calculated using a four parameter logistic model #203 with XLfit v4.2 (IDBS, Guildford, Surry, UK). As shown in Table 12, Her2-K334C-CPI conjugate showed selective killing of Her2-expressing cells.

TABLE 12

In vitro Cytotoxicity Data (EC50; ng/mL) for Herceptin Conjugate and Negative Control

| Identifier | N87 | MDA-MB-453 | HT29 |
|---|---|---|---|
| Her2-K334C- CPI | 21.34 | 45.45 | 13532 |
| 1.1-K334C-CPI | 3397 | ND | 11216 |

ND Not determined

Example 11. Assessment of Anti-CD33 ADC Activity in Human AML In Vivo Models

The anti-CD33 CPI ADCs were tested in Acute Myeloid Leukemia (AML) xenograft models. For each model described below the first dose was given on Day 0 and the tumors were measured at least once a week and their volume was calculated using the formula, tumor volume $(mm^3)=0.5\times(tumor\ width^2)(tumor\ length)$. The mean tumor volumes (±S.E.M.) for each treatment group were calculated having a maximum of 10 animals and a minimum of 6 animals to be included. All animal experiments were conducted in a facility accredited by the Association for Assessment of Laboratory Animal Care under Institutional Animal Care and Use Committee guidelines and appropriate animal research approval.

11A. HL60 AML Xenografts

Figure 2:
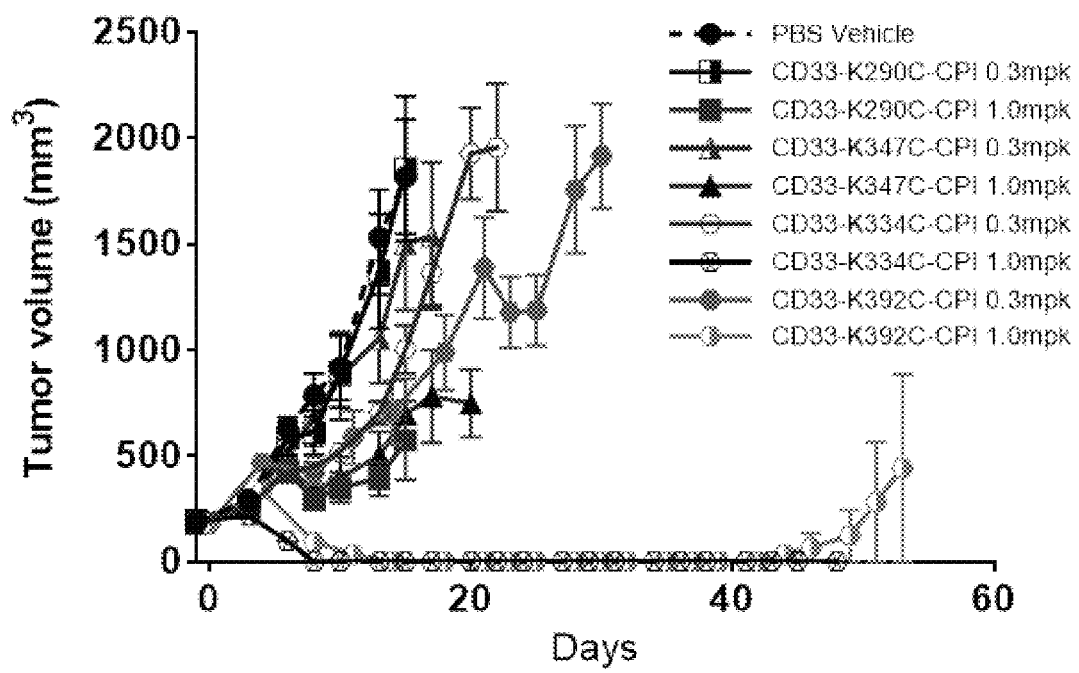
FIG. 2 shows the efficacy of CD33 ADC constructs conjugated at different sites in an HL60 xenograft model. ADC constructs conjugated at position 334 (CD33-K334C-CPI) administered at 1 mg/kg (mpk), and ADC constructs conjugated at position 392 (CD33-K392C-CPI) administered at 0.3 mg/kg (mpk) were the most efficacious.

To evaluate DAR 2 anti-CD33 CPI ADCs, the HL60 AML sc xenograft model was dosed intravenously four times every four days (q4dx4) with PBS vehicle, anti-CD33 ADC (CD33-K334C-CPI, CD33-K392C-CPI, CD33-K290C-CPI, CD33-K347C-CPI) at the doses provided in Table 13. FIG. 2 shows a graph of the data from Table 13 of the ADCs with site specific conjugated MalPeg6ValCitPABC-DMAE-CPI linker-payloads at 0.3 and 1 mg/kg (mpk) doses.

The data demonstrates that the anti-CD33 ADC CD33-K334C-CPI and CD33-K392C-CPI inhibited growth of HL60 AML subcutaneous xenograft tumors. The q4dx4 dose of 1mpk was the most efficacious dose of ADC tested in this study, and by day 48, ten out of ten animals in their dose group remained tumor-free. Further, the data also demonstrates that anti-CD33-K334C-CPI ADC inhibited tumor growth more potently than anti-CD33 ADCs conjugated at K392C, K290C and K347C. Thus, ADCs conjugated at position 334 or at position 392 surprisingly showed superior plasma stability and in vivo efficacy as compared to ADCs conjugated at other positions.

Figure 3:
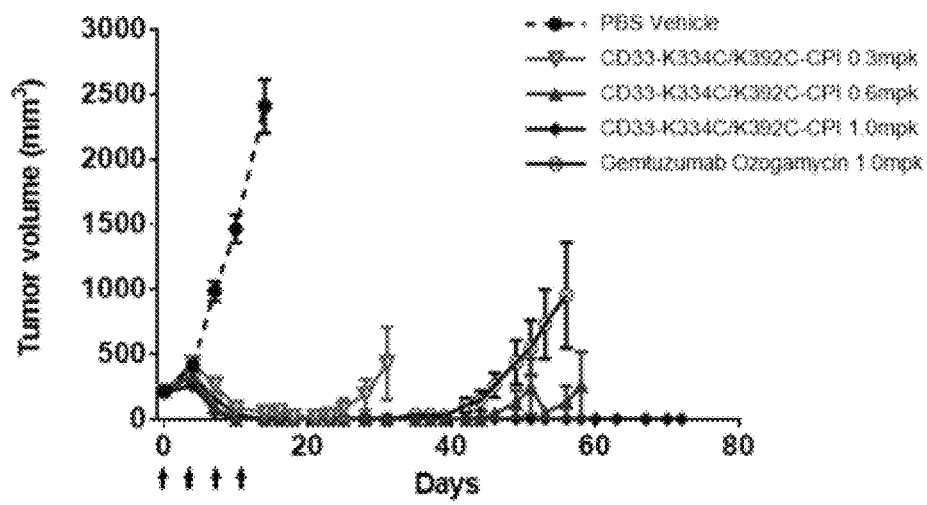
FIG. 3 represents the efficacy of different doses of CD33 ADC constructs conjugated at sites 334 and 392 (CD33-K334C/K392C-CPI) in an HL60 xenograft model. The data demonstrates that CD33-K334C/K392C-CPI administered at 0.6 mg/kg was the most efficacious dose in this model.

As both CD33-K334C-CPI and CD33-K392C-CPI showed best stability in plasma, the effects of the DAR 4 CD33-K334C/K392C ADC was also examined in immune deficient mice on the in vivo growth of human tumors. For subcutaneous (sc) AML models, $10\times10^6$ HL60 cells were implanted subcutaneously in the flank of female NOD-SCID mice. When the tumors reached an average volume of 200 $mm^3$, animals were staged to ensure uniformity of the tumor size among various treatment groups. The HL60 AML sc xenograft model was dosed intravenously four times every four days (Q4dx4) with PBS vehicle, anti-CD33 ADC and comparator control gemtuzumab ozagamicin (calicheamicin conjugate of an anti-CD33; DAR 4) at the doses provided in Table 14. FIG. 3 shows a graph of the data from Table 14 of the anti-CD33-CPI ADCs at 0.3, 0.6 and 1 mg/kg doses. The data demonstrates that the q4dx4 dose of CD33-K334C/K392C-CPI (FIG. 3) at 0.6 mg/kg was the most efficacious in this model owing to its higher drug-antibody ratio of 4. Further, the data shows that CD33-K334C/K392C-CPI ADCs inhibited tumor growth more potently than gemtuzumab ozogamicin (DAR 4).

TABLE 13

HL60 AML Xenografts - CD33 ADCs

| q4d x4 | \multicolumn{9}{c}{HL60 AML xenografts, mean tumor volume (mm3 +/− SEM)} | | | | | | | | |
|---|---|---|---|---|---|---|---|---|
| DOSE | PBS | CD33-K290C-CPI | | CD33-K347C-CPI | | CD33-K334C-CPI | | CD33-K392C-CPI | |
| (MPK) | 0 | 0.3 | 1 | 0.3 | 1 | 0.3 | 1 | 0.3 | 1 |
| Day 0 | | | | | | | | 179 ± 12 | 180 ± 8 |
| Day 1 | 186 ± 7 | 196 ± 15 | 192 ± 14 | 194 ± 8 | 180 ± 9 | 186 ± 12 | 191 ± 9 | | |
| Day 3 | 292 ± 18 | 276 ± 19 | 291 ± 19 | 261 ± 39 | 253 ± 14 | 269 ± 13 | 218 ± 11 | | |
| Day 4 | | | | | | | | 468 ± 43 | 339 ± 26 |
| Day 6 | 630 ± 52 | 582 ± 78 | 427 ± 52 | 527 ± 87 | 449 ± 38 | 423 ± 21 | 97 ± 23 | | |
| Day 8 | 786 ± 103 | 610 ± 105 | 293 ± 42 | 668 ± 123 | 331 ± 49 | 450 ± 20 | 0 ± 0 | 418 ± 52 | 95 ± 24 |
| Day 10 | 918 ± 153 | 896 ± 169 | 351 ± 71 | 878 ± 209 | 399 ± 98 | 518 ± 36 | 0 ± 0 | | |
| Day 11 | | | | | | | | 588 ± 127 | 32 ± 12 |
| Day 13 | 1531 ± 226 | 1373 ± 271 | 393 ± 82 | 1052 ± 211 | 500 ± 112 | 702 ± 55 | 0 ± 0 | | |
| Day 14 | | | | | | | | 704 ± 151 | 0 ± 0 |
| Day 15 | 1819 ± 270 | 1855 ± 343 | 572 ± 187 | 1503 ± 315 | 698 ± 167 | 1002 ± 114 | 0 ± 0 | | |
| Day 17 | 1913 ± 104 | 1408 ± 413 | 591 ± 185 | 1539 ± 347 | 781 ± 219 | 1363 ± 154 | 0 ± 0 | | |
| Day 18 | | | | | | | | 989 ± 177 | 0 ± 0 |
| Day 20 | 2199 ± 231 | 1600 ± 552 | 1172 ± 301 | 1323 ± 175 | 832 ± 145 | 1927 ± 216 | 0 ± 0 | | |
| Day 21 | | | | | | | | 1387 ± 242 | 0 ± 0 |
| Day 22 | — | — | — | — | 855 ± 107 | 1957 ± 302 | 0 ± 0 | | |
| Day 23 | | | | | | | | 1178 ± 168 | 0 ± 0 |
| Day 24 | — | — | — | — | 1189 ± 190 | — | 0 ± 0 | | |
| Day 25 | | | | | | | | 1187 ± 168 | 0 ± 0 |
| Day 27 | — | — | — | — | 1432 ± 174 | — | 0 ± 0 | | |
| Day 28 | | | | | | | | 1757 ± 301 | 0 ± 0 |
| Day 29 | — | — | — | — | 2260 ± 284 | — | 0 ± 0 | | |
| Day 30 | | | | | | | | 1916 ± 248 | 0 ± 0 |
| Day 31 | — | — | — | — | — | — | 0 ± 0 | | |
| Day 32 | | | | | | | | | 0 ± 0 |
| Day 34 | — | — | — | — | — | — | 0 ± 0 | | |
| Day 35 | | | | | | | | | 0 ± 0 |
| Day 36 | — | — | — | — | — | — | 0 ± 0 | | |
| Day 37 | | | | | | | | | 0 ± 0 |
| Day 38 | — | — | — | — | — | — | 0 ± 0 | | |
| Day 39 | | | | | | | | | 0 ± 0 |
| Day 41 | — | — | — | — | — | — | 0 ± 0 | | |
| Day 42 | | | | | | | | | 0 ± 0 |
| Day 43 | — | — | — | — | — | — | 0 ± 0 | | |
| Day 44 | | | | | | | | | 33 ± 33 |
| Day 45 | — | — | — | — | — | — | 0 ± 0 | | |
| Day 46 | | | | | | | | | 68 ± 68 |
| Day 48 | — | — | — | — | — | — | 0 ± 0 | | |
| Day 49 | | | | | | | | | 123 ± 123 |

TABLE 13-continued

HL60 AML Xenografts - CD33 ADCs q4d x4 — HL60 AML xenografts, mean tumor volume (mm3 +/− SEM)

| DOSE (MPK) | PBS 0 | CD33-K290C-CPI 0.3 | CD33-K290C-CPI 1 | CD33-K347C-CPI 0.3 | CD33-K347C-CPI 1 | CD33-K334C-CPI 0.3 | CD33-K334C-CPI 1 | CD33-K392C-CPI 0.3 | CD33-K392C-CPI 1 |
|---|---|---|---|---|---|---|---|---|---|
| Day 51 | | | | | | | | | 283 ± 283 |
| Day 53 | | | | | | | | | 443 ± 443 |

TABLE 14

HL60 AML Xenografts - CD33 double mutant (K334C/K392C) ADCs

HL60 AML xenografts, mean tumor volume (mm³ +/− SEM) q4dx4

| | PBS | CD33-K334C/K392C-CPI | CD33-K334C/K392C-CPI | CD33-K334C/K392C-CPI | Gemtuzumab Ozogamycin |
|---|---|---|---|---|---|
| DOSE (mpk) | 0 | 0.3 | 0.6 | 1 | 1 |
| Day 0 | 214 ± 11 | 215 ± 17 | 218 ± 14 | 219 ± 16 | 220 ± 19 |
| Day 4 | 406 ± 38 | 283 ± 38 | 301 ± 23 | 248 ± 12 | 337 ± 41 |
| Day 7 | 986 ± 77 | 278 ± 146 | 29 ± 14 | 31 ± 13 | 158 ± 31 |
| Day 10 | 1466 ± 108 | 268 ± 224 | 0 ± 0 | 0 ± 0 | 35 ± 16 |
| Day 14 | 2411 ± 206 | 19 ± 13 | 0 ± 0 | 0 ± 0 | 0 ± 0 |
| Day 16 | — | 13 ± 13 | 0 ± 0 | 0 ± 0 | 0 ± 0 |
| Day 18 | — | 8 ± 8 | 0 ± 0 | 0 ± 0 | 0 ± 0 |
| Day 21 | — | 15 ± 15 | 0 ± 0 | 0 ± 0 | 0 ± 0 |
| Day 23 | — | 37 ± 25 | 0 ± 0 | 0 ± 0 | 0 ± 0 |
| Day 25 | — | 82 ± 59 | 0 ± 0 | 0 ± 0 | 0 ± 0 |
| Day 28 | — | 138 ± 92 | 0 ± 0 | 0 ± 0 | 0 ± 0 |
| Day 31 | — | 231 ± 162 | 0 ± 0 | 0 ± 0 | 0 ± 0 |
| Day 35 | — | 496 ± 345 | 0 ± 0 | 0 ± 0 | 32 ± 32 |
| Day 37 | — | 335 ± 335 | 0 ± 0 | 0 ± 0 | 33 ± 33 |
| Day 39 | — | 0 ± 0 | 0 ± 0 | 0 ± 0 | 24 ± 24 |
| Day 42 | — | 0 ± 0 | 0 ± 0 | 0 ± 0 | 105 ± 57 |
| Day 44 | — | 0 ± 0 | 0 ± 0 | 0 ± 0 | 143 ± 79 |
| Day 46 | — | 30 ± 30 | 0 ± 0 | 0 ± 0 | 262 ± 95 |
| Day 49 | — | 46 ± 46 | 0 ± 0 | 0 ± 0 | 438 ± 171 |
| Day 51 | — | 50 ± 50 | 0 ± 0 | 0 ± 0 | 550 ± 212 |
| Day 53 | — | 93 ± 93 | 0 ± 0 | 0 ± 0 | 732 ± 269 |
| Day 56 | — | 147 ± 147 | 0 ± 0 | 0 ± 0 | 953 ± 410 |
| Day 58 | — | 198 ± 198 | 0 ± 0 | 0 ± 0 | 445 ± 323 |
| Day 60 | — | 239 ± 239 | 0 ± 0 | 0 ± 0 | 604 ± 457 |
| Day 63 | — | 589 ± 589 | 0 ± 0 | 0 ± 0 | 435 ± 435 |
| Day 67 | — | 43 ± 32 | 0 ± 0 | 0 ± 0 | 0 ± 0 |
| Day 70 | — | 119 ± 80 | 0 ± 0 | 0 ± 0 | 115 ± 115 |
| Day 72 | — | 207 ± 149 | 0 ± 0 | 0 ± 0 | 175 ± 175 |
| Day 74 | — | 250 ± 168 | 0 ± 0 | 0 ± 0 | 176 ± 176 |
| Day 78 | — | 683 ± 477 | 0 ± 0 | 0 ± 0 | 709 ± 709 |
| Day 81 | — | — | 0 ± 0 | 0 ± 0 | — |

11B. TF-1 AML Xenografts

Figure 4:
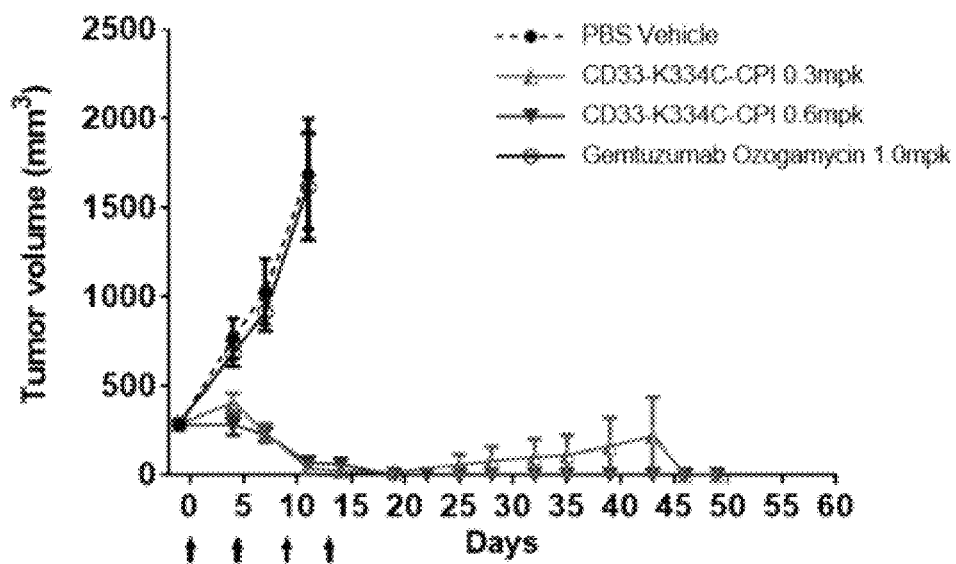
FIG. 4 shows the efficacy of CD33 ADC conjugated at position 334 (CD33-K334C-CPI) in a TF-1 xenograft model. The data demonstrates that the CD33-K334C-CPI ADC inhibited tumor growth more potently than Gemtuzumab Ozogamicin (calicheamicin conjugate; control).
Figure 5:
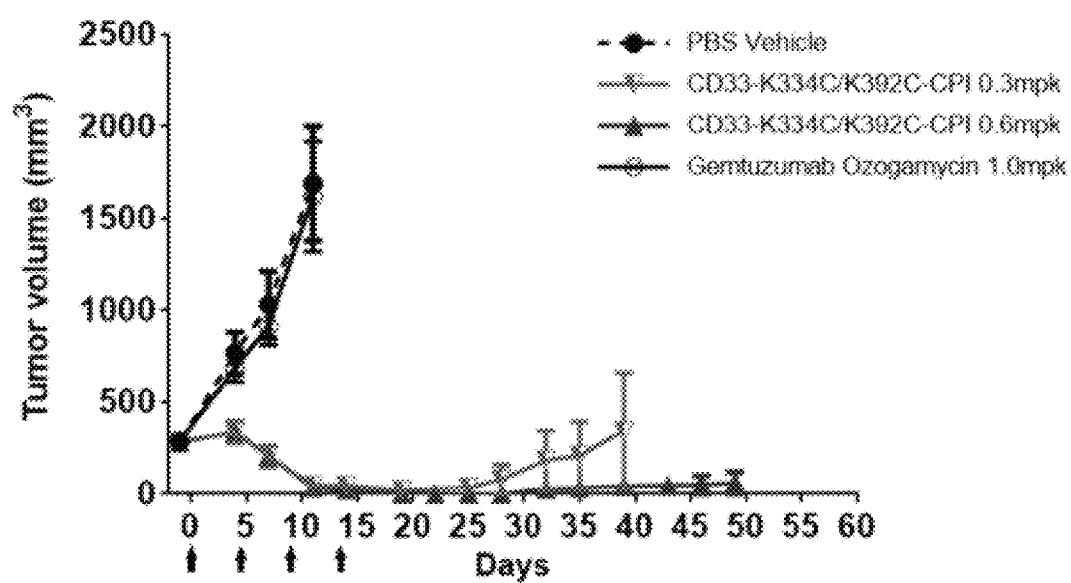
FIG. 5 demonstrates the efficacy of CD33 ADC conjugated at positions 334 and 392 (CD33-K334C/K392C-CPI) in a TF-1 xenograft model. The data demonstrates that the CD33-K334C/K392C-CPI ADC inhibited tumor growth more potently than Gemtuzumab Ozogamicin (calicheamicin conjugate; control).

The effects of the CD33-K334C-CPI ADC and CD33-K334C/K392C-CPI ADC on the in vivo growth of human tumors were examined in immunodeficient mice. For subcutaneous (sc) AML models, $10 \times 10^6$ TF-1 cells were implanted subcutaneously in the flank of female Athymic nu/nu mice. When the tumors reached an average volume of 300 mm³, animals were staged to ensure uniformity of the tumor size among various treatment groups. The TF-1 AML sc xenograft model was dosed intravenously four times every four days (Q4dx4) with PBS vehicle, anti-CD33 ADC, and gemtuzumab ozogamicin (control calicheamicin conjugate as comparator) at the doses provided in Table 12. FIG. 4 and FIG. 5 shows a graph of the data from Table 15 of the CD33-K334C-CPI ADC and CD33-K334C/K392C-CPI at 0.3, 0.6 and 1 mg/kg doses compared to control ADC Gemtuzumab Ozogamicin (1 mg/kg) and PBS vehicle.

The data demonstrates that both CD33-K334C-CPI ADC and CD33-K334C/K392C-CPI inhibited growth of TF-1 AML xenograft tumors. The 1 mg/kg dose of the CD33-K334C-CPI ADC and 0.3 mpk dose of the CD33-K334C/K392C-CPI were the most potent tested in this study. As expected, DAR 4 CD33-K334C/K392C-CPI ADC is more potent than DAR 2 CD33-K334C-CPI ADC. Furthermore, the data shows that the CD33-K334C-CPI ADC inhibited tumor growth more potently than gemtuzumab ozogamicin (calicheamicin conjugate; positive control) indicating a greater efficacy than a calicheamicin conjugated anti-CD33 ADC.

TABLE 15

TF-1 AML Xenografts - CD33 ADCs

| DOSE (mg/kg) | PBS 0 | CD33-K334C-CPI 0.3 | CD33-K334C-CPI 0.6 | CD33-K334C-CPI 1 | CD33-K334C/K392C-CPI 0.3 | CD33-K334C/K392C-CPI 0.6 | CD33-K334C/K392C-CPI 1 | Gemtuzumab Ozogamicin 1 |
|---|---|---|---|---|---|---|---|---|
| Day −1 | 284 ± 11 | 286 ± 15 | 282 ± 20 | 284 ± 18 | 285 ± 26 | 281 ± 18 | 281 ± 28 | 289 ± 15 |
| Day 4 | 767 ± 113 | 407 ± 52 | 283 ± 58 | 291 ± 45 | 337 ± 61 | 339 ± 36 | 286 ± 60 | 684 ± 73 |
| Day 7 | 1031 ± 183 | 238 ± 51 | 229 ± 45 | 189 ± 37 | 204 ± 60 | 209 ± 35 | 119 ± 42 | 917 ± 107 |

TABLE 15-continued

TF-1 AML Xenografts - CD33 ADCs

| DOSE (mg/kg) | PBS 0 | CD33-K334C-CPI 0.3 | 0.6 | 1 | CD33--K334C/K392C-CPI 0.3 | 0.6 | 1 | Gemtuzumab Ozogamicin 1 |
|---|---|---|---|---|---|---|---|---|
| Day 11 | 1690 ± 310 | 38 ± 25 | 71 ± 30 | 0 ± 0 | 47 ± 37 | 35 ± 24 | 14 ± 14 | 1621 ± 300 |
| Day 14 | 1468 ± 260 | 26 ± 26 | 62 ± 26 | 0 ± 0 | 45 ± 32 | 23 ± 23 | 17 ± 17 | 1652 ± 390 |
| Day 19 | — | 16 ± 16 | 0 ± 0 | 0 ± 0 | 21 ± 21 | 0 ± 0 | 0 ± 0 | — |
| Day 22 | — | 0 ± 0 | 0 ± 0 | 0 ± 0 | 0 ± 0 | 0 ± 0 | 0 ± 0 | — |
| Day 25 | — | 59 ± 59 | 0 ± 0 | 0 ± 0 | 35 ± 35 | 0 ± 0 | 0 ± 0 | — |
| Day 28 | — | 79 ± 79 | 0 ± 0 | 0 ± 0 | 79 ± 79 | 0 ± 0 | 0 ± 0 | — |
| Day 32 | — | 102 ± 102 | 0 ± 0 | 0 ± 0 | 184 ± 163 | 27 ± 27 | 0 ± 0 | — |
| Day 35 | — | 113 ± 113 | 0 ± 0 | 0 ± 0 | 210 ± 186 | 33 ± 33 | 0 ± 0 | — |
| Day 39 | — | 162 ± 162 | 0 ± 0 | 0 ± 0 | 345 ± 316 | 42 ± 42 | 0 ± 0 | — |
| Day 43 | — | 219 ± 219 | 0 ± 0 | 0 ± 0 | 45 ± 45 | 47 ± 47 | 0 ± 0 | — |
| Day 46 | — | 0 ± 0 | 0 ± 0 | 0 ± 0 | 63 ± 63 | 50 ± 50 | 0 ± 0 | — |
| Day 49 | — | 0 ± 0 | 0 ± 0 | 0 ± 0 | 43 ± 43 | 60 ± 60 | 0 ± 0 | — |
| Day 54 | — | 0 ± 0 | 0 ± 0 | 0 ± 0 | 67 ± 67 | 76 ± 76 | 0 ± 0 | — |
| Day 60 | — | 0 ± 0 | 0 ± 0 | 0 ± 0 | 78 ± 78 | 100 ± 100 | 0 ± 0 | — |
| Day 67 | — | 0 ± 0 | 0 ± 0 | 0 ± 0 | 93 ± 93 | 151 ± 151 | 0 ± 0 | — |
| Day 74 | — | 0 ± 0 | 0 ± 0 | 0 ± 0 | 95 ± 95 | 241 ± 241 | 0 ± 0 | — |
| Day 83 | — | 0 ± 0 | 0 ± 0 | 0 ± 0 | 123 ± 123 | 0 ± 0 | 0 ± 0 | — |

Figure 6:
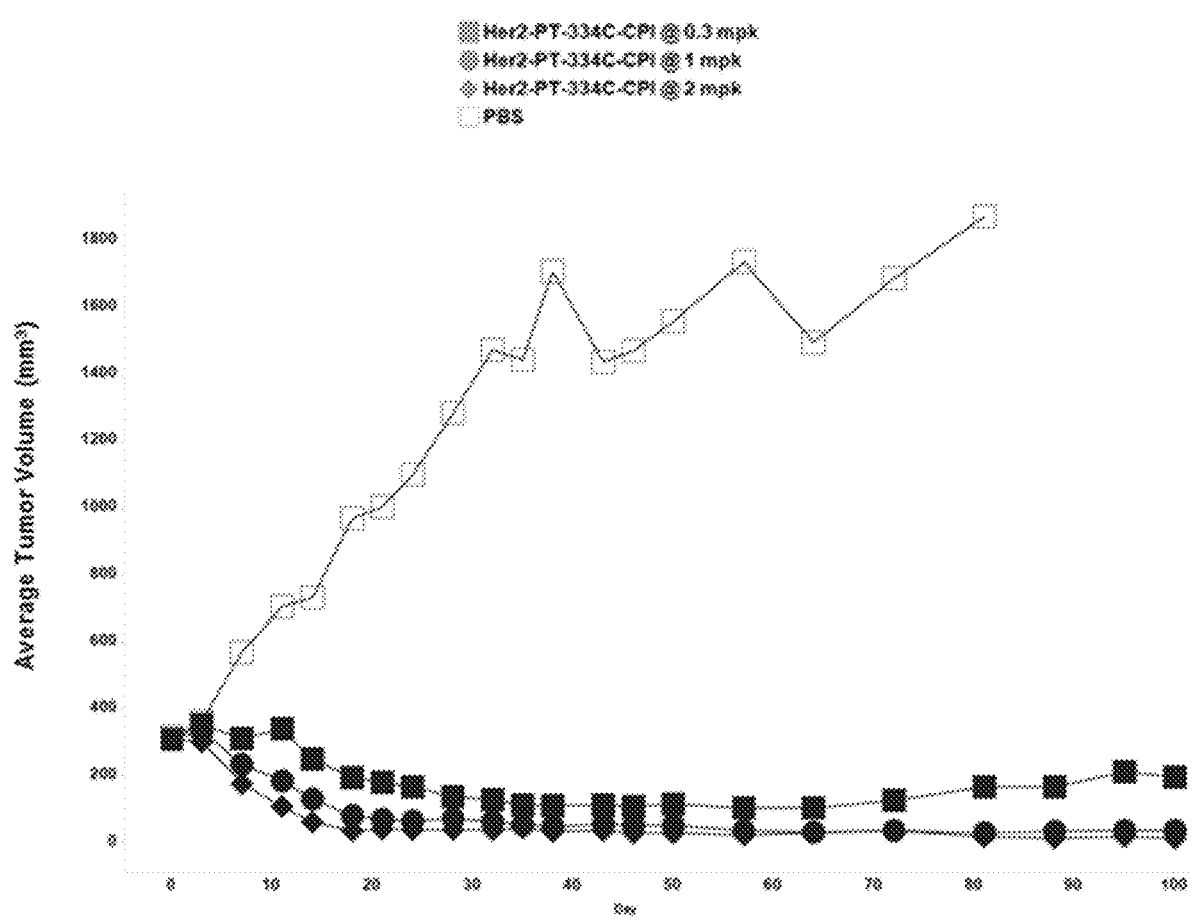
FIG. 6 demonstrates an assessment of ADC activity in a Her2 positive tumor xenograft model. These data establishes that Her2 ADC conjugated at position 334 (Her2-K334C-CPI) and administered at 1 and 2 mg/kg provided long lasting regressions of the tumor.

Example 12. Assessment of ADC Activity in a Her2 Positive Tumor Xenograft Model An in vivo efficacy study of the Her2-K334C-CPI ADC was performed with a Her2-expressing xenograft model using the N87 cell line. For this study, 7.5 million tumor cells in 50% matrigel were implanted subcutaneously into 6-8 weeks old nude mice until the tumor sizes reach between 250 and 350 mm3. Dosing was done through bolus tail vein injection. The N87 xenograft model was dosed intravenously four times every four days (Q4dx4) with PBS vehicle or with Her2-K334C-CPI ADC at 0.3, 1.0, or 2.0 mg/kg, as shown below in Table 13 and FIG. 6. The tumors were measured at least once a week and their volume was calculated with the formula: tumor volume (mm$^3$)=0.5× (tumor width$^2$)(tumor length). The mean tumor volumes (±S.E.M.) for each treatment group were calculated having a maximum of 10 animals and a minimum of 6 animals to be included. Mean tumor volumes are reported in Table 16. All animal experiments were conducted in a facility accredited by the Association for Assessment of Laboratory Animal Care under Institutional Animal Care and Use Committee guidelines and appropriate animal research approval.

These data demonstrated that Her2-K334C-CPI ADC inhibited growth of N87 xenograft in a dose-dependent manner. Doses of 1 and 2 mpk provided long lasting regressions of the tumor.

TABLE 16

N87 Xenografts - Her2 ADC

N87 xenografts, mean tumor volume (mm3 +/− SEM) Q4dx4

| | PBS | Her2-K334C-CPI Dose (mg/kg) | | |
|---|---|---|---|---|
| | 0.00 | 0.30 | 1.00 | 2.00 |
| Day 0 | 316 +/− 15 | 309 +/− 13 | 309 +/− 13 | 309 +/− 19 |
| Day 3 | 364 +/− 14 | 354 +/− 12 | 332 +/− 20 | 302 +/− 12 |
| Day 7 | 569 +/− 22 | 310 +/− 15 | 235 +/− 20 | 176 +/− 9 |
| Day 11 | 707 +/− 46 | 341 +/− 24 | 185 +/− 23 | 109 +/− 6 |
| Day 14 | 733 +/− 38 | 251 +/− 17 | 131 +/− 18 | 63 +/− 4 |
| Day 18 | 969 +/− 66 | 194 +/− 15 | 82 +/− 13 | 37 +/− 3 |
| Day 21 | 1002 +/− 59 | 180 +/− 9 | 71 +/− 14 | 42 +/− 5 |
| Day 24 | 1099 +/− 83 | 168 +/− 11 | 66 +/− 11 | 39 +/− 4 |
| Day 28 | 1282 +/− 83 | 138 +/− 9 | 73 +/− 12 | 39 +/− 6 |
| Day 32 | 1472 +/− 114 | 128 +/− 7 | 63 +/− 8 | 39 +/− 7 |
| Day 35 | 1443 +/− 107 | 114 +/− 9 | 55 +/− 6 | 43 +/− 5 |
| Day 38 | 1705 +/− 123 | 111 +/− 8 | 49 +/− 4 | 35 +/− 5 |
| Day 43 | 1435 +/− 116 | 113 +/− 12 | 57 +/− 6 | 37 +/− 4 |
| Day 46 | 1470 +/− 132 | 108 +/− 12 | 52 +/− 7 | 31 +/− 4 |
| Day 50 | 1556 +/− 192 | 116 +/− 14 | 53 +/− 4 | 30 +/− 5 |
| Day 57 | 1734 +/− 207 | 103 +/− 13 | 38 +/− 4 | 23 +/− 4 |
| Day 64 | 1493 +/− 89 | 105 +/− 19 | 33 +/− 4 | 31 +/− 5 |
| Day 72 | 1686 +/− 5 | 126 +/− 23 | 36 +/− 5 | 37 +/− 6 |
| Day 81 | 1869 +/− 140 | 168 +/− 35 | 31 +/− 5 | 18 +/− 5 |
| Day 88 | — | 167 +/− 38 | 35 +/− 6 | 15 +/− 7 |
| Day 95 | — | 212 +/− 53 | 37 +/− 6 | 19 +/− 5 |
| Day 100 | — | 196 +/− 50 | 37 +/− 10 | 14 +/− 4 |

Example 13. Pharmacokinetics of CD33-K334C-CPI and CD33-K392C-CPI ADCs nu/nu mice were dosed with CD33-K392C-CPI or CD33-K334C-CPI at 3 mg/kg using intravenous administration. Quantitation of the total antibody concentrations in mouse plasma was achieved using Gyrolab™ and Bioaffy 1000 CDs with fluorescence detection. Briefly, the capture protein was BIOT sheep anti-hIgG (The Binding Site, cat# AU003.MCUS01) at 100 µg/mL and the detection antibody was Alexa Fluor 647 goat anti-hIgG (Bethyl, cat#A80-319A) at 2 µg/mL. The quantitation range was 0.0390 to 80 µg/mL, and the lower limit of quantitation was 0.100 µg/mL in plasma. DAR is determined using mass spectrometry and the normalized average DAR was multiplied by the mAb concentration and the resulting exposure was termed the ConjPL (conjugated payload).

Figure 7:
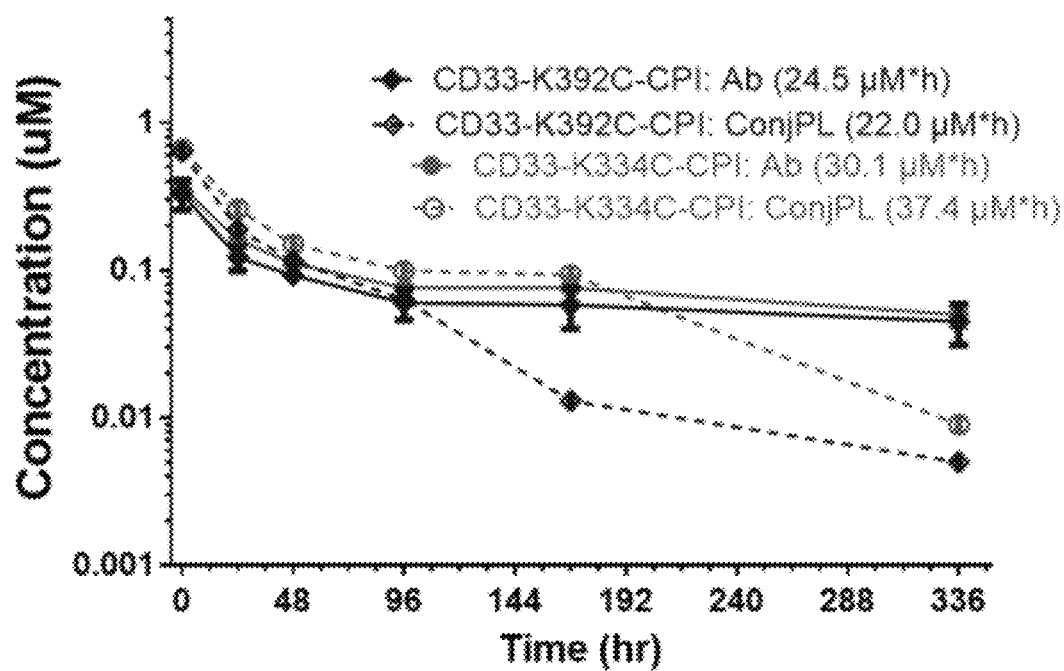
FIG. 7 depicts the pharmacokinetics of CD33-K334C-CPI and CD33-K392C-CPI in cynomolgus monkeys.

The total Ab concentrations were similar through the 14 day collection period while the conjugated payload concentrations paralleled those of the Ab for the first few days before decreasing after 7 or 14 days. These profiles (FIG. 7) suggest a high degree of linker payload stability, relatively better for CD33-K334C-CPI compared to CD33-K392C-CPI.

TABLE 17

Residue numbering chart

| Heavy Chain (CH2 domain, except A114) | | | | Heavy Chain (CH3 domain) | | | |
| --- | --- | --- | --- | --- | --- | --- | --- |
| Residue | EU index | Kabat numbering | Position at SEQ ID NO: 25 | Residue | EU index | Kabat numbering | Position at SEQ ID NO: 25 |
| A114 | 118 | 114 | N/A | E345 | 345 | 366 | 115 |
| K246 | 246 | 259 | 16 | Q347 | 347 | 368 | 117 |
| D249 | 249 | 262 | 19 | S354 | 354 | 375 | 124 |
| D265 | 265 | 278 | 35 | R355 | 355 | 376 | 125 |
| S267 | 267 | 280 | 37 | L358 | 358 | 381 | 128 |
| D270 | 270 | 283 | 40 | K360 | 360 | 383 | 130 |
| N276 | 276 | 289 | 46 | Q362 | 362 | 385 | 132 |
| Y278 | 278 | 291 | 48 | K370 | 370 | 393 | 140 |
| E283 | 283 | 300 | 53 | Y373 | 373 | 396 | 143 |
| K290 | 290 | 307 | 60 | S375 | 375 | 398 | 145 |
| R292 | 292 | 309 | 62 | D376 | 376 | 399 | 146 |
| E293 | 293 | 310 | 63 | A378 | 378 | 401 | 148 |
| E294 | 294 | 311 | 64 | E380 | 380 | 405 | 150 |
| Y300 | 300 | 319 | 70 | E382 | 382 | 407 | 152 |
| V302 | 302 | 321 | 72 | Q386 | 386 | 414 | 156 |
| V303 | 303 | 322 | 73 | E388 | 388 | 416 | 158 |
| L314 | 314 | 333 | 84 | N390 | 390 | 418 | 160 |
| N315 | 315 | 334 | 85 | K392 | 392 | 420 | 162 |
| E318 | 318 | 337 | 88 | T393 | 393 | 421 | 163 |
| K320 | 320 | 339 | 90 | D401 | 401 | 430 | 171 |
| I332 | 332 | 351 | 102 | F404 | 404 | 435 | 174 |
| E333 | 333 | 352 | 103 | T411 | 411 | 442 | 181 |
| K334 | 334 | 353 | 104 | D413 | 413 | 444 | 183 |
| I336 | 336 | 355 | 106 | K414 | 414 | 445 | 184 |
| | | | | R416 | 416 | 447 | 186 |
| | | | | Q418 | 418 | 449 | 188 |
| | | | | Q419 | 419 | 450 | 189 |
| | | | | N421 | 421 | 452 | 191 |
| | | | | M428 | 428 | 459 | 198 |
| | | | | A431 | 431 | 462 | 201 |
| | | | | L432 | 432 | 463 | 202 |
| | | | | T437 | 437 | 468 | 207 |
| | | | | Q438 | 438 | 469 | 208 |
| | | | | K439 | 439 | 470 | 209 |
| | | | | L443 | 443 | 474 | 213 |
| | | | | S444 | 444 | 475 | 214 |

| Kappa Light Chain | | | | Lambda Light Chain | | | |
| --- | --- | --- | --- | --- | --- | --- | --- |
| Residue | EU index | Kabat numbering | Position at SEQ ID No. 30 | Residue | EU index | Kabat numbering | Position at SEQ ID No. 31 |
| A111 | 111 | 111 | 4 | K110 | N/A | 110 | 4 |
| K149 | 149 | 149 | 42 | A111 | N/A | 111 | 5 |
| K183 | 183 | 183 | 76 | L125 | N/A | 125 | 19 |
| K188 | 188 | 188 | 81 | K149 | N/A | 149 | 43 |
| K207 | 207 | 207 | 100 | V155 | N/A | 155 | 49 |
| N210 | 210 | 210 | 103 | G158 | N/A | 158 | 52 |
| | | | | T161 | N/A | 161 | 55 |
| | | | | P183 | N/A | 183 | 76 |
| | | | | Q185 | N/A | 185 | 78 |
| | | | | S188 | N/A | 188 | 81 |
| | | | | H189 | N/A | 189 | 82 |
| | | | | S191 | N/A | 191 | 84 |
| | | | | T197 | N/A | 197 | 90 |
| | | | | V205 | N/A | 205 | 96 |
| | | | | E206 | N/A | 206 | 97 |
| | | | | K207 | N/A | 207 | 98 |
| | | | | T208 | N/A | 208 | 99 |
| | | | | A210 | N/A | 210 | 101 |

TABLE 18

| | Sequences | |
|---|---|---|
| 1 | CD33 h11A1 VH Protein | EVQLVESGGGLVQPGGSLRLSCAASGYIFTDYVTHW VRQAPGKGLEWIAYINPYNAGTKYNERFKGRFTISS DNAKNSLYLQMNSLRAEDTAVYYCARDYRYEIYGMD YWGQGTLVTVSS |
| 2 | CD33 h11A1 VH DNA | GAGGTGCAGCTGGTGGAGTCTGGCGGCGGACTGGTG CAGCCTGGCGGCTCTCTGAGACTGTCTTGTGCCGCC TCCGGATACATATTCACTGACTATGTTACACACTGG GTGAGGCAGGCCCCTGGCAAGGGCCTGGAGTGGATC GCCTATATTAATCCTTACAATGATGGTACTAAATAC AATGAGAGGTTCAAAGGCCGGTTCACCATCTCCAGC GACAACGCCAAGAACTCCCTGTACCTCCAGATGAAC TCCCTGAGGGCCGAGGATACCGCCGTGTACTACTGT GCCAGAGATTATAGGTACGAAATCTATGGTATGGAC TACTGGGGCCAGGGCACCCTGGTGACCGTGTCCTCT |
| 3 | CD33 h11A1 VL Protein | DIQLTQSPSSLSASVGDRVTITCRASSSVGYMHWYQ QKPGKAPKLLIYDISQLASGVPSRFSGSGSGTDFIL TISSLQPEDFATYYCQLWSSNPLTFGGGTKVEIK |
| 4 | CD33 h11A1 VL DNA | GACATCCAGCTGACCCAGTCTCCATCCTCCCTGTCT GCATCTGTAGGAGACAGAGTCACCATCACTTGCAGA GCCAGTTCAAGTGTAGGTTACATGCACTGGTATCAG CAGAAACCAGGGAAAGCCCCTAAGCTCCTGATCTAT GACACATCCCAACTGGCTTCTGGGGTCCCATCAAGG TTCAGTGGCAGTGGATCTGGGACAGATTTCACTCTC ACCATCAGCAGTCTGCAACCTGAAGATTTTGCAACT TACTACTGTCAGCTGTGGAGCAGTAACCCGCTCACG TTCGGCGGAGGGACCAAGGTGGAGATCAAA |
| 5 | CD33 h11A1 VH CDR1 Kabat | DYVTH |
| 6 | CD33 h11A1 VH CDR1 Chothia | GYIFTDY |
| 7 | CD33 h11A1 VH CDR1 DNA Kabat | GACTATGTTACACAC |
| 8 | CD33 h11A1 VH CDR1 DNA Chothia | GGATACATATTCACTGACTAT |
| 9 | CD33 h11A1 VH CDR2 Kabat | YINPYNAGTKYNERFKG |
| 10 | CD33 h11A1 VH CDR2 Chothia | NPYNAG |
| 11 | CD33 h11A1 VH CDR2 DNA Kabat | TATATTAATCCTTACAATGCTGGTACTAAATACAAT GAGAGGTTCAAAGGC |
| 12 | CD33 h11A1 VH CDR2 DNA Chothia | AATCCTTACAATGCTGGT |
| 13 | CD33 h11A1 VH CDR3 Kabat and Chothia | DYRYEIYGMDY |
| 14 | CD33 h11A1 VH CDR3 DNA Kabat and Chothia | GATTATAGGTACGAAATCTATGGTATGGACTAC |
| 15 | CD33 h11A1 HC Protein | EVQLVESGGGLVQPGGSLRLSCAASGYIFTDYVTHW VRQAPGKGLEWIAYINPYNAGTKYNERFKGRFTISS DNAKNSLYLQMNSLRAEDTAVYYCARDYRYEIYGMD |

TABLE 18-continued

| | | Sequences |
|---|---|---|
| | | YWGQGTLVTVSSASTKGPSVFPLAPSSKSTSGGTAA
LGCLVKDYFPEPVTVSWNSGALTSGVHTFPAVLQSS
GLYSLSSVVTVPSSSLGTQTYICNVNHKPSNTKVDK
KVEPKSCDRTHTCPPCPAPELLGGPSVFLFPPKPKD
TLMISRTPEVTCVVVDVSHEDPEVKFNWYVDGVEVH
NAKTKPRELLQGSTYRVVSVLTVLHQDWLNGKEYKC
KVSNKALPAPIEKTISKAKGQPREPQVYTLPPSREE
MTKNQVSLICLVKGFYPSDIAVEWESNGQPENNYKT
TPPVLDSDGSFFLYSKLTVDKSRWQQGNVFSCSVMH
EALHNHYTQKSLSLSPG |
| 16 | CD33
h11A1 HC DNA | GAGGTGCAGCTGGTGGAGTCTGGCGGCGGACTGGTG
CAGCCTGGCGGCTCTCTGAGACTGTCTTGTGCCGCC
TCCGGATACATATTCACTGACTATGTTACACACTGG
GTGAGGCAGGCCCCTGGCAAGGGCCTGGAGTGGATC
GCCTATATTAATCCTTACAATGCTGGTACTAAATAC
AATGAGAGGTTCAAAGGCCGGTTCACCATCTCCAGC
GACAACGCCAAGAACTCCCTGTACCTCCAGATGAAC
TCCCTGAGGGCCGAGGATACCGCCGTGTACTACTGT
GCCAGAGATTATAGGTACGAAATCTATGGTATGGAC
TACTGGGGCCAGGGCACCCTGGTGACCGTGTCCTCT
GCGTCGACCAAGGGCCCATCGGTCTTCCCCCTGGCA
CCCTCCTCCAAGAGCACCTCTGGGGGCACAGCGGCC
CTGGGCTGCCTGGTCAAGGACTACTTCCCCGAACCG
GTGACGGTGTCGTGGAACTCAGGCGCCCTGACCAGC
GGCGTGCACACCTTCCCGGCTGTCCTACAGTCCTCA
GGACTCTACTCCCTCAGCAGCGTAGTGACCGTGCCC
TCCAGCAGCTTGGGCACCCAGACCTACATCTGCAAC
GTGAATCACAAGCCCAGCAACACCAAGGTGGACAAG
AAAGTTGAGCCCAAATCTTGTGACCGCACTCACACA
TGCCCACCGTGCCCAGCACCTGAACTCCTGGGGGGA
CCGTCAGTCTTCCTCTTCCCCCCAAAACCCAAGGAC
ACCCTCATGATCTCCCGGACCCCTGAGGTCACATGC
GTGGTGGTGGACGTGAGCCACGAAGACCCTGAGGTC
AAGTTCAACTGGTACGTGGACGGCGTGGAGGTGCAT
AATGCCAAGACAAAGCCGCGGGAGCTGCTGCAGGGG
AGCACGTACCGTGTGGTCAGCGTCCTCACCGTCCTG
CACCAGGACTGGCTGAATGGCAAGGAGTACAAGTGC
AAGGTCTCCAACAAAGCCCTCCCAGCCCCCATCGAG
AAAACCATCTCCAAAGCCAAAGGGCAGCCCCGAGAA
CCACAGGTGTACACCCTGCCCCCATCCCGGGAGGAG
ATGACCAAGAACCAGGTCAGCCTGACCTGCCTGGTC
AAAGGCTTCTATCCCAGCGACATCGCCGTGGAGTGG
GAGAGCAATGGGCAGCCGGAGAACAACTACAAGACC
ACGCCTCCCGTGCTGGACTCCGACGGCTCCTTCTTC
CTCTATAGCAAGCTCACCGTGGACAAGAGCAGGTGG
CAGCAGGGGAACGTCTTCTCATGCTCCGTGATGCAT
GAGGCTCTGCACAACCACTACACGCAGAAGAGCCTC
TCCCTGTCCCCCGGATAGTAG |
| 17 | CD33
h11A1 VL CDR1
Protein
Kabat and Chothia | RASSSVGYMH |
| 18 | CD33
h11A1 VL CDR1
DNA
Kabat and Chothia | AGAGCCAGTTCAAGTGTAGGTTACATGCAC |
| 19 | CD33
h11A1 VL CDR2
Protein
Kabat and Chothia | DTSQLAS |
| 20 | CD33
h11A1 VL CDR2
DNA
Kabat and Chothia | GACACATCCCAACTGGCTTCT |
| 21 | CD33
h11A1 VL CDR3
Protein
Kabat and Chothia | QLWSSNPLT |

TABLE 18-continued

| | | Sequences |
|---|---|---|
| 22 | CD33 h11A1 VL CDR3 DNA Kabat and Chothia | CAGCTGTGGAGCAGTAACCCGCTCACG |
| 23 | CD33 h11A1 LC Protein | DIQLTQSPSSLSASVGDRVTITCRASSSVGYMHWYQ QKPGKAPKLLIYDTSQLASGVPSRFSGSGSGTDFTL TISSLQPEDFATYYCQLWSSNPLTFGGGTKVEIKRT VAAPSVFIFPPSDEQLKSGTASVVCLLNNFYPREAK VQWKVDNALQSGNSQESVTEQDSKDSTYSLSSTLTL SKADYEKHKVYACEVTHQGLSSPVTKSFNRGEC |
| 24 | CD33 h11A1 LC DNA | GACATCCAGCTGACCCAGTCTCCATCCTCCCTGTCT GCATCTGTAGGAGACAGAGTCACCATCACTTGCAGA GCCAGTTCAAGTGTAGGTTACATGCACTGGTATCAG CAGAAACCAGGGAAAGCCCCTAAGCTCCTGATCTAT GACACATCCCAACTGGCTTCTGGGGTCCCATCAAGG TTCAGTGGCAGTGGATCTGGGACAGATTTCACTCTC ACCATCAGCAGTCTGCAACCTGAAGATTTTGCAACT TACTACTGTCAGCTGTGGAGCAGTAACCCGCTCACG TTCGGCGGAGGGACCAAGGTGGAGATCAAACGTACT GTGGCTGCACCATCTGTCTTCATCTTCCCGCCATCT GATGAGCAGTTGAAATCTGGAACTGCCTCTGTTGTG TGCCTGCTGAATAACTTCTATCCCAGAGAGGCCAAA GTACAGTGGAAGGTGGATAACGCCCTCCAATCGGGT AACTCCCAGGAGAGTGTCACAGAGCAGGACAGCAAG GACAGCACCTACAGCCTCAGCAGCACCCTGACGCTG AGCAAAGCAGACTACGAGAAACACAAAGTCTACGCC TGCGAAGTCACCCATCAGGGCCTGAGCTCGCCCGTC ACAAAGAGCTTCAACAGGGGAGAGTGT |
| 25 | IgG1 HC; CH2 domain | APELLGGPSVFLFPPKPKDTLMISRTPEVTCVVVDV SHEDPEVKFNWYVDGVEVHNAKTKPREEQYNSTYRV VSVLTVLHQDWLNGKEYKCKVSNKALPAPIEKTISK AK |
| 26 | IgG1 HC; CH2 and CH3 domains | APELLGGPSVFLFPPKPKDTLMISRTPEVTCVVVDV SHEDPEVKFNWYVDGVEVHNAKTKPREEQYNSTYRV VSVLTVLHQDWLNGKEYKCKVSNKALPAPIEKTISK AKGQPREPQVYTLPPSRDELTKNQVSLTCLVKGFYP SDIAVEWESNGQPENNYKTIPPVLDSDGSFFLYSKL TVDKSRWQQGNVFSCSVMHEALHNHYTQKSLSLSPG K |
| 27 | IgG1 K334C | ASTKGPSVFPLAPSSKSTSGGTAALGCLVKDYFPEP VTVSWNSGALTSGVHTFPAVLQSSGLYSLSSVVTVP SSSLGTQTYICNVNHKPSNTKVDKKVEPKSCDKTHT CPPCPAPELLGGPSVFLFPPKPKDTLMISRTPEVTC VVVDVSHEDPEVKFNWYVDGVEVHNAKTKPREEQYN STYRVVSVLTVLHQDWLNGKEYKCKVSNKALPAPIE CTISKAKGQPREPLVYTLPPSREEMTKNQVSLTCLV KGFYPSDIAVEWESNGQPENNYLTTPPVLDSDGSFF LYSKLTVDKSRWQQGNVFSCSVMHEALHNHYTQKSL SLSPGK |
| 28 | IgG1-K392C | ASTKGPSVFPLAPSSKSTSGGTAALGCLVKDYFPEP VTVSWNSGALTSGVHTFPAVLQSSGLYSLSSVVTVP SSSLGTQTYICNVNHKPSNTKVDKKVEPKSCDKTHT CPPCPAPELLGGPSVFLFPPKPKDTLMISRTPEVTC VVVDVSHEDPEVKFNWYVDGVEVHNAKTKPREEQYN STYRVVSVLTVLHQDWLNGKEYKCKVSNKALPAPIE KTISKAKGQPREPLVYTLPPSREEMTKNQVSLTCLV KGFYPSDIAVEWESNGQPENNYCTTPPVLDSDGSFF LYSKLTVDKSRWQQGNVFSCSVMHEALHNHYTQKSL SLSPGK |
| 29 | IgG1-K334C/K392C | ASTKGPSVFPLAPSSKSTSGGTAALGCLVKDYFPEP VTVSWNSGALTSGVHTFPAVLQSSGLYSLSSVVTVP SSSLGTQTYICNVNHKPSNTKVDKKVEPKSCDKTHT CPPCPAPELLGGPSVFLFPPKPKDTLMISRTPEVTC VVVDVSHEDPEVKFNWYVDGVEVHNAKTKPREEQYN STYRVVSVLTVLHQDWLNGKEYKCKVSNKALPAPIE CTISKAKGQPREPQVYTLPPSREEMTKNQVSLTCLV KGFYPSDIAVEWESNGQPENNYCTTPPVLDSDGSFF LYSKLTVDKSRWQQGNVFSCSVMHEALHNHYTQKSL SLSPGK |

TABLE 18-continued

| | | Sequences |
|---|---|---|
| 30 | Cκ constant domain | RTVAAPSVFIFPPSDEQLKSGTASVVCLLNNFYPRE AKVQWKVDNALQSGNSQESVTEQDSKDSTYSLSSTL TLSKADYE KHKVYACEVTHQGLSSPVTKSFNRGEC |
| 31 | Cλ constant domain | GQPKANPTVTLFPPSSEELQANKATLVCLISDFYPG AVTVAWKADGSPVKAGVETTKPSKQSNNKYAASSYL SLTPEQWK SHRSYSCQVTHEGSTVEKTVAPTECS |
| 32 | CD33-K334C h11A1 HC Protein | EVQLVESGGGLVQPGGSLRLSCAASGYIFTDYVTHW VRQAPGKGLEWIAYINPYNAGTKYNERFKGRFTISS DNAKNSLYLQMNSLRAEDTAVYYCARDYRYEIYGMD YWGQGTLVTVSSASTKGPSVFPLAPSSKSTSGGTAA LGCLVKDYFPEPVTVSWNSGALTSGVHTFPAVLQSS GLYSLSSVVTVPSSSLGTQTYICNVNHKPSNTKVDK KVEPKSCDRTHTCPPCPAPELLGGPSVFLFPPKPKD TLMISRTPEVTCVVVDVSHEDPEVKFNWYVDGVEVH NAKTKPRELLQGSTYRVVSVLTVLHQDWLNGKEYKC KVSNKALPAPIECTISKAKGQPREPQVYTLPPSREE MTKNQVSLICLVKGFYPSDIAVEWESNGQPENNYKT TPPVLDSDGSFFLYSKLTVDKSRWQQGNVFSCSVMH EALHNHYTQKSLSLSPG |
| 33 | CD33-K392C h11A1 HC Protein | EVQLVESGGGLVQPGGSLRLSCAASGYIFTDYVTHW VRQAPGKGLEWIAYINPYNAGTKYNERFKGRFTISS DNAKNSLYLQMNSLRAEDTAVYYCARDYRYEIYGMD YWGQGTLVTVSSASTKGPSVFPLAPSSKSTSGGTAA LGCLVKDYFPEPVTVSWNSGALTSGVHTFPAVLQSS GLYSLSSVVTVPSSSLGTQTYICNVNHKPSNTKVDK KVEPKSCDRTHTCPPCPAPELLGGPSVFLFPPKPKD TLMISRTPEVTCVVVDVSHEDPEVKFNWYVDGVEVH NAKTKPRELLQGSTYRVVSVLTVLHQDWLNGKEYKC KVSNKALPAPIEKTISKAKGQPREPQVYTLPPSREE MTKNQVSLTCLVKGFYPSDIAVEWESNGQPENNYCT TPPVLDSDGSFFLYSKLTVDKSRWQQGNVFSCSVMH EALHNHYTQKSLSLSPG |
| 34 | CD33-K334C/K392C h11A1 HC Protein | EVQLVESGGGLVQPGGSLRLSCAASGYIFTDYVTHW VRQAPGKGLEWIAYINPYNAGTKYNERFKGRFTISS DNAKNSLYLQMNSLRAEDTAVYYCARDYRYEIYGMD YWGQGTLVTVSSASTKGPSVFPLAPSSKSTSGGTAA LGCLVKDYFPEPVTVSWNSGALTSGVHTFPAVLQSS GLYSLSSVVTVPSSSLGTQTYICNVNHKPSNTKVDK KVEPKSCDRTHTCPPCPAPELLGGPSVFLFPPKPKD TLMISRTPEVTCVVVDVSHEDPEVKFNWYVDGVEVH NAKTKPRELLQGSTYRVVSVLTVLHQDWLNGKEYKC KVSNKALPAPIECTISKAKGQPREPQVYTLPPSREE MTKNQVSLTCLVKGFYPSDIAVEWESNGQPENNYCT TPPVLDSDGSFFLYSKLTVDKSRWQQGNVFSCSVMH EALHNHYTQKSLSLSPG |

The various features and embodiments of the present invention, referred to in individual sections above apply, as appropriate, to other sections, mutatis mutandis. Consequently features specified in one section may be combined with features specified in other sections, as appropriate. All references cited herein, including patents, patent applications, papers, text books, and cited sequence Accession numbers, and the references cited therein are hereby incorporated by reference in their entirety. In the event that one or more of the incorporated literature and similar materials differs from or contradicts this application, including but not limited to defined terms, term usage, described techniques, or the like, this application controls.

The invention claimed is:

1. An antibody drug conjugate of formula Ab-(L-D), wherein:
   (a) Ab is an antibody that binds to CD33, or an antigen binding fragment thereof, comprising an antibody heavy chain constant domain containing an engineered cysteine residue at position 334, according to the numbering of the Eu index of Kabat, wherein the antibody light chain comprises the amino acid sequence of SEQ ID NO:23 and the antibody heavy chain comprises the amino acid sequence of SEQ ID NO:32; and
   (b) L-D is a linker-drug moiety that is attached to the Ab via the engineered cysteine residue, wherein L is a linker comprising vc, mc, MalPeg6, PABC, DMAE, m(H20)c, m(H20)cvc, or a combination thereof; and wherein D is a CPI dimer selected from the group consisting of:

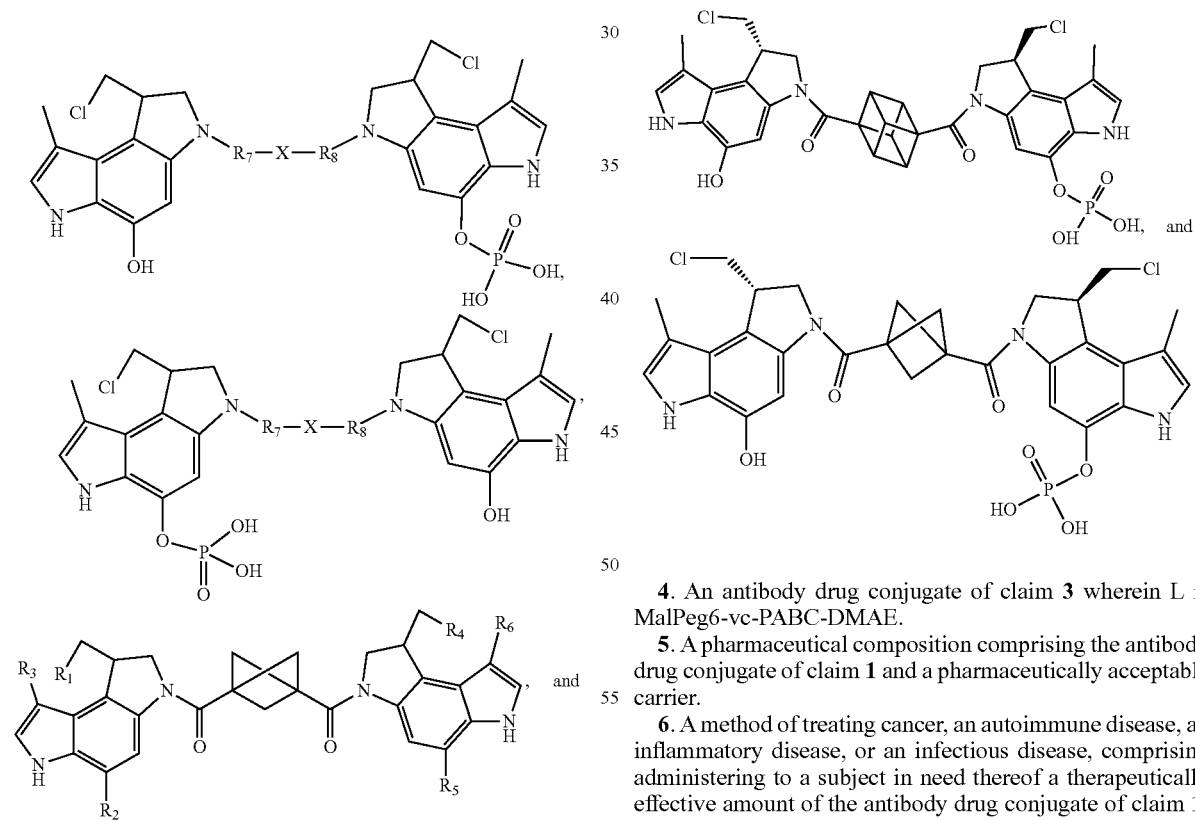

2. The antibody drug conjugate of claim 1, wherein the linker is MalPeg6-vc-PABC-DMAE.

3. The antibody drug conjugate of claim 1, wherein the CPI dimer is selected from the group consisting of:

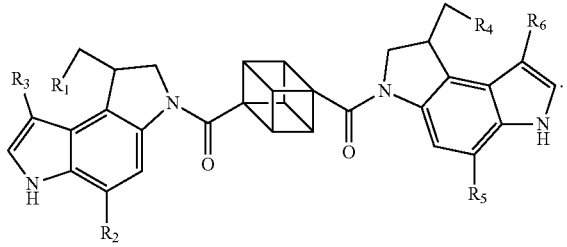

4. An antibody drug conjugate of claim 3 wherein L is MalPeg6-vc-PABC-DMAE.

5. A pharmaceutical composition comprising the antibody drug conjugate of claim 1 and a pharmaceutically acceptable carrier.

6. A method of treating cancer, an autoimmune disease, an inflammatory disease, or an infectious disease, comprising administering to a subject in need thereof a therapeutically effective amount of the antibody drug conjugate of claim 1.

* * * * *

SEQUENCE LISTING

```
<160> NUMBER OF SEQ ID NOS: 34

<210> SEQ ID NO 1
<211> LENGTH: 120
<212> TYPE: PRT
<213> ORGANISM: Artificial Sequence
<220> FEATURE:
<223> OTHER INFORMATION: Synthetic Construct

<400> SEQUENCE: 1

Glu Val Gln Leu Val Glu Ser Gly Gly Gly Leu Val Gln Pro Gly Gly
```

```
1               5                   10                  15
Ser Leu Arg Leu Ser Cys Ala Ala Ser Gly Tyr Ile Phe Thr Asp Tyr
            20                  25                  30

Val Thr His Trp Val Arg Gln Ala Pro Gly Lys Gly Leu Glu Trp Ile
            35                  40                  45

Ala Tyr Ile Asn Pro Tyr Asn Ala Gly Thr Lys Tyr Asn Glu Arg Phe
            50                  55                  60

Lys Gly Arg Phe Thr Ile Ser Ser Asp Asn Ala Lys Asn Ser Leu Tyr
 65                 70                  75                  80

Leu Gln Met Asn Ser Leu Arg Ala Glu Asp Thr Ala Val Tyr Tyr Cys
            85                  90                  95

Ala Arg Asp Tyr Arg Tyr Glu Ile Tyr Gly Met Asp Tyr Trp Gly Gln
            100                 105                 110

Gly Thr Leu Val Thr Val Ser Ser
            115                 120

<210> SEQ ID NO 2
<211> LENGTH: 360
<212> TYPE: DNA
<213> ORGANISM: Artificial Sequence
<220> FEATURE:
<223> OTHER INFORMATION: Synthetic Construct

<400> SEQUENCE: 2
gaggtgcagc tggtggagtc tggcggcgga ctggtgcagc ctggcggctc tctgagactg      60
tcttgtgccg cctccggata catattcact gactatgtta cacactgggt gaggcaggcc     120
cctggcaagg gcctggagtg gatcgcctat attaatcctt acaatgatgg tactaaatac     180
aatgagaggt tcaaaggccg gttcaccatc tccagcgaca cgccaagaa ctccctgtac      240 ctccagatga actccctgag ggccgaggat accgccgtgt actactgtgc cagagattat     300
aggtacgaaa tctatggtat ggactactgg ggccagggca ccctggtgac cgtgtcctct     360

<210> SEQ ID NO 3
<211> LENGTH: 106
<212> TYPE: PRT
<213> ORGANISM: Artificial Sequence
<220> FEATURE:
<223> OTHER INFORMATION: Synthetic Construct

<400> SEQUENCE: 3

Asp Ile Gln Leu Thr Gln Ser Pro Ser Ser Leu Ser Ala Ser Val Gly
 1               5                  10                  15

Asp Arg Val Thr Ile Thr Cys Arg Ala Ser Ser Ser Val Gly Tyr Met
            20                  25                  30

His Trp Tyr Gln Gln Lys Pro Gly Lys Ala Pro Lys Leu Leu Ile Tyr
            35                  40                  45

Asp Thr Ser Gln Leu Ala Ser Gly Val Pro Ser Arg Phe Ser Gly Ser
            50                  55                  60

Gly Ser Gly Thr Asp Phe Thr Leu Thr Ile Ser Ser Leu Gln Pro Glu
 65                 70                  75                  80

Asp Phe Ala Thr Tyr Tyr Cys Gln Leu Trp Ser Ser Asn Pro Leu Thr
            85                  90                  95

Phe Gly Gly Gly Thr Lys Val Glu Ile Lys
            100                 105

<210> SEQ ID NO 4
<211> LENGTH: 318
```

```
<212> TYPE: DNA
<213> ORGANISM: Artificial Sequence
<220> FEATURE:
<223> OTHER INFORMATION: Synthetic Construct

<400> SEQUENCE: 4
gacatccagc tgacccagtc tccatcctcc ctgtctgcat ctgtaggaga cagagtcacc    60
atcacttgca gagccagttc aagtgtaggt tacatgcact ggtatcagca gaaaccaggg   120
aaagccccta agctcctgat ctatgacaca tcccaactgg cttctggggt cccatcaagg   180
ttcagtggca gtggatctgg gacagatttc actctcacca tcagcagtct gcaacctgaa   240
gattttgcaa cttactactg tcagctgtgg agcagtaacc cgctcacgtt cggcggaggg   300
accaaggtgg agatcaaa                                                 318

<210> SEQ ID NO 5
<211> LENGTH: 5
<212> TYPE: PRT
<213> ORGANISM: Artificial Sequence
<220> FEATURE:
<223> OTHER INFORMATION: Synthetic Construct

<400> SEQUENCE: 5

Asp Tyr Val Thr His
1               5

<210> SEQ ID NO 6
<211> LENGTH: 7
<212> TYPE: PRT
<213> ORGANISM: Artificial Sequence
<220> FEATURE:
<223> OTHER INFORMATION: Synthetic Construct

<400> SEQUENCE: 6

Gly Tyr Ile Phe Thr Asp Tyr
1               5

<210> SEQ ID NO 7
<211> LENGTH: 15
<212> TYPE: DNA
<213> ORGANISM: Artificial Sequence
<220> FEATURE:
<223> OTHER INFORMATION: Synthetic Construct

<400> SEQUENCE: 7
gactatgtta cacac                                                    15

<210> SEQ ID NO 8
<211> LENGTH: 21
<212> TYPE: DNA
<213> ORGANISM: Artificial Sequence
<220> FEATURE:
<223> OTHER INFORMATION: Synthetic Construct

<400> SEQUENCE: 8
ggatacatat tcactgacta t                                             21

<210> SEQ ID NO 9
<211> LENGTH: 17
<212> TYPE: PRT
<213> ORGANISM: Artificial Sequence
<220> FEATURE:
<223> OTHER INFORMATION: Synthetic Construct

<400> SEQUENCE: 9
```

```
Tyr Ile Asn Pro Tyr Asn Ala Gly Thr Lys Tyr Asn Glu Arg Phe Lys
1               5                   10                  15

Gly
```

<210> SEQ ID NO 10
<211> LENGTH: 6
<212> TYPE: PRT
<213> ORGANISM: Artificial Sequence
<220> FEATURE:
<223> OTHER INFORMATION: Synthetic Construct

<400> SEQUENCE: 10

```
Asn Pro Tyr Asn Ala Gly
1               5
```

<210> SEQ ID NO 11
<211> LENGTH: 51
<212> TYPE: DNA
<213> ORGANISM: Artificial Sequence
<220> FEATURE:
<223> OTHER INFORMATION: Synthetic Construct

<400> SEQUENCE: 11
tatattaatc cttacaatgc tggtactaaa tacaatgaga ggttcaaagg c        51

<210> SEQ ID NO 12
<211> LENGTH: 18
<212> TYPE: DNA
<213> ORGANISM: Artificial Sequence
<220> FEATURE:
<223> OTHER INFORMATION: Synthetic Construct

<400> SEQUENCE: 12
aatccttaca atgctggt        18

<210> SEQ ID NO 13
<211> LENGTH: 11
<212> TYPE: PRT
<213> ORGANISM: Artificial Sequence
<220> FEATURE:
<223> OTHER INFORMATION: Synthetic Construct

<400> SEQUENCE: 13

```
Asp Tyr Arg Tyr Glu Ile Tyr Gly Met Asp Tyr
1               5                   10
```

<210> SEQ ID NO 14
<211> LENGTH: 33
<212> TYPE: DNA
<213> ORGANISM: Artificial Sequence
<220> FEATURE:
<223> OTHER INFORMATION: Synthetic Construct

<400> SEQUENCE: 14
gattataggt acgaaatcta tggtatggac tac        33

<210> SEQ ID NO 15
<211> LENGTH: 449
<212> TYPE: PRT
<213> ORGANISM: Artificial Sequence
<220> FEATURE:
<223> OTHER INFORMATION: Synthetic Construct

<400> SEQUENCE: 15

```
Glu Val Gln Leu Val Glu Ser Gly Gly Gly Leu Val Gln Pro Gly Gly
1               5                   10                  15
```

```
Ser Leu Arg Leu Ser Cys Ala Ala Ser Gly Tyr Ile Phe Thr Asp Tyr
            20                  25                  30

Val Thr His Trp Val Arg Gln Ala Pro Gly Lys Gly Leu Glu Trp Ile
        35                  40                  45

Ala Tyr Ile Asn Pro Tyr Asn Ala Gly Thr Lys Tyr Asn Glu Arg Phe
    50                  55                  60

Lys Gly Arg Phe Thr Ile Ser Ser Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Tyr Arg Tyr Glu Ile Tyr Gly Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Arg Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Leu Leu Gln Gly Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430
```

Glu Ala Leu His Asn His Tyr Thr Gln Lys Ser Leu Ser Leu Ser Pro
            435                 440                 445

Gly

<210> SEQ ID NO 16
<211> LENGTH: 1353
<212> TYPE: DNA
<213> ORGANISM: Artificial Sequence
<220> FEATURE:
<223> OTHER INFORMATION: Synthetic Construct

<400> SEQUENCE: 16

| | |
|---|---|
| gaggtgcagc tggtggagtc tggcggcgga ctggtgcagc ctggcggctc tctgagactg | 60 |
| tcttgtgccg cctccggata catattcact gactatgtta cacactgggt gaggcaggcc | 120 |
| cctggcaagg gcctggagtg gatcgcctat attaatcctt acaatgctgg tactaaatac | 180 |
| aatgagaggt tcaaaggccg gttcaccatc tccagcgaca cgccaagaa ctccctgtac | 240 |
| ctccagatga actccctgag ggccgaggat accgccgtgt actactgtgc cagagattat | 300 |
| aggtacgaaa tctatggtat ggactactgg ggccagggca ccctggtgac cgtgtcctct | 360 |
| gcgtcgacca agggcccatc ggtcttcccc ctggcaccct cctccaagag cacctctggg | 420 |
| ggcacagcgg ccctgggctg cctggtcaag gactacttcc ccgaaccggt gacggtgtcg | 480 |
| tggaactcag gcgccctgac cagcggcgtg cacaccttcc cggctgtcct acagtcctca | 540 |
| ggactctact ccctcagcag cgtagtgacc gtgccctcca gcagcttggg cacccagacc | 600 |
| tacatctgca acgtgaatca caagcccagc aacaccaagg tggacaagaa agttgagccc | 660 |
| aaatcttgtg accgcactca cacatgccca ccgtgcccag cacctgaact cctgggggga | 720 |
| ccgtcagtct tcctcttccc cccaaaaccc aaggacaccc tcatgatctc ccggacccct | 780 |
| gaggtcacat gcgtggtggt ggacgtgagc cacgaagacc ctgaggtcaa gttcaactgg | 840 |
| tacgtggacg gcgtggaggt gcataatgcc aagacaaagc cgcgggagct gctgcagggg | 900 |
| agcacgtacc gtgtggtcag cgtcctcacc gtcctgcacc aggactggct gaatggcaag | 960 |
| gagtacaagt gcaaggtctc caacaaagcc ctcccagccc ccatcgagaa aaccatctcc | 1020 |
| aaagccaaag ggcagccccg agaaccacag gtgtacaccc tgcccccatc ccgggaggag | 1080 |
| atgaccaaga accaggtcag cctgacctgc ctggtcaaag gcttctatcc cagcgacatc | 1140 |
| gccgtggagt gggagagcaa tgggcagccg gagaacaact acaagaccac gcctcccgtg | 1200 |
| ctggactccg acggctcctt cttcctctat agcaagctca ccgtggacaa gagcaggtgg | 1260 |
| cagcagggga acgtcttctc atgctccgtg atgcatgagg ctctgcacaa ccactacacg | 1320 |
| cagaagagcc tctccctgtc ccccggatag tag | 1353 |

<210> SEQ ID NO 17
<211> LENGTH: 10
<212> TYPE: PRT
<213> ORGANISM: Artificial Sequence
<220> FEATURE:
<223> OTHER INFORMATION: Synthetic Construct

<400> SEQUENCE: 17

Arg Ala Ser Ser Ser Val Gly Tyr Met His
1               5                   10

<210> SEQ ID NO 18
<211> LENGTH: 30
<212> TYPE: DNA
<213> ORGANISM: Artificial Sequence

```
<220> FEATURE:
<223> OTHER INFORMATION: Synthetic Construct

<400> SEQUENCE: 18
agagccagtt caagtgtagg ttacatgcac                                           30

<210> SEQ ID NO 19
<211> LENGTH: 7
<212> TYPE: PRT
<213> ORGANISM: Artificial Sequence
<220> FEATURE:
<223> OTHER INFORMATION: Synthetic Construct

<400> SEQUENCE: 19

Asp Thr Ser Gln Leu Ala Ser
1               5

<210> SEQ ID NO 20
<211> LENGTH: 21
<212> TYPE: DNA
<213> ORGANISM: Artificial Sequence
<220> FEATURE:
<223> OTHER INFORMATION: Synthetic Construct

<400> SEQUENCE: 20
gacacatccc aactggcttc t                                                    21

<210> SEQ ID NO 21
<211> LENGTH: 9
<212> TYPE: PRT
<213> ORGANISM: Artificial Sequence
<220> FEATURE:
<223> OTHER INFORMATION: Synthetic Construct

<400> SEQUENCE: 21

Gln Leu Trp Ser Ser Asn Pro Leu Thr
1               5

<210> SEQ ID NO 22
<211> LENGTH: 27
<212> TYPE: DNA
<213> ORGANISM: Artificial Sequence
<220> FEATURE:
<223> OTHER INFORMATION: Synthetic Construct

<400> SEQUENCE: 22
cagctgtgga gcagtaaccc gctcacg                                              27

<210> SEQ ID NO 23
<211> LENGTH: 213
<212> TYPE: PRT
<213> ORGANISM: Artificial Sequence
<220> FEATURE:
<223> OTHER INFORMATION: Synthetic Construct

<400> SEQUENCE: 23

Asp Ile Gln Leu Thr Gln Ser Pro Ser Ser Leu Ser Ala Ser Val Gly
1               5                   10                  15

Asp Arg Val Thr Ile Thr Cys Arg Ala Ser Ser Ser Val Gly Tyr Met
            20                  25                  30

His Trp Tyr Gln Gln Lys Pro Gly Lys Ala Pro Lys Leu Leu Ile Tyr
        35                  40                  45

Asp Thr Ser Gln Leu Ala Ser Gly Val Pro Ser Arg Phe Ser Gly Ser
    50                  55                  60
```

```
Gly Ser Gly Thr Asp Phe Thr Leu Thr Ile Ser Ser Leu Gln Pro Glu
 65                  70                  75                  80

Asp Phe Ala Thr Tyr Tyr Cys Gln Leu Trp Ser Ser Asn Pro Leu Thr
                 85                  90                  95

Phe Gly Gly Gly Thr Lys Val Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210
```

```
<210> SEQ ID NO 24
<211> LENGTH: 639
<212> TYPE: DNA
<213> ORGANISM: Artificial Sequence
<220> FEATURE:
<223> OTHER INFORMATION: Synthetic Construct

<400> SEQUENCE: 24
gacatccagc tgacccagtc tccatcctcc ctgtctgcat ctgtaggaga cagagtcacc      60
atcacttgca gagccagttc aagtgtaggt tacatgcact ggtatcagca gaaaccaggg     120
aaagccccta agctcctgat ctatgacaca tcccaactgg cttctggggt cccatcaagg     180
ttcagtggca gtggatctgg gacagatttc actctcacca tcagcagtct gcaacctgaa     240
gattttgcaa cttactactg tcagctgtgg agcagtaacc cgctcacgtt cggcggaggg     300
accaaggtgg agatcaaacg tactgtggct gcaccatctg tcttcatctt cccgccatct     360
gatgagcagt tgaaatctgg aactgcctct gttgtgtgcc tgctgaataa cttctatccc     420
agagaggcca agtacagtg gaaggtggat aacgccctcc aatcgggtaa ctcccaggag     480
agtgtcacag agcaggacag caaggacagc acctacagcc tcagcagcac cctgacgctg     540
agcaaagcag actacgagaa acacaaagtc tacgcctgcg aagtcaccca tcagggcctg     600
agctcgcccg tcacaaagag cttcaacagg ggagagtgt                            639
```

```
<210> SEQ ID NO 25
<211> LENGTH: 110
<212> TYPE: PRT
<213> ORGANISM: Artificial Sequence
<220> FEATURE:
<223> OTHER INFORMATION: Synthetic Construct

<400> SEQUENCE: 25

Ala Pro Glu Leu Leu Gly Gly Pro Ser Val Phe Leu Phe Pro Pro Lys
 1               5                  10                  15

Pro Lys Asp Thr Leu Met Ile Ser Arg Thr Pro Glu Val Thr Cys Val
             20                  25                  30

Val Val Asp Val Ser His Glu Asp Pro Glu Val Lys Phe Asn Trp Tyr
```

```
                35                  40                  45
Val Asp Gly Val Glu Val His Asn Ala Lys Thr Lys Pro Arg Glu Glu
 50                  55                  60

Gln Tyr Asn Ser Thr Tyr Arg Val Val Ser Val Leu Thr Val Leu His
 65                  70                  75                  80

Gln Asp Trp Leu Asn Gly Lys Glu Tyr Lys Cys Lys Val Ser Asn Lys
                 85                  90                  95

Ala Leu Pro Ala Pro Ile Glu Lys Thr Ile Ser Lys Ala Lys
            100                 105                 110

<210> SEQ ID NO 26
<211> LENGTH: 217
<212> TYPE: PRT
<213> ORGANISM: Artificial Sequence
<220> FEATURE:
<223> OTHER INFORMATION: Synthetic Construct

<400> SEQUENCE: 26

Ala Pro Glu Leu Leu Gly Gly Pro Ser Val Phe Leu Phe Pro Pro Lys
  1               5                  10                  15

Pro Lys Asp Thr Leu Met Ile Ser Arg Thr Pro Glu Val Thr Cys Val
             20                  25                  30

Val Val Asp Val Ser His Glu Asp Pro Glu Val Lys Phe Asn Trp Tyr
         35                  40                  45

Val Asp Gly Val Glu Val His Asn Ala Lys Thr Lys Pro Arg Glu Glu
 50                  55                  60

Gln Tyr Asn Ser Thr Tyr Arg Val Val Ser Val Leu Thr Val Leu His
 65                  70                  75                  80

Gln Asp Trp Leu Asn Gly Lys Glu Tyr Lys Cys Lys Val Ser Asn Lys
                 85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Asp Glu Leu
        115                 120                 125

Thr Lys Asn Gln Val Ser Leu Thr Cys Leu Val Lys Gly Phe Tyr Pro
    130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Phe Leu
                165                 170                 175

Tyr Ser Lys Leu Thr Val Asp Lys Ser Arg Trp Gln Gln Gly Asn Val
            180                 185                 190

Phe Ser Cys Ser Val Met His Glu Ala Leu His Asn His Tyr Thr Gln
        195                 200                 205

Lys Ser Leu Ser Leu Ser Pro Gly Lys
    210                 215

<210> SEQ ID NO 27
<211> LENGTH: 330
<212> TYPE: PRT
<213> ORGANISM: Artificial Sequence
<220> FEATURE:
<223> OTHER INFORMATION: Synthetic Construct

<400> SEQUENCE: 27

Ala Ser Thr Lys Gly Pro Ser Val Phe Pro Leu Ala Pro Ser Ser Lys
  1               5                  10                  15
```

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Cys Thr Ile Ser Lys Ala Lys Gly
    210                 215                 220

Gln Pro Arg Glu Pro Leu Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Leu Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 28
<211> LENGTH: 330
<212> TYPE: PRT
<213> ORGANISM: Artificial Sequence
<220> FEATURE:
<223> OTHER INFORMATION: Synthetic Construct

<400> SEQUENCE: 28

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

```
Gly Val His Thr Phe Pro Ala Val Leu Gln Ser Ser Gly Leu Tyr Ser
        50                  55                  60

Leu Ser Ser Val Val Thr Val Pro Ser Ser Leu Gly Thr Gln Thr
 65                  70                  75                  80

Tyr Ile Cys Asn Val Asn His Lys Pro Ser Asn Thr Lys Val Asp Lys
                 85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
            115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
210                 215                 220

Gln Pro Arg Glu Pro Leu Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Cys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
            290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 29
<211> LENGTH: 330
<212> TYPE: PRT
<213> ORGANISM: Artificial Sequence
<220> FEATURE:
<223> OTHER INFORMATION: Synthetic Construct

<400> SEQUENCE: 29

Ala Ser Thr Lys Gly Pro Ser Val Phe Pro Leu Ala Pro Ser Ser Lys
 1               5                  10                  15

Ser Thr Ser Gly Gly Thr Ala Ala Leu Gly Cys Leu Val Lys Asp Tyr
                 20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Leu Gly Thr Gln Thr
 65                  70                  75                  80
```

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
            115                 120                 125

Lys Pro Lys Asp Thr Leu Met Ile Ser Arg Thr Pro Glu Val Thr Cys
            130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
            195                 200                 205

Lys Ala Leu Pro Ala Pro Ile Glu Cys Thr Ile Ser Lys Ala Lys Gly
            210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Cys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
        290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 30
<211> LENGTH: 107
<212> TYPE: PRT
<213> ORGANISM: Artificial Sequence
<220> FEATURE:
<223> OTHER INFORMATION: Synthetic Construct

<400> SEQUENCE: 30

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

```
<210> SEQ ID NO 31
<211> LENGTH: 106
<212> TYPE: PRT
<213> ORGANISM: Artificial Sequence
<220> FEATURE:
<223> OTHER INFORMATION: Synthetic Construct

<400> SEQUENCE: 31

Gly Gln Pro Lys Ala Asn Pro Thr Val Thr Leu Phe Pro Pro Ser Ser
1               5                   10                  15

Glu Glu Leu Gln Ala Asn Lys Ala Thr Leu Val Cys Leu Ile Ser Asp
            20                  25                  30

Phe Tyr Pro Gly Ala Val Thr Val Ala Trp Lys Ala Asp Gly Ser Pro
        35                  40                  45

Val Lys Ala Gly Val Glu Thr Thr Lys Pro Ser Lys Gln Ser Asn Asn
    50                  55                  60

Lys Tyr Ala Ala Ser Ser Tyr Leu Ser Leu Thr Pro Glu Gln Trp Lys
65                  70                  75                  80

Ser His Arg Ser Tyr Ser Cys Gln Val Thr His Glu Gly Ser Thr Val
                85                  90                  95

Glu Lys Thr Val Ala Pro Thr Glu Cys Ser
            100                 105

<210> SEQ ID NO 32
<211> LENGTH: 449
<212> TYPE: PRT
<213> ORGANISM: Artificial Sequence
<220> FEATURE:
<223> OTHER INFORMATION: Synthetic Construct

<400> SEQUENCE: 32

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Ile Phe Thr Asp Tyr
            20                  25                  30

Val Thr His Trp Val Arg Gln Ala Pro Gly Lys Gly Leu Glu Trp Ile
        35                  40                  45

Ala Tyr Ile Asn Pro Tyr Asn Ala Gly Thr Lys Tyr Asn Glu Arg Phe
    50                  55                  60

Lys Gly Arg Phe Thr Ile Ser Ser Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Tyr Arg Tyr Glu Ile Tyr Gly Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205
```

Pro Ser Asn Thr Lys Val Asp Lys Lys Val Glu Pro Lys Ser Cys Asp
    210                 215                 220

Arg Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
            245                 250                 255

Ser Arg Thr Pro Glu Val Thr Cys Val Val Val Asp Val Ser His Glu
        260                 265                 270

Asp Pro Glu Val Lys Phe Asn Trp Tyr Val Asp Gly Val Glu Val His
    275                 280                 285

Asn Ala Lys Thr Lys Pro Arg Glu Leu Leu Gln Gly Ser Thr Tyr Arg
290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
            325                 330                 335

Cys Thr Ile Ser Lys Ala Lys Gly Gln Pro Arg Glu Pro Gln Val Tyr
        340                 345                 350

Thr Leu Pro Pro Ser Arg Glu Glu Met Thr Lys Asn Gln Val Ser Leu
    355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
            405                 410                 415

Lys Ser Arg Trp Gln Gln Gly Asn Val Phe Ser Cys Ser Val Met His
        420                 425                 430

Glu Ala Leu His Asn His Tyr Thr Gln Lys Ser Leu Ser Leu Ser Pro
    435                 440                 445

Gly

<210> SEQ ID NO 33
<211> LENGTH: 449
<212> TYPE: PRT
<213> ORGANISM: Artificial Sequence
<220> FEATURE:
<223> OTHER INFORMATION: Synthetic Construct

<400> SEQUENCE: 33

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Ile Phe Thr Asp Tyr
            20                  25                  30

Val Thr His Trp Val Arg Gln Ala Pro Gly Lys Gly Leu Glu Trp Ile
        35                  40                  45

Ala Tyr Ile Asn Pro Tyr Asn Ala Gly Thr Lys Tyr Asn Glu Arg Phe
    50                  55                  60

Lys Gly Arg Phe Thr Ile Ser Ser Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Tyr Arg Tyr Glu Ile Tyr Gly Met Asp Tyr Trp Gly Gln
            100                 105                 110

```
Gly Thr Leu Val Thr Val Ser Ser Ala Ser Thr Lys Gly Pro Ser Val
            115                 120                 125

Phe Pro Leu Ala Pro Ser Ser Lys Ser Thr Ser Gly Gly Thr Ala Ala
130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Arg Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Leu Gln Gly Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Cys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly

<210> SEQ ID NO 34
<211> LENGTH: 449
<212> TYPE: PRT
<213> ORGANISM: Artificial Sequence
<220> FEATURE:
<223> OTHER INFORMATION: Synthetic Construct

<400> SEQUENCE: 34

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Ile Phe Thr Asp Tyr
```

```
            20                  25                  30
Val Thr His Trp Val Arg Gln Ala Pro Gly Lys Gly Leu Glu Trp Ile
             35                  40                  45

Ala Tyr Ile Asn Pro Tyr Asn Ala Gly Thr Lys Tyr Asn Glu Arg Phe
 50                  55                  60

Lys Gly Arg Phe Thr Ile Ser Ser Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

Ala Arg Asp Tyr Arg Tyr Glu Ile Tyr Gly Met Asp Tyr Trp Gly Gln
                100                 105                 110

Gly Thr Leu Val Thr Val Ser Ser Ala Ser Thr Lys Gly Pro Ser Val
                115                 120                 125

Phe Pro Leu Ala Pro Ser Ser Lys Ser Thr Ser Gly Gly Thr Ala Ala
            130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
                180                 185                 190

Ser Ser Ser Leu Gly Thr Gln Thr Tyr Ile Cys Asn Val Asn His Lys
            195                 200                 205

Pro Ser Asn Thr Lys Val Asp Lys Lys Val Glu Pro Lys Ser Cys Asp
        210                 215                 220

Arg Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
                260                 265                 270

Asp Pro Glu Val Lys Phe Asn Trp Tyr Val Asp Gly Val Glu Val His
            275                 280                 285

Asn Ala Lys Thr Lys Pro Arg Glu Leu Leu Gln Gly Ser Thr Tyr Arg
        290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Cys Thr Ile Ser Lys Ala Lys Gly Gln Pro Arg Glu Pro Gln Val Tyr
                340                 345                 350

Thr Leu Pro Pro Ser Arg Glu Glu Met Thr Lys Asn Gln Val Ser Leu
            355                 360                 365

Thr Cys Leu Val Lys Gly Phe Tyr Pro Ser Asp Ile Ala Val Glu Trp
        370                 375                 380

Glu Ser Asn Gly Gln Pro Glu Asn Asn Tyr Cys Thr Thr Pro Pro Val
385                 390                 395                 400

Leu Asp Ser Asp Gly Ser Phe Phe Leu Tyr Ser Lys Leu Thr Val Asp
                405                 410                 415
```

```
Lys Ser Arg Trp Gln Gln Gly Asn Val Phe Ser Cys Ser Val Met His
            420                 425                 430
Glu Ala Leu His Asn His Tyr Thr Gln Lys Ser Leu Ser Leu Ser Pro
            435                 440                 445
Gly
```